(12) United States Patent
Newman et al.

(10) Patent No.: US 8,618,293 B2
(45) Date of Patent: Dec. 31, 2013

(54) REDOX MEDIATORS

(75) Inventors: Christopher Paul Newman, Holmfirth (GB); Luet Lok Wong, Oxford (GB); Hugh Allen Oliver Hill, Oxford (GB); Tai-Chu Lau, Kowloon Tong (HK)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 523 days.

(21) Appl. No.: 12/663,821

(22) PCT Filed: Jun. 17, 2008 (Under 37 CFR 1.47)

(86) PCT No.: PCT/GB2008/002064
§ 371 (c)(1), (2), (4) Date: Aug. 5, 2010

(87) PCT Pub. No.: WO2008/155531
PCT Pub. Date: Dec. 24, 2008

(65) Prior Publication Data
US 2011/0262950 A1 Oct. 27, 2011

(30) Foreign Application Priority Data
Jun. 19, 2007 (GB) .................................. 0711849.0

(51) Int. Cl.
*C07F 15/00* (2006.01)
*C12Q 1/32* (2006.01)

(52) U.S. Cl.
USPC .................... 546/2; 548/101; 556/37; 435/26

(58) Field of Classification Search
USPC .................... 546/2; 548/101; 435/26; 556/37
See application file for complete search history.

(56) References Cited

U.S. PATENT DOCUMENTS

| 4,745,076 A | 5/1988 | Muller et al. |
| 5,958,783 A | 9/1999 | Josel et al. |

FOREIGN PATENT DOCUMENTS

| EP | 0 580 979 A3 | 2/1994 |
| WO | WO 96/13510 A1 | 5/1996 |
| WO | WO 96/25514 | 8/1996 |
| WO | 01/36430 A1 | 5/2001 |
| WO | WO 2004/009604 A3 | 1/2004 |
| WO | 2006/018649 A1 | 2/2006 |
| WO | 2007/072018 A2 | 6/2007 |

OTHER PUBLICATIONS

Krause: "Synthesis of Mixed Complexes of Ruthenium(II) with 2,2'—Dipyridyl" Inorganica Chimica Acta, 22 (1977) pp. 209-213.
Solorzano et al.: "Prepartion of Arene Ruthenium(II) Complexes with Activated Ligands for Protein Labeling" Inorganica Chimica Acta, 97 (1985) pp. 135-141.
Hung et al.: "Aquo Chemistry of Monoarene Complexes of Osmium(II) and Ruthenium(II)" Inorganic Chemistry, 1981, vol. 20 pp. 457-463.
Da Silva et al.: "Ruthenium(II) Macrocyclic Complexes with Inert Choride and Labile Azines. Sythesis and Properties of the Macrocyclic Complexes trans-Chloro(azine) (1,4,8,11-tetraazacyclotetradecan)ruthenium(II), trans-[RuCl(cyclam)L]+1", Inorganic Chemistry, 1992, vol. 31, pp. 3313-3316.
Chen et al.:"Organometallic Ruthenium(II) Diamine Anitcancer Complexes: Arene-Nucleobase Stacking and Sterospecific Hydrogen-Bonding in Guanine Adducts" Journal of the American Chemical Society, vol. 124, No. 12, Mar. 27, 2002, pp. 3064-3082.
Che et al.: "Ruthenium (III) Tertiary Amine Complexes" Inorganic Chemistry, 1985, vol. 24, pp. 1601-1602.
Harvey, et al. Preparation of ruthenium(II) chloride complexes of polybasic amines, Inorganica Chimica Acta 359, 839-845 (2006).
Gossens, et al., Rational Design of Organo-Ruthenium Anticancer Compounds, Chimia 59 (2005) 81-84.
Schneider, et al., Mononuclear ruthenium(III) complexes of the Type LRuX3(X=Cl-, NCO-, NCS-, N3-; L = 1,4,7-trimethyl-1,4,7-triazacyclononame), Zietscrift fuer Naturforschung, B: Chemical Sciences (1994), 49(3), 330-6.

*Primary Examiner* — Chih-Min Kam
(74) *Attorney, Agent, or Firm* — Krieg DeVault LLP

(57) ABSTRACT

The present invention relates to ruthenium and osmium complexes of Formula $[M(A)_w(B)_x(C)_y]^m(X^z)_n$, per se and the use of ruthenium and osmium complexes of Formula I as redox mediators in electrochemical biosensors.

14 Claims, 44 Drawing Sheets

[Ru(Me$_3$tacn)(acac)(4-$^t$Bupy)]$^{2+}$

REDOX MEDIATORS

CROSS REFERENCE TO RELATED APPLICATIONS

Figure 1:
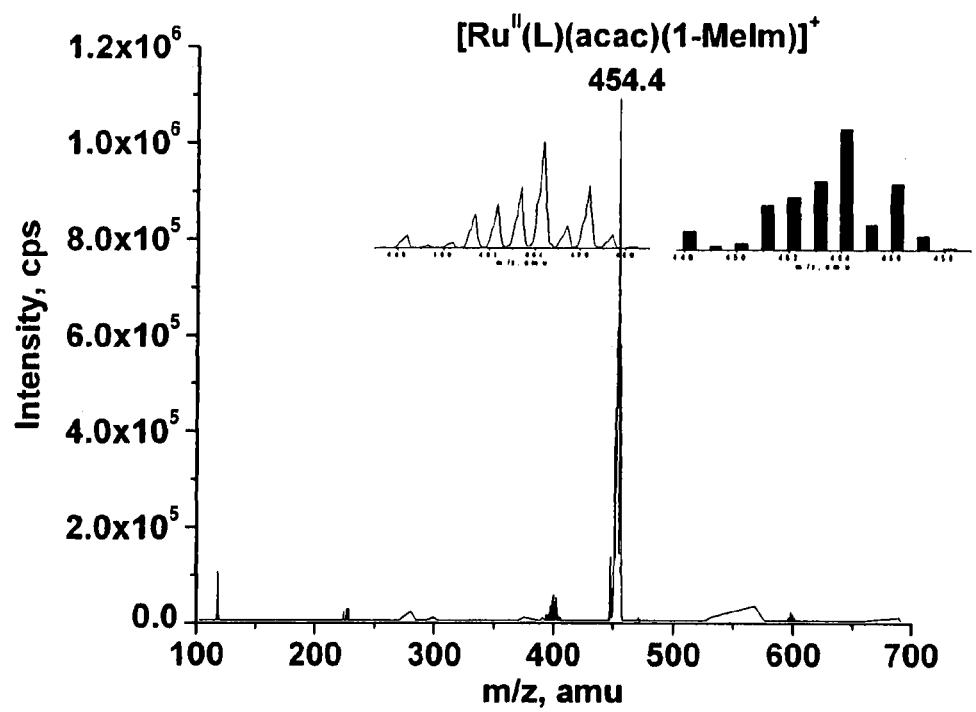

This is a United States National Phase Application under 35 U.S.C. §371 of International Patent Application No. PCT/GB2008/002064 filed Jun. 17, 2008 which claims the benefit of British Patent Application No. 0711849.0 filed Jun. 19, 2007; both of which are incorporated by reference herein in their entireties. The International Application was published in English on Dec. 24, 2008 as WO 2008/155531 A1 under PCT Article 21(2).

The present invention relates to novel ruthenium and osmium complexes, the use of ruthenium and osmium complexes as a redox mediator or in a biosensor. In particular, the present invention relates to the use of a ruthenium complex having an overall charge on the ruthenium-containing species less than 3+in the ruthenium (III) state as a redox mediator.

A biosensor is an analytical tool combining a biochemical recognition component or sensing element with a physical transducer. A biosensor has broad application in fields as diverse as personal health monitoring, environmental screening and monitoring, bioprocess monitoring and within the food and beverage industry. Biosensors offer the convenience and facility of distributed measurement ie the potential ability to take the assay to the point of concern or care. A properly designed and manufactured biosensor may be conveniently mass-produced.

The biological sensing element may be an enzyme, antibody, DNA sequence or microorganism which serves (for example) to catalyze selectively a reaction or facilitate a binding event. The selectivity allows for the operation of the biosensor in a complex sample matrix (eg a body fluid). The transducer converts the biochemical event into a measurable signal thereby providing the means for detecting it. The measurable signal may be a spectral change caused by the production or consumption of the product or substrate of an enzymatic reaction or a mass change associated with biochemical complexation. The transducer may be optically-based to measure optical absorption, fluorescence or refractive index. The transducer may be mass-based to measure a change in mass that accompanies a binding reaction. The transducer may be thermally-based to measure a change in enthalpy (heat) or amperometry. The transducer may be impedance-based to measure a change in an electrical property that accompanies the interaction of an analyte/bio-recognition layer.

Enzyme-based biosensors are used widely in the detection of analytes in clinical, environmental, agricultural and biotechnological applications. They offer specificity, sensitivity and operate under mild conditions. Analytes that can be measured in clinical assays of fluids of the human body include (for example) glucose, lactate, cholesterol, bilirubin and amino acids. Levels of these analytes in biological fluids (such as blood) are important for the diagnosis and monitoring of diseases. There are however disadvantages associated with use of biosensors which include the vulnerability of the transducer to foulants and interferences.

Sensors which generally exploit enzyme-based systems are provided as either point-of-care or over-the-counter devices. They can be used to test fresh, unmodified, whole blood finger prick samples in order to determine the concentrations of total cholesterol, triglycerides, HDL and LDL within (for example) 1 to 5 minutes of adding the sample to a device. These four parameters in combination have been clinically proven to give a very good indication of the risk of heart disease in adults. It is well, known that high cholesterol is asymptomatic and it is recommended that an adult should have a test to assess their risk. If their risk is found to be high, it may be significantly reduced by correct management of diet alone or in combination with the administration of a therapeutic drug.

An electrochemical assay is typically performed in a cell with two or three electrodes which include at least one measuring or working electrode and one reference electrode. In a three electrode system, the third electrode is a counter-electrode. In a two electrode system, the reference electrode also serves as the counter-electrode. The electrodes are connected through a circuit such as a potentiostat. The measuring or working electrode is a carbon or metal conductor or semiconductor.

In an example of an enzyme-based biosensor, there is utilised an electrochemical assay to detect an analyte. Use is made of a change in the oxidation state of a mediator which interacts with an enzyme which has reacted with the analyte. The oxidation state of the mediator is chosen so that it interacts with the enzyme on addition of the substrate. The analyte reacts with a stoichiometric concentration of the mediator via the enzyme. This causes the mediator to be oxidised or reduced (depending on the enzymatic reaction) and this change can be measured by determining the current generated at a given potential or by determining the potential at a given current.

In a further example of an enzyme-based biosensor, a sufficiently large voltage passed to the working electrode causes a redox enzyme to be electrooxidized or electroreduced. The enzyme is specific to the analyte to be detected or to a product of the analyte. The turnover rate of the enzyme is typically related (eg linearly) to the concentration of the analyte itself or to its product in the test solution.

The electrooxidation or electroreduction of the enzyme is often facilitated by the presence of a redox mediator in the solution or on the electrode. The redox mediator generally assists in the electrical communication between the working electrode and the enzyme. The redox mediator can be dissolved in the fluid to be analyzed which is in electrolytic contact with the electrodes. A useful device may be made (for example) by coating an electrode with a film that includes a redox mediator and an enzyme catalytically specific to the desired analyte or its products. A diffusional redox mediator which can be soluble or insoluble in water functions by shuttling electrons between (for example) the enzyme and the electrode. When the substrate of the enzyme is electrooxidized, the redox mediator transports electrons from the substrate-reduced enzyme to the electrode. When the substrate is electroreduced, the redox mediator transports electrons from the electrode to the substrate-oxidized enzyme.

Conventional enzyme-based electrochemical sensors have employed a number of redox mediators including monomeric ferrocenes, quinoid-compounds (such as quinines eg benzoquinones), nickel cyclamates and ruthenium amines. For the most part, these redox mediators have one or more of the following limitations:

the solubility of the redox mediator in the test solutions is low, the chemical, light, thermal or pH stability of the redox mediator is poor, the redox mediator does not exchange electrons rapidly enough with the enzyme or the electrode or both.

Additionally the oxidation potential of many of these redox mediators is so high that at the potential where the reduced mediator is electrooxidized on the electrode, solution components other than the analyte are also electrooxidized. In other cases, the reduction potential is so low that the solution components (such as for example dissolved oxygen) are also rapidly electroreduced. As a result, the sensor utilizing the mediator is not sufficiently specific.

Ruthenium-based complexes have previously been utilised as redox mediators in reactions containing (for example) cholesterol dehydrogenase. For example, a $[Ru^{II}(NH_3)_6]^{2+}$ species is converted to $[Ru^{III}(NH_3)_6]^{3+}$ at an electrode poised at a suitable potential. The current is proportional to the amount of $[Ru^{II}(NH_3)_6]^{2+}$ species formed via the enzymatic reaction. However a highly-charged species such as $[Ru^{III}(NH_3)_6]^{3+}$ forms (to a greater or lesser extent) complexes which are usually in the form of ion-pairs with negatively-charged groups on enzymes and the electrode surface. This impedes the reactions necessary for the analytical process to occur effectively and efficiently.

It would therefore be desirable to utilise a redox mediator which forms less strong complexes or none at all with the components of the analytical mixture and the electrode so that measured responses are more reliable, stable and reproducible.

According to a first aspect of the present invention there is provided the use of a complex of Formula I

 Formula I (wherein
M is ruthenium or osmium and has an oxidation state of 0, 1, 2, 3 or 4;
each of w, x, and y is an integer independently selected from the integers 1 to 4;
m is an integer selected from the integers −5 to +4;
n is an integer selected from selected from the integers 1 to 5
z is an integer selected from the integers −2 to +1;
A is a monodentate 5- or 6-membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino and alkylthio or A is NCS;
B is a bi-, tri-, tetra-, penta- or hexadentate ligand which is linear having the formula R$^1$RN(C$_2$H$_4$NR)$_w$R$^1$ or cyclic having the formula (RNC$_2$H$_4$)$_v$, (RNC$_2$H$_4$)$_p$(RNC$_3$H$_6$)$_q$ or [(RNC$_2$H$_4$)(RNC$_3$H$_6$)]$_s$, wherein
w is an integer selected from the integers 1-5,
v is an integer selected from the integers 3-6,
each of p and q is an integer independently selected from the integers 1-3 whereby the sum of p and q is 4, 5 or 6,
s is either 2 or 3 and
each of R and R$^1$ is independently hydrogen or alkyl;
C is a ligand other than B; and
X is a counter ion,
wherein the number of coordinating atoms is 6) with the exception of $[Ru^{III}(Me_3tacn)(acac)(py)](NO_3)_2$ as a redox mediator.

In a preferred embodiment of the use according to the invention, in the complex of Formula I:
A is a monodentate 5- or 6-membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino and alkylthio; and
C is a ligand other than A or B.

The ligand A in the complex of Formula I may be selected from the group consisting of NCS, imidazole, pyrazole, thiazole, oxazole, isoquinoline, substituted pyridyl (eg 3- and/or 4-substituted pyridyl) and isomers thereof.

The ligand A in the complex of Formula I may be selected from the group consisting of imidazole, pyrazole, thiazole, oxazole and isomers thereof.

The ligand A in the complex of Formula I may be or contain a 5- or 6-membered aromatic ligand containing 3 nitrogen heteroatoms. The ligand A in the complex of Formula I is preferably triazine or triazole.

The ligand A in the complex of Formula I may be guanine or adenine.

The ligand A in the complex of Formula I may be substituted by one or more substituents selected from the group consisting of C$_1$-C$_6$ alkyl, C$_1$-C$_6$ alkoxy, C$_2$-C$_6$ alkenyl, C$_2$-C$_6$ alkynyl, halogen, carboxy, amino, C$_{1-6}$-alkylamino, C$_{1-6}$-dialkylamino and hydroxyl.

The ligand A in the complex of Formula I may be substituted by one or more substituents selected from the group consisting of C$_1$-C$_6$ alkyl, C$_1$-C$_6$ alkoxy, C$_2$-C$_6$ alkenyl, C$_2$-C$_6$ alkynyl and halogen. Preferably the ligand A in the complex of Formula I is substituted by one or more substituents selected from the group consisting of methyl, ethyl, propyl, iso-propyl, butyl, t-butyl, methoxy, ethoxy, ethenyl, propenyl, butenyl, ethynyl and propynyl.

The ligand B in the complex of Formula I may be a bi-, tri- or tetra-dentate ligand which may be linear having the formula R$^1$RN(C$_2$H$_4$NR)$_r$R$^1$ or cyclic having the formula (RNC$_2$H$_4$)$_v$, (RNC$_2$H$_4$)$_p$(RNC$_3$H$_6$)$_q$ or [(RNC$_2$H$_4$)(RNC$_3$H$_6$)]$_s$, wherein r is an integer selected from the integers 1-3, v is 3 or 4, each of p and q is an integer independently selected from the integers 1-3 whereby the sum of p and q is 4 and s is 2 or 3.

Preferably the ligand B in the complex of Formula I is a tri- or tetra-dentate ligand which is cyclic having the formula (RNC$_2$H$_4$)$_v$, wherein v is 3 or 4.

The ligand B in the complex of Formula I may be 1,4,7-trimethyl-1,4,7-triazacyclononane, 1,4,8,11-tetramethyl-1,4,8,11-tetra-azacyclotetradecane, 1,1,4,7,10,10-hexamethyltriethylenetetramine, 1,2-dimethylethylenediamine or 1,1,2,2-tetramethylethylenediamine.

The ligand B in the complex of Formula I may be 1,4,7-trimethyl-1,4,7-triazacyclononane, 1,1,4,7,10,10-hexamethyltriethylenetetramine, 1,2-dimethylethylenediamine or 1,1,2,2-tetramethylethylenediamine.

A preferred ligand B in the complex of Formula I is 1,4,7-trimethyl-1,4,7-triazacyclononane.

The ligand C in the complex of Formula I may be selected from the group consisting of an amine ligand (such as NH$_3$), CO, CN, NCS, a halogen, acetylacetonate (acac), 3-bromoacetylacetonate (Bracac), oxalate, troplone, pyridine and 5-chloro-8-hydroxyquinoline.

The ligand C in the complex of Formula I may be selected from the group consisting of an amine ligand (such as NH$_3$), CO, CN, a halogen, acetylacetonate (acac), 3-bromo-acetylacetonate (Bracac), oxalate, pyridine and 5-chloro-8-hydroxyquinoline.

A preferred ligand C in the complex of Formula I is acac.

The ligands A, B and C in the complex of Formula I may be bidentate. The geometry of the complex of Formula I may be cis or trans.

The oxidation state of the metal in the complex of Formula I may be 2+, 3+ or 4+. The oxidation state of the metal in the complex of Formula I is preferably 3+.

The ligands A, B and C may be selected such that the overall charge on the complex of Formula I is selected from the group consisting of +3, +2, +1, 0, −1, −2 and −3.

The counterion X in the complex of Formula I may be $F^-$, $Cl^-$, $Br^-$, $I^-$, $NO_3^-$, $NH_4^+$, $NR_4^+$, $PF_6^-$, $CF_3SO_3^-$, $SO_4^{2-}$, $ClO_4^-$, $K^+$, $Na^+$, $Li^+$ or a combination thereof.

The complex of Formula I used as a redox mediator in accordance with the present invention may be $[Ru^{III}(1,4,7\text{-trimethyl-1,4,7-triazacyclononane})(acac)(N\text{-methylimidazole})](NO_3)_2$, $[Ru^{III}(1,4,7\text{-trimethyl-1,4,7-triazacyclononane})(acac)(4\text{-methylpyridine})]Cl_2$, $[Ru^{III}(1,4,7\text{-trimethyl-1,4,7-triazacyclononane})(acac)(3\text{-chloropyridine})](NO_3)_2$, $[Ru^{III}(1,4,7\text{-trimethyl-1,4,7-triazacyclononane})(acac)(isonicotinamide)](NO_3)_2$, $[Ru^{III}(1,4,7\text{-trimethyl-1,4,7-triazacyclononane})(acac)pyrazine](NO3)_2$, $[Ru^{III}(1,4,7\text{-trimethyl-1,4,7-triazacyclononane})(acac)(4\text{-methoxypyridine})](NO_3)_2$, $[Ru^{III}(1,4,7\text{-trimethyl-1,4,7-triazacyclononane})(acac)(4\text{-dimethylaminopyridine})](NO_3)_2$, $[Ru^{III}(1,4,7\text{-trimethyl-1,4,7-triazacyclononane})(acac)(4\text{-t-butyl-pyridine})](NO_3)_2$, $[Ru^{III}(1,4,7\text{-trimethyl-1,4,7-triazacyclononane})(acac)(isoquinoline)](NO_3)_2$, $[Ru^{III}(1,4,7\text{-trimethyl-1,4,7-triazacyclononane})(tropolone)(pyridine)](NO_3)_2$, $[Ru^{III}(1,4,7\text{-trimethyl-1,4,7-triazacyclononane})(tropolone)(4\text{-t-butyl-pyridine})](NO_3)_2$, $[Ru^{III}(1,4,7\text{-trimethyl-1,4,7-triazacyclononane})(acac)(3,4\text{-dimethylpyridine})](CF_3SO_3)_2$, $[Ru^{III}(1,4,7\text{-trimethyl-1,4,7-triazacyclononane})(acac)(3\text{-hydroxypyridine})](NO_3)_2$ or $[Ru^{III}(1,4,8,11\text{-tetramethyl-1,4,8,11-tetra-azacyclotetradecane})(NCS)_2](ClO_4)$.

The complex of Formula I used as a redox mediator in accordance with the present invention may be $[Ru^{III}(1,4,7\text{-trimethyl-1,4,7-triazacyclononane})(acac)(N\text{-methylimidazole})](PF_6)_2$, or $[Ru^{III}(1,4,7\text{-trimethyl-1,4,7-triazacyclononane})(acac)(N\text{-methylimidazole})](NO_3)_2$.

The complex of Formula I may be used as a redox mediator in accordance with the present invention in an electrochemical sensor. The electrochemical sensor may include a microband electrode. The electrochemical sensor may be an electrochemical biosensor. The electrochemical sensor may be used to detect an analyte in a bodily fluid, environmental sample, food, beverage, veterinary sample or pharmaceutical.

The complex of Formula I may be used as a redox mediator in accordance with the invention at a pH of 6 to 10, preferably at a pH of 7 to 9.

According to a second aspect of the present invention there is provided the use of a ruthenium complex of Formula I as hereinbefore defined in a biosensor.

The biosensor may be used with a compatible biochemical analyte. The analyte may be found in a biological fluid. The analyte may be selected from the group consisting of an enzyme, enzyme substrate, antigen, antibody, nucleic acid sequence, cholesterol, cholesterol ester, lipoprotein, triglyceride and microorganism.

The complex of Formula I as hereinbefore defined may be used in a biosensor which consists of (for example) a strip with four reagent wells and a common pseudo reference. Each well may have a tubular micro-band working electrode. The sensing component of the strip may be provided by drying different specially formulated reagents comprising at least an enzyme and a mediator that is capable of interacting with specific analytes in the test sample in each well. Since different reagents may be added and dried to each well, it is possible to complete multi-analyte testing using a single test sample. The number of wells is variable and so the number of unique tests is variable. For example, sensors having between 1 and 6 wells may be used.

The complex of Formula 1 as hereinbefore defined may be used in a biosensor which consists of (for example) a conventional microelectrode which typically has a working microelectrode and a reference electrode. The working electrode may be made of palladium, platinum, gold or carbon. The counter electrode may be typically carbon, Ag/AgCl, $Ag/Ag_2SO_4$, palladium, gold, platinum, $Cu/CuSO_4$, $Hg/HgO$, $Hg/HgCl_2$, $Hg/HgSO_4$ or $Zn/ZnSO_4$. Preferably the working electrode is in a wall of a receptacle forming the microelectrode. Examples of microelectrodes which can be used in the present invention are those disclosed in WO-A-03/097860.

According to a third aspect of the present invention there is provided a detection system for measuring an analyte comprising:
  (a) contacting a sample which contains the analyte with a solution containing a redox mediator according to Formula I as defined hereinbefore;
  (b) incubating the contacted sample under conditions that cause the enzyme to act on the analyte;
  (c) subjecting the incubated sample of step (b) to conditions which result in a change in a measurable signal; and
  (d) measuring the measurable signal.

The measurable signal may be an electrochemical, colourimetric, thermal, impedometric, capacitive or spectroscopic signal. The measurable signal may be an electrochemical signal measured at a microband electrode. The electrochemical signal may be detected using a microband electrode in an amperometric detection method.

According to a fourth aspect of the present invention there is provided a complex according to Formula I

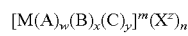

$$[M(A)_w(B)_x(C)_y]^m(X^z)_n \qquad \text{Formula I}$$

(wherein
  M is ruthenium or osmium and has an oxidation state of 0, 1, 2, 3 or 4;
  each of w, x, and y is an integer independently selected from the integers 1 to 4;
  m is an integer selected from the integers −5 to +4;
  n is an integer selected from selected from the integers 1 to 5
  z is an integer selected from the integers −2 to +1;
  A is a monodentate 5- or 6-membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —$NO_2$, —CN, —$CO_2H$, —$SO_3H$, —$NHNH_2$, —SH, aryl, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxyamino and alkylthio;
  B is a bi-, tri-, tetra-, penta- or hexadentate ligand which is linear having the formula $R^1RN(C_2H_4NR)_wR^1$ or cyclic having the formula $(RNC_2H_4)_v$, $(RNC_2H_4)_p(RNC_3H_6)_q$ or $[(RNC_2H_4)(RNC_3H_6)]_s$, wherein
    w is an integer selected from the integers 1-5,
    v is an integer selected from the integers 3-6, each of p and q is an integer independently selected from the integers 1-3 whereby the sum of p and q is 4, 5 or 6, s is either 2 or 3 and each of R and $R^1$ is independently hydrogen or alkyl;

C is a ligand other than A or B; and

X is a counter ion, wherein the number of coordinating atoms is 6) with the exception of $[Ru^{III}(Me_3tacn)(acac)(py)](NO_3)_2$.

The ligand A may be selected from the group consisting of NCS, imidazole, pyrazole, thiazole, oxazole, isoquinoline, substituted pyridyl (eg 3- and/or 4-substituted pyridyl) and isomers thereof.

The ligand A may be selected from the group consisting of imidazole, pyrazole, thiazole, oxazole and isomers thereof.

The ligand A may be or contain a 5- or 6-membered aromatic ligand containing 3 nitrogen heteroatoms. The ligand A is preferably triazine or triazole.

The ligand A may be guanine or adenine.

The ligand A may be substituted by one or more substituents selected from the group consisting of $C_1$-$C_6$ alkyl, $C_1$-$C_6$ alkoxy, $C_2$-$C_6$ alkenyl, $C_2$-$C_6$ alkynyl, halogen, carboxy, amino, $C_{1-6}$-alkylamino, $C_{1-6}$-dialkylamino and hydroxyl.

The ligand A may be substituted by one or more substituents selected from the group consisting of $C_1$-$C_6$ alkyl, $C_1$-$C_6$ alkoxy, $C_2$-$C_6$ alkenyl, $C_2$-$C_6$ alkynyl and halogen. Preferably the ligand A is substituted by one or more substituents selected from the group consisting of methyl, ethyl, propyl, iso-propyl, butyl, t-butyl, methoxy, ethoxy, ethenyl, propenyl, butenyl, ethynyl and propynyl.

The ligand B may be a bi-, tri- or tetra-dentate ligand which may be linear having the formula $R^1RN(C_2H_4NR)_rR^1$ or cyclic having the formula $(RNC_2H_4)_v$, $(RNC_2H_4)_p$ $(RNC_3H_6)_q$ or $[(RNC_2H_4)(RNC_3H_6)]_s$, wherein r is an integer selected from the integers 1-3, v is 3 or 4, each of p and q is an integer independently selected from the integers 1-3 whereby the sum of p and q is 4 and s is 2 or 3.

The ligand B is preferably a tri- or tetra-dentate ligand which is cyclic having the formula $(RNC_2H_4)_v$, wherein v is 3 or 4.

The ligand B may be 1,4,7-trimethyl-1,4,7-triazacyclononane, 1,4,8,11-tetramethyl-1,4,8,11-tetra-azacyclotetradecane, 1,1,4,7,10,10-hexamethyltriethylenetetramine, 1,2-dimethylethylenediamine or 1,1,2,2-tetramethylethylenediamine.

The ligand B may be 1,4,7-trimethyl-1,4,7-triazacyclononane, 1,1,4,7,10,10-hexamethyltriethylenetetramine, 1,2-dimethylethylenediamine or 1,1,2,2-tetramethylethylenediamine.

A preferred ligand B is 1,4,7-trimethyl-1,4,7-triazacyclononane.

The ligand C may be selected from the group consisting of an amine ligand (such as $NH_3$ or $NMe_3$), CO, CN, a halogen, acetylacetonate (acac), 3-bromo-acetylacetonate (Bracac), oxalate, tropolone, 1,4,7-triethylene crown ether and 5-chloro-8-hydroxyquinoline.

A preferred ligand C is acac.

The geometry of the complex of Formula I may be cis or trans when each of ligands A, B and C is bi-dentate.

The oxidation state of the metal in the complex of Formula I may be 2+ or 3+. The oxidation state of the metal in the complex of Formula I is preferably 3+.

The ligands A and B may be selected such that the overall charge on the complex of Formula I is selected from the group consisting of +3, +2, +1, 0, −1, −2 and −3.

The counterion X may be, $F^-$, $Cl^-$, $Br^-$, $I^-$, $NO_3^-$, $NR_4^+$, $NR_4^+$, $PF_6^-$, $CF_3SO_3^-$, $SO_4^{2-}$, $ClO_4^-$, $K^+$, $Na^+$ $Li^+$ or a combination thereof.

In the fourth aspect of the invention, the complex of Formula I may be $[Ru^{III}(1,4,7$-trimethyl-1,4,7-triazacyclononane)(acac)(N-methylimidazole)]$(NO_3)_2$, $[Ru^{III}(1,4,7$-trimethyl-1,4,7-triazacyclononane)(acac)(4-methylpyridine)]$Cl_2$, $[Ru^{III}(1,4,7$-trimethyl-1,4,7-triazacyclononane)(acac)(3-chloropyridine)]$(NO_3)_2$, $[Ru^{III}(1,4,7$-trimethyl-1,4,7-triazacyclononane)(acac)(isonicotinamide)]$(NO_3)_2$, $[Ru^{III}(1,4,7$-trimethyl-1,4,7-triazacyclononane)(acac)pyrazine]$(NO3)_2$, $[Ru^{III}(1,4,7$-trimethyl-1,4,7-triazacyclononane)(acac)(4-methoxypyridine)]$(NO_3)_2$, $Ru^{III}(1,4,7$-tri methyl-1,4,7-triazacyclononane)(acac)(4-dimethylaminopyridine))$(NO_3)_2$, $[Ru^{III}(1,4,7$-trimethyl-1,4,7-triazacyclononane)(acac)(4-t-butyl-pyridine)]$(NO_3)_2$, $[Ru^{III}(1,4,7$-trimethyl-1,4,7-triazacyclononane)(acac)(isoquinoline)]$(NO_3)_2$, $[Ru^{III}(1,4,7$-trimethyl-1,4,7-triazacyclononane)(tropolone)(pyridine)]$(NO_3)_2$, $[Ru^{III}(1,4,7$-trimethyl-1,4,7-triazacyclononane)(tropolone)(4-t-butyl-pyridine)]$(NO_3)_2$, $[Ru^{III}(1,4,7$-trimethyl-1,4,7-triazacyclononane)(acac)(3,4-dimethylpyridine)]$(CF_3SO_3)_2$ or $[Ru^{III}(1,4,7$-trimethyl-1,4,7-triazacyclononane)(acac)(3-hydroxypyridine)]$(NO_3)_2$.

In the fourth aspect of the invention, the complex of Formula I may be $[Ru^{III}(1,4,7$-trimethyl-1,4,7-triazacyclononane)(acac)(N-methylimidazole)]$(PF_6)_2$ or $[Ru^{III}(1,4,7$-trimethyl-1,4,7-triazacyclononane)(acac)(N-methylimidazole)]$(NO_3)_2$.

In the complex of Formula I, the metal may be selected to be ruthenium or osmium as desired. A person skilled in the art will appreciate that substituting Ru with Os will change the working potential of a complex by around +400 mV to +600 mV and that the working potential may be further fine tuned (in the reverse direction if necessary) by altering the ligands around the metal centre until the mediator reaches a working potential of −300 mV to +300 mV vs Ag/AgCl.

The term "alkyl" used herein includes linear or branched, saturated aliphatic hydrocarbons. Examples of alkyl groups include methyl, ethyl, n-propyl, isopropyl, n-butyl, tert-butyl and cyclopentyl. Unless otherwise noted, the term "alkyl" includes alkyl and cycloalkyl groups.

The term "alkoxy" used herein describes an alkyl group joined to the remainder of the structure by an oxygen atom. Examples of alkoxy groups include methoxy, ethoxy, n-propoxy, isopropoxy, butoxy, tert-butoxy and cyclopentoxy. Unless otherwise noted, the term "alkoxy" includes alkoxy and cycloalkoxy groups.

The term "alkenyl" used herein describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl and cyclopentenyl. Unless otherwise noted, the term "alkenyl" includes alkenyl and cycloalkenyl groups.

The term "acac" refers to the acetylacetonate anion which is the conjugate base of 2,4-pentanedione.

A "substituted" functional group (eg substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —$NH_2$, alkylamino, dialkylamino, trialkylammonium, alkanoylamino, dialkanoylamino, arylcarboxamido, hydrazino, alkylthio, alkenyl and reactive groups.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amino, acrylamide, thiol, acyl azide, acyl halide, hydrazine, hydroxylamine, alkyl halide, imidazole, pyridine, phenol, alkyl, sulfonate, halotriazine, imido ester, maleimide, hydrazide, hydroxy, and photo-reactive azido aryl groups. As understood in the art, activated esters generally include esters of succinimidyl, benzotriazolyl or aryl substituted by electron withdrawing groups such as sulfo, nitro, cyano, or halo.

A "biological fluid" is a bodily fluid or bodily fluid derivative in which an analyte can be measured (eg blood, interstitial fluid, plasma, dermal fluid, sweat, saliva and tears).

An "electrochemical sensor" is a device configured to detect the presence of or measure the concentration or amount of an analyte in a sample via electrochemical oxidation or reduction reactions. These reactions typically can be transduced to an electrical signal that can be correlated to an amount or concentration of analyte.

A "redox mediator" is an electron transfer agent for carrying electrons between an analyte or an analyte-reduced or analyte-oxidized enzyme and an electrode directly or via one or more additional electron transfer agents.

The electrochemical cell may be a two-electrode, a three-electrode, a four-electrode or a multiple-electrode system. A two-electrode system comprises a working electrode and a pseudo reference electrode. A three-electrode system comprises a working electrode, an ideal or pseudo reference electrode and a separate counter electrode. As used herein, a pseudo reference electrode is an electrode that is capable of providing a substantially stable reference potential. In a two-electrode system, the pseudo reference electrode also acts as the counter electrode in this case a current passes through it without substantially perturbing the reference potential. As used herein, an ideal reference electrode is an ideal non-polarisable electrode through which no current passes.

The term "measurable signal" means a signal which can be readily measured (such as electrode potential, fluorescence, spectroscopic absorption, luminescence, light scattering, NMR, IR, mass spectroscopy, heat change or a piezo-electric change).

The term "biochemical analyte" includes any measurable chemical or biochemical substance that may be present in a biological fluid (such as an enzyme, an antibody, a DNA sequence or a microorganism).

In accordance with the present invention, monodentate and bidentate have their generally accepted meaning in the art ie a monodentate ligand is a chemical moiety or group that has one potential coordinating atom. A multidentate ligand is a chemical moiety or group that has more than one potential coordinating atom. The number of potential coordinating atoms is indicated by the prefix (eg bi or tri).

Figure 2:
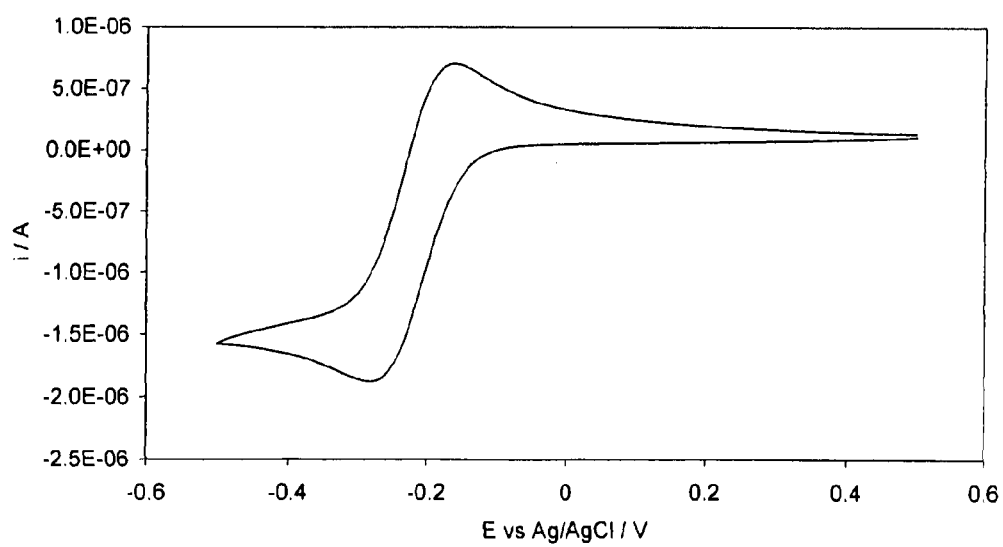
Figure 3:
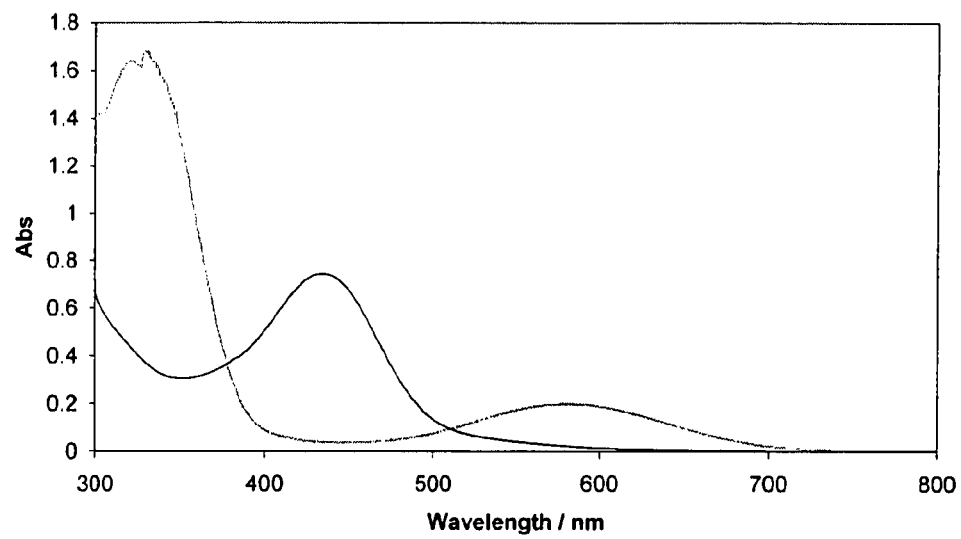
Figure 4:
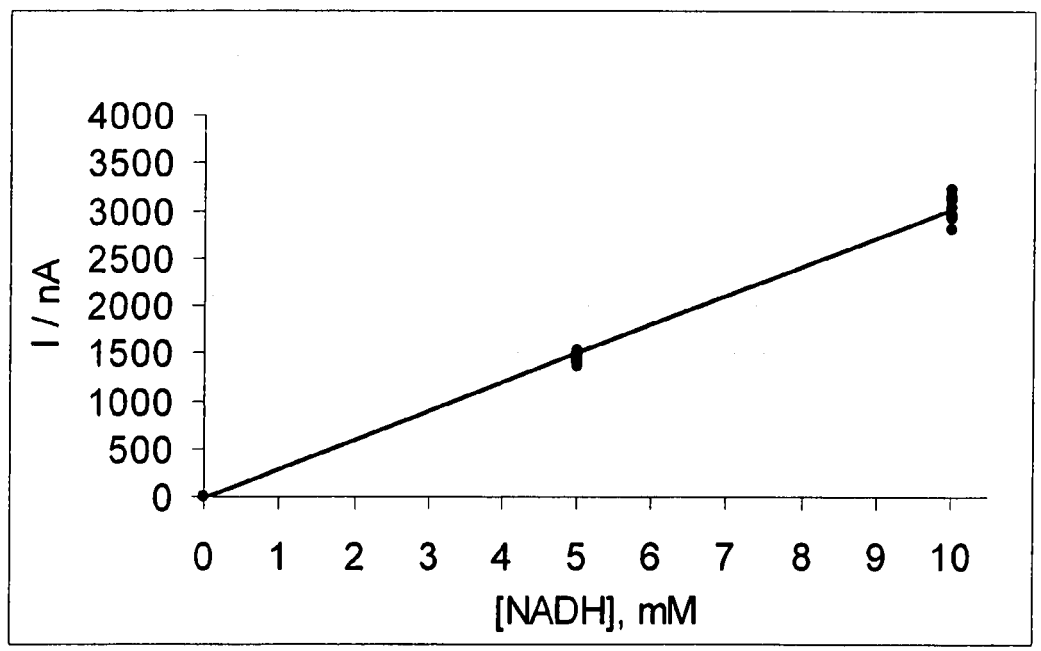
Figure 5:
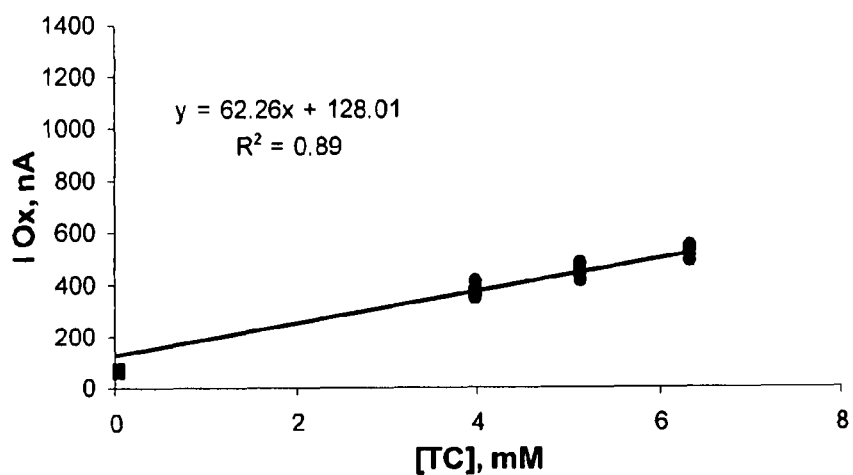
Figure 6:
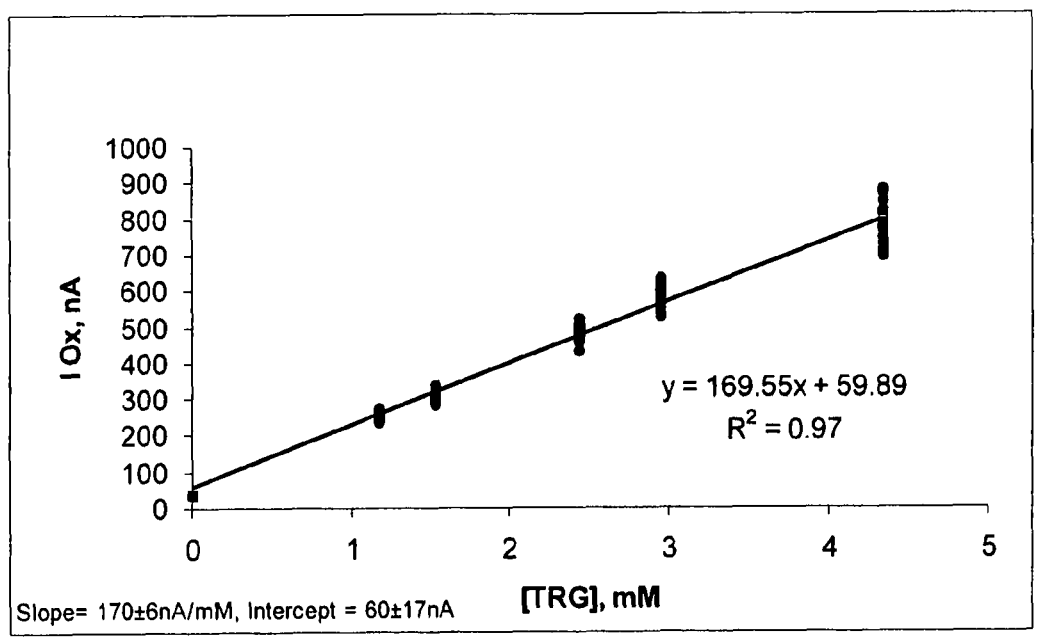
Figure 7:
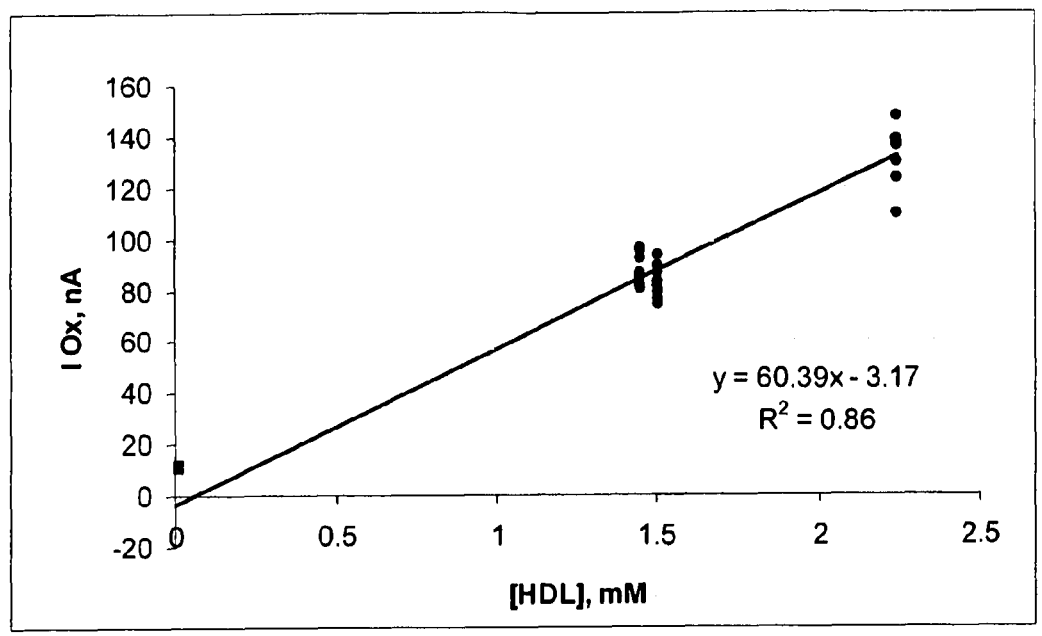
Figure 8:
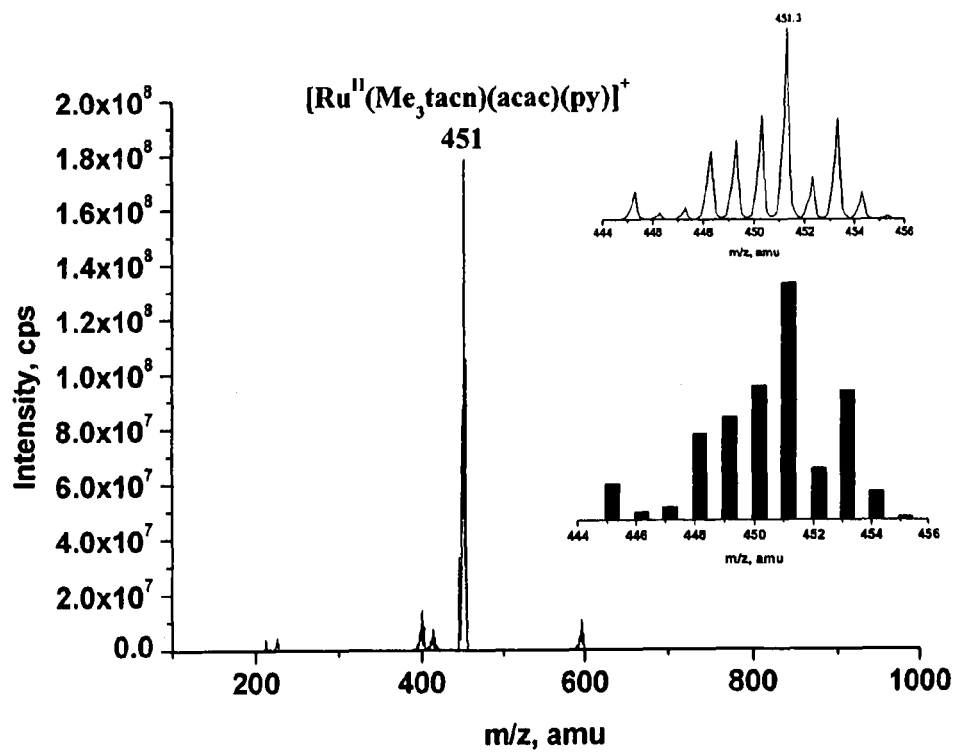
Figure 9:
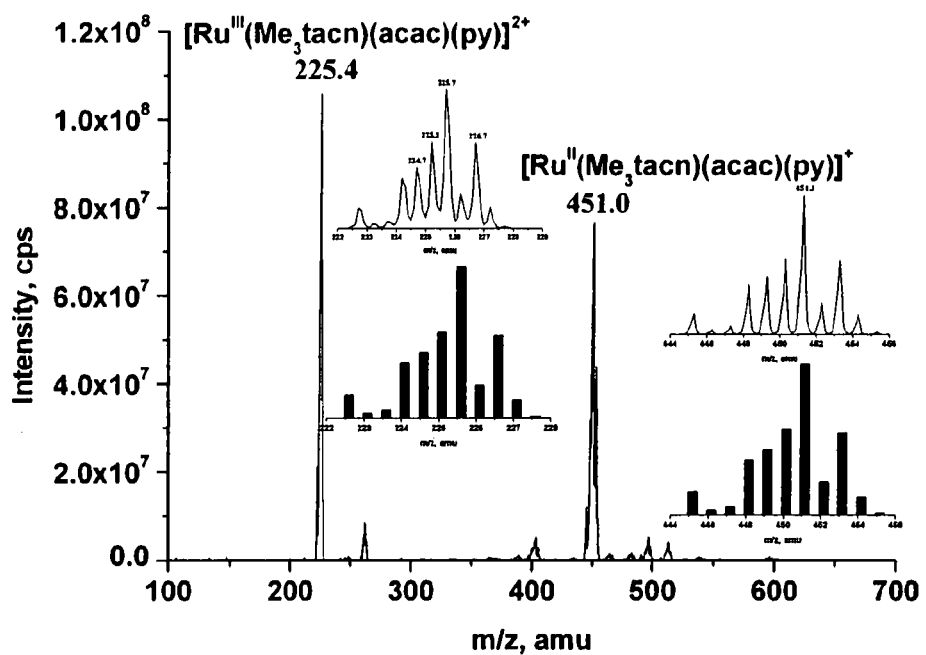
Figure 10:
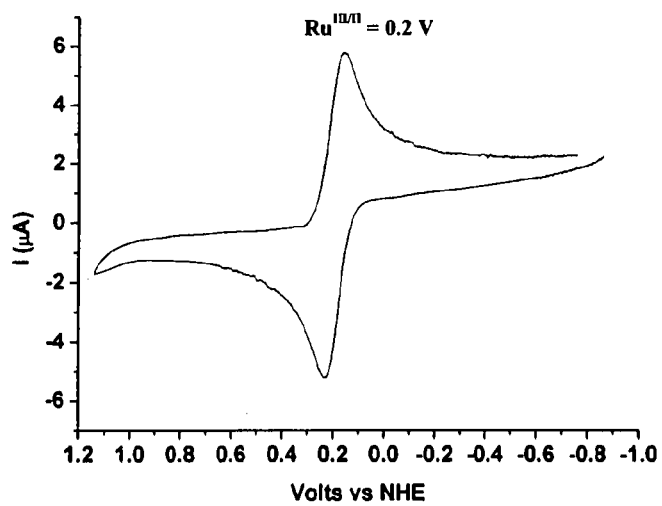
Figure 11:
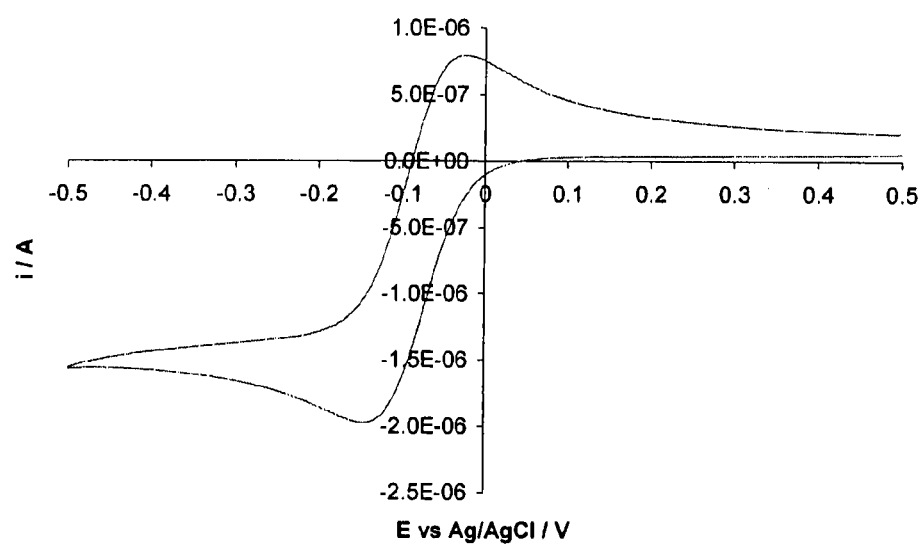
Figure 12:
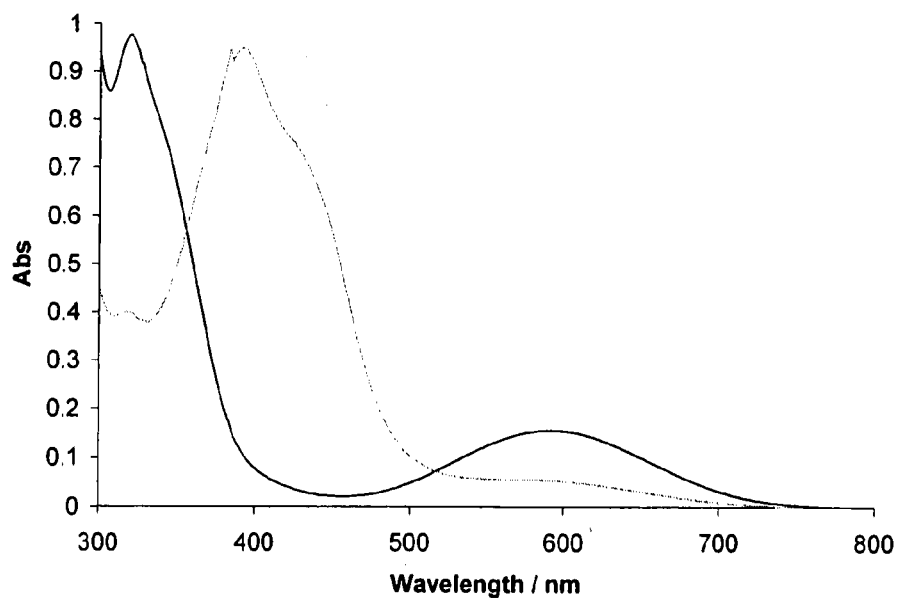
Figure 13:
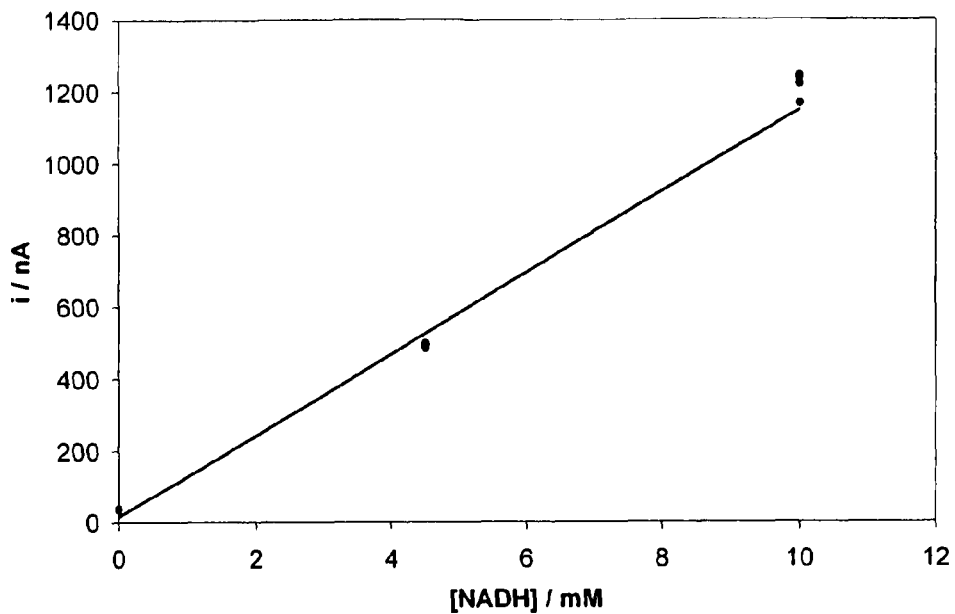
Figure 14:
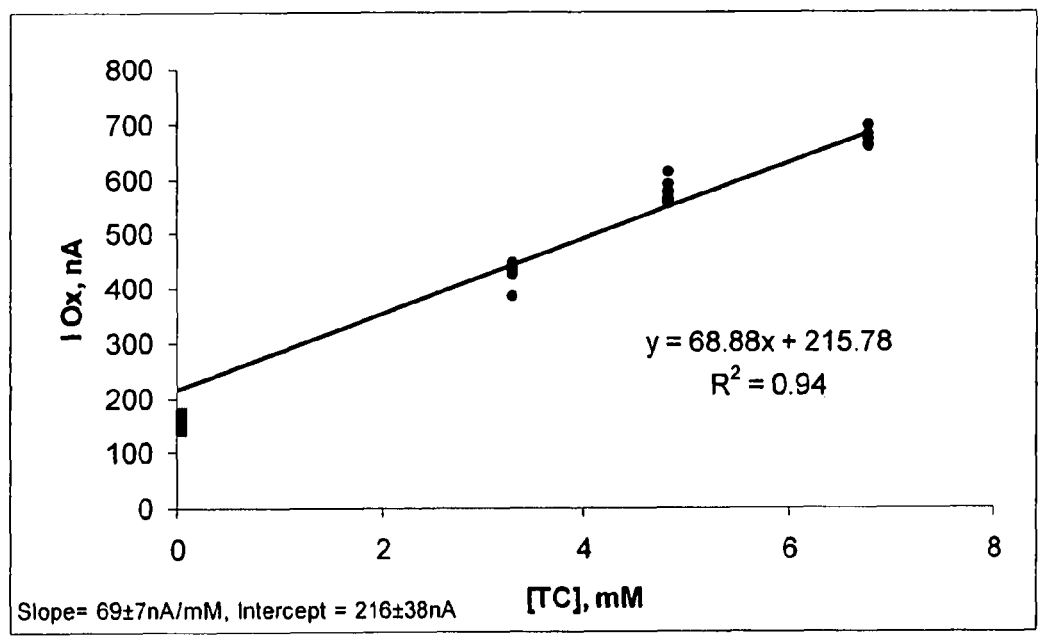
Figure 15:
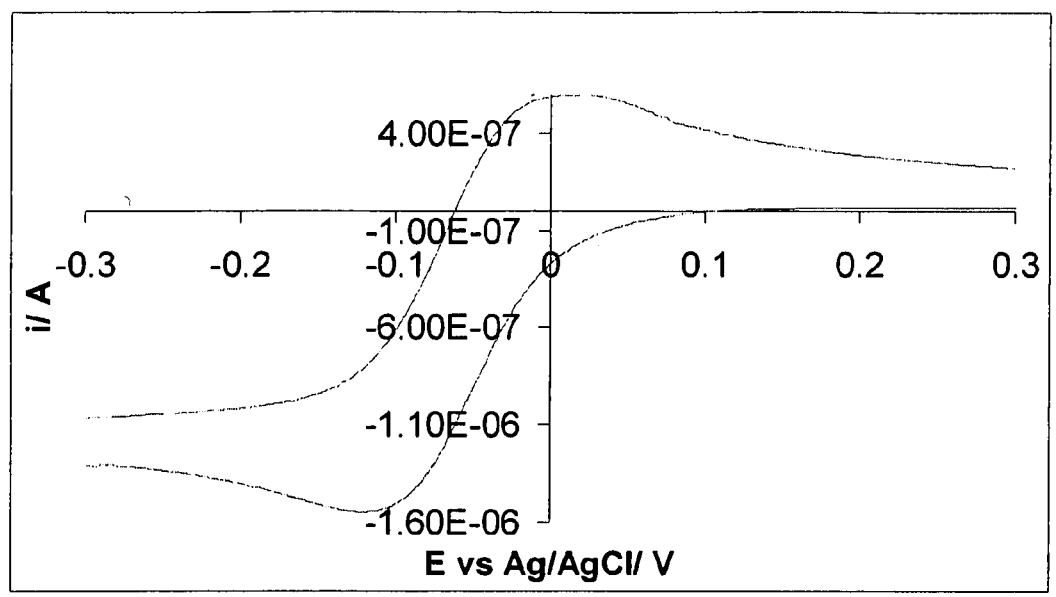
Figure 16:
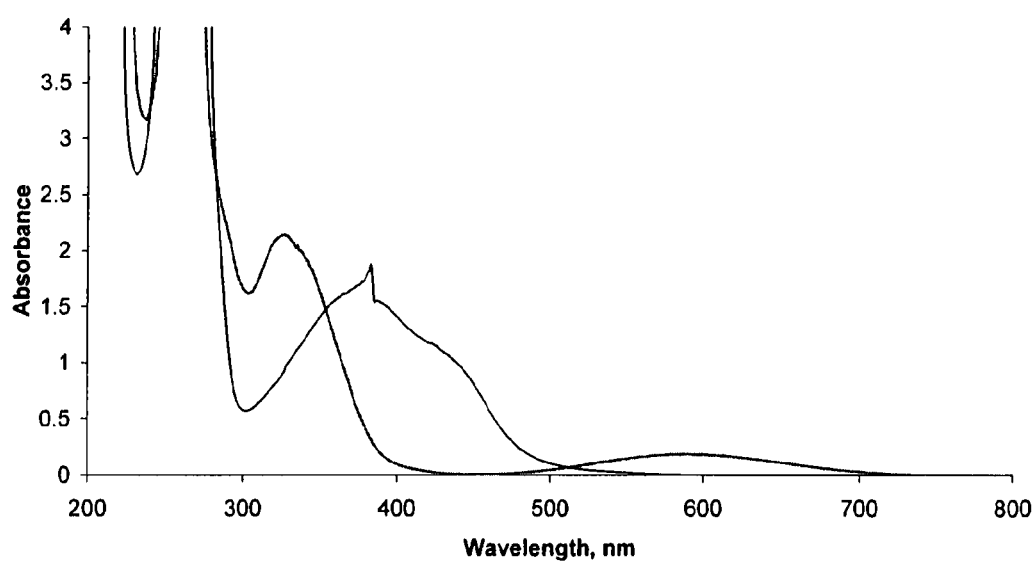
Figure 17:
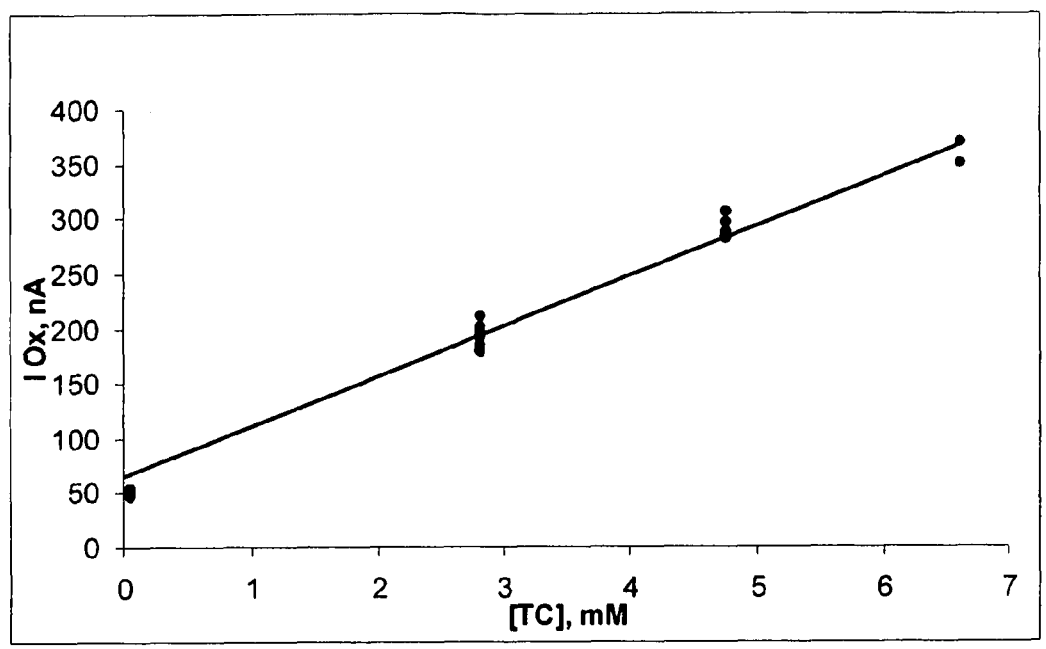
Figure 18:
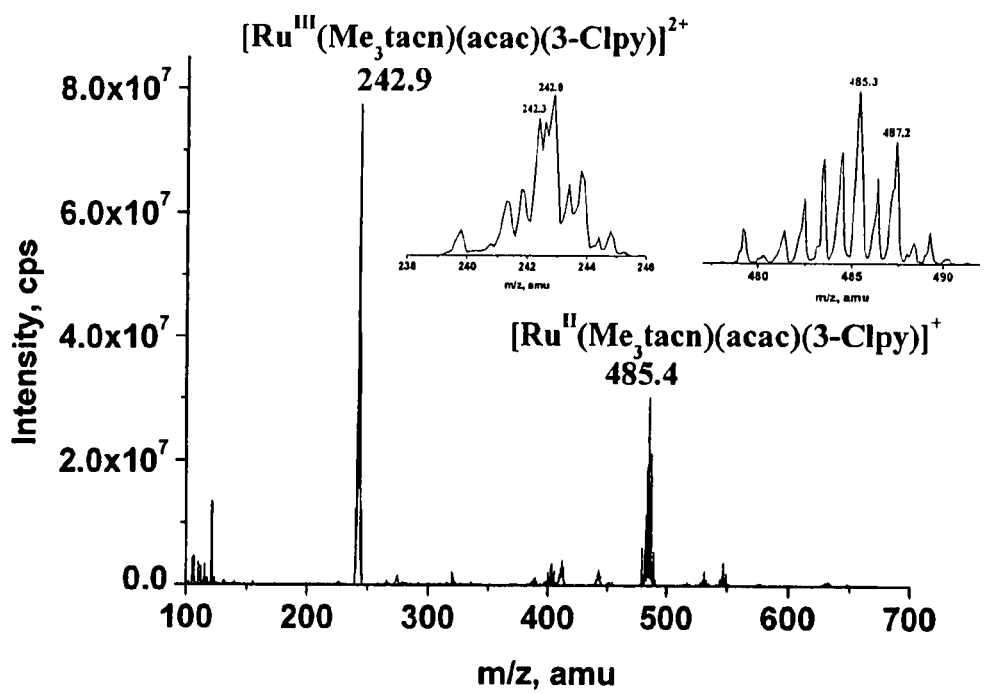
Figure 19:
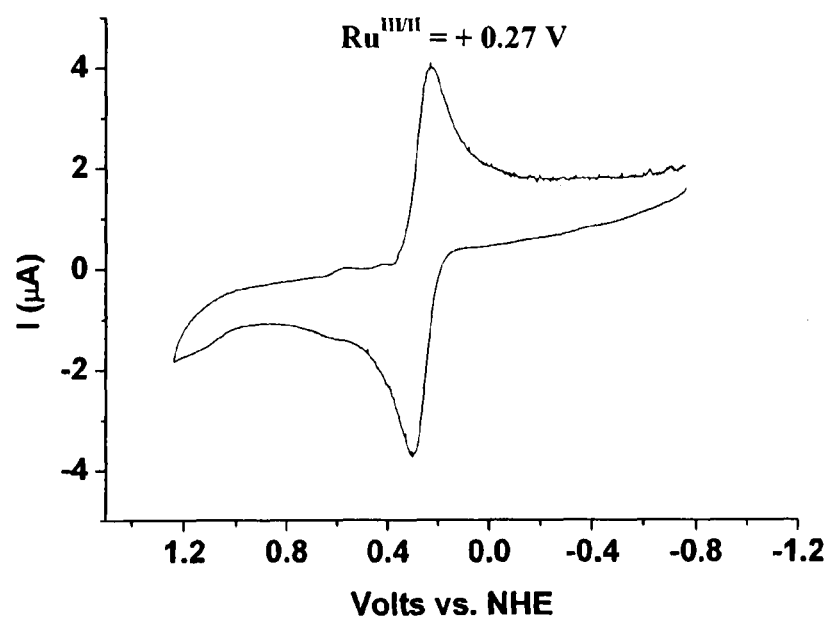
Figure 20:
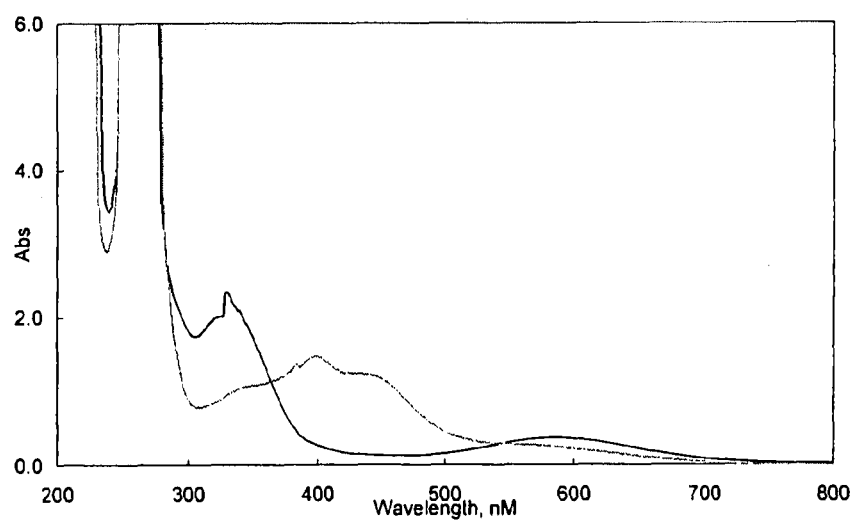
Figure 21:
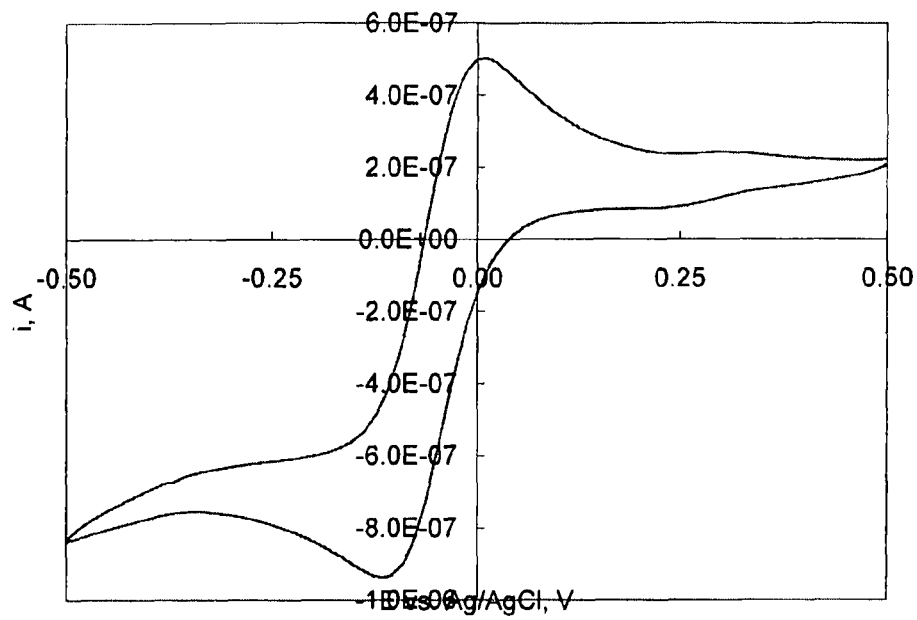
Figure 22:
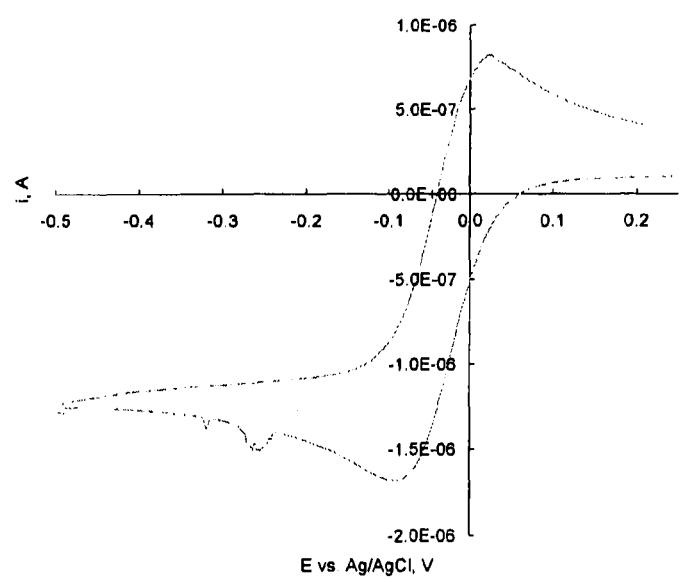
Figure 23:
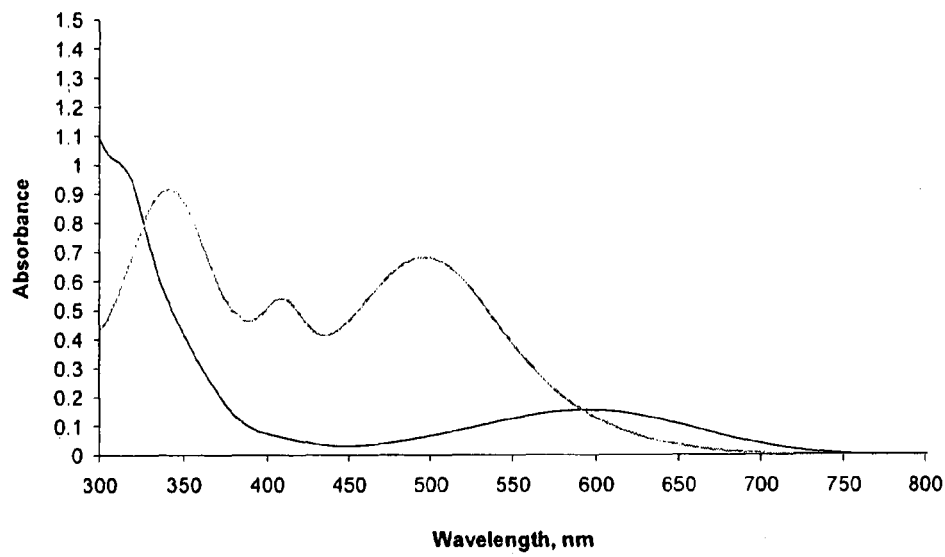
Figure 24:
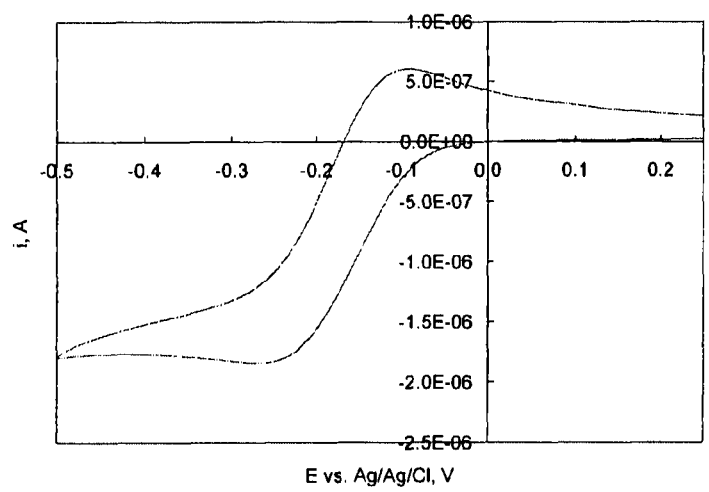
Figure 25:
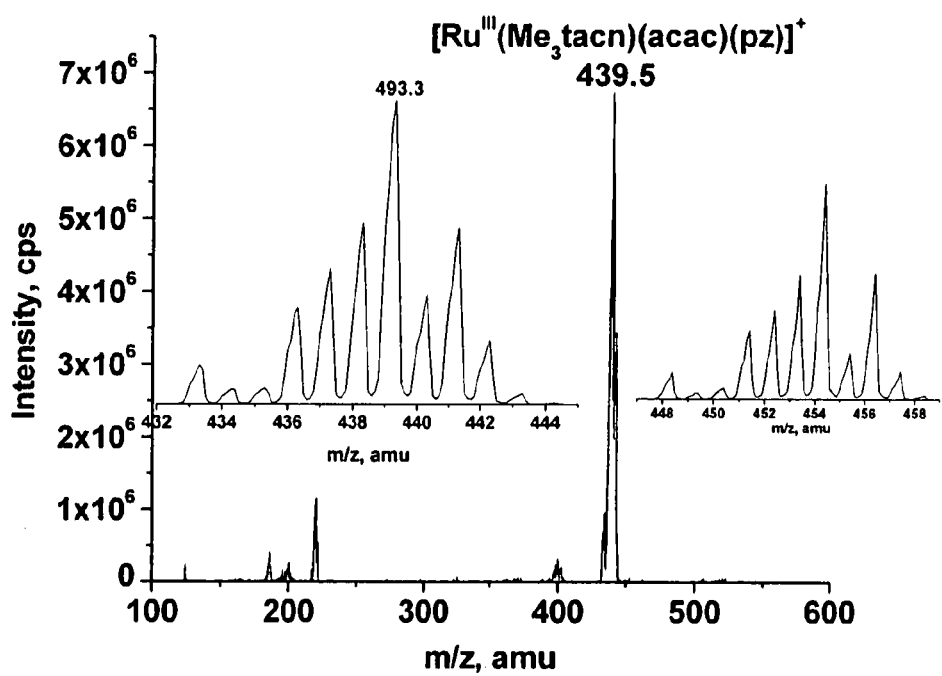
Figure 26:
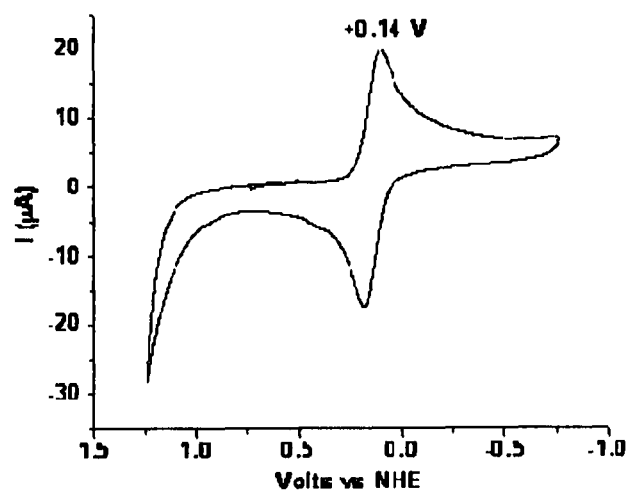
Figure 27:
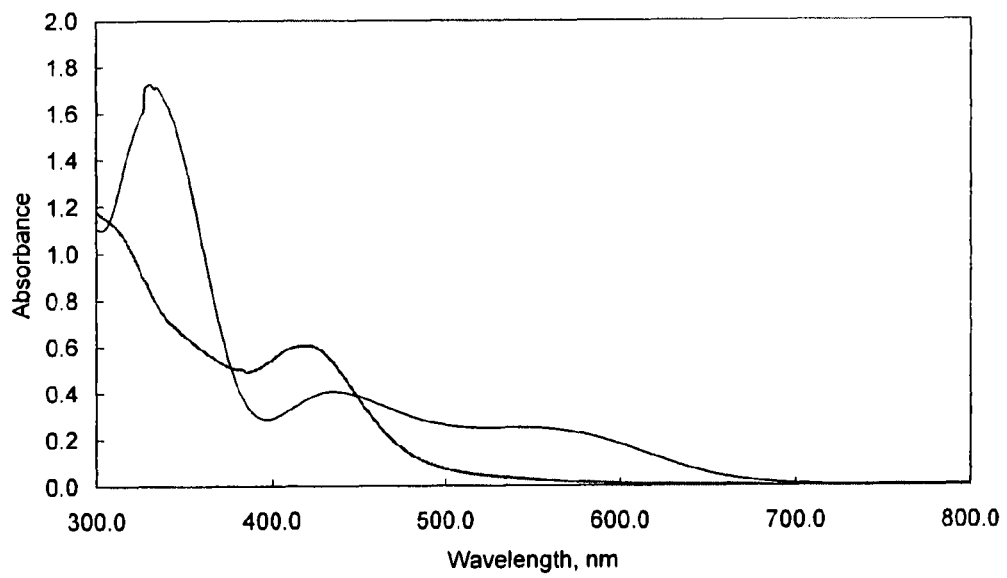
Figure 28:
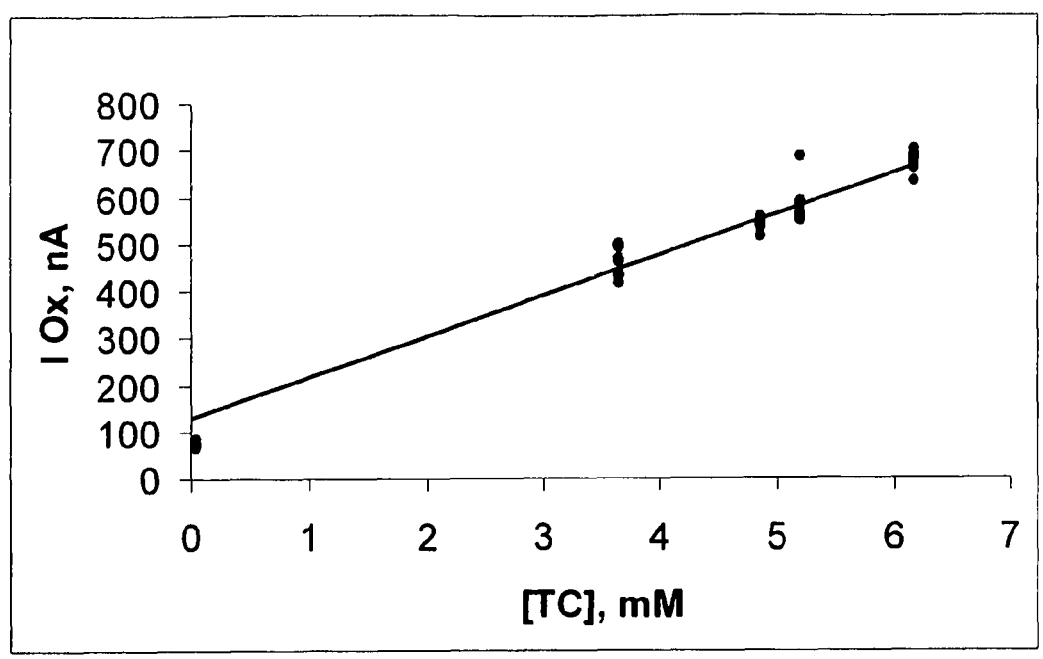
Figure 29:
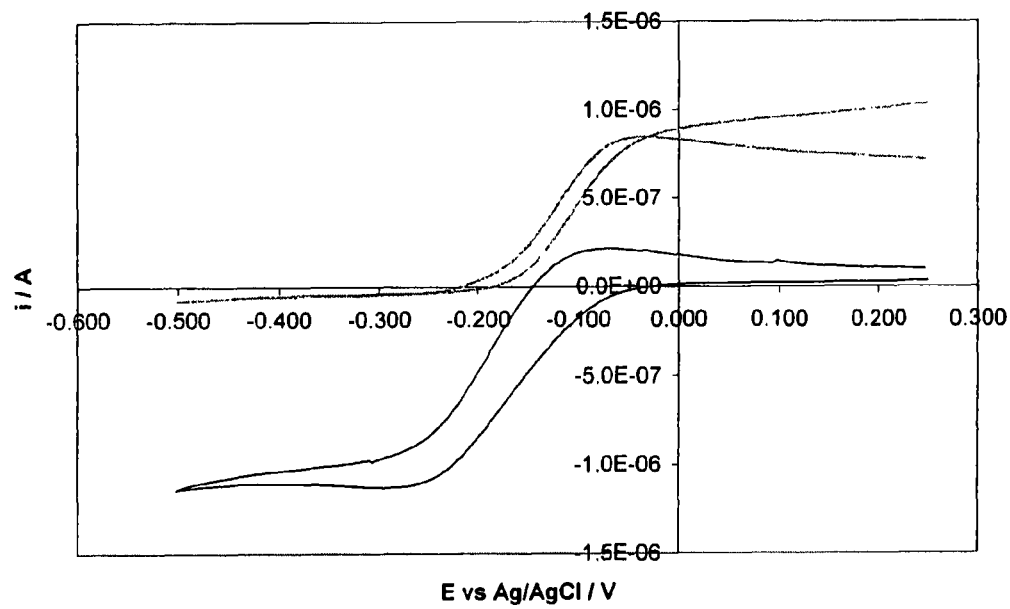
Figure 30:
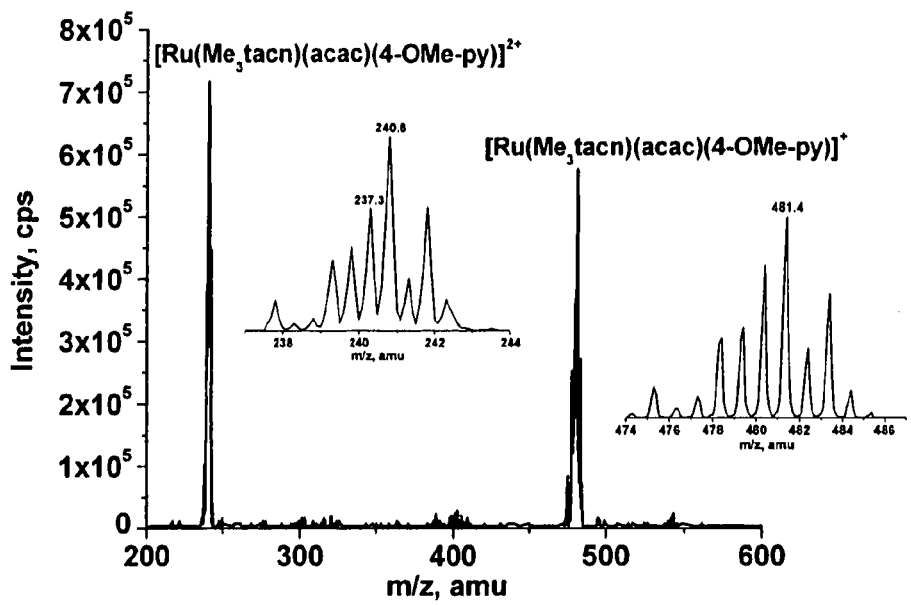
Figure 31:
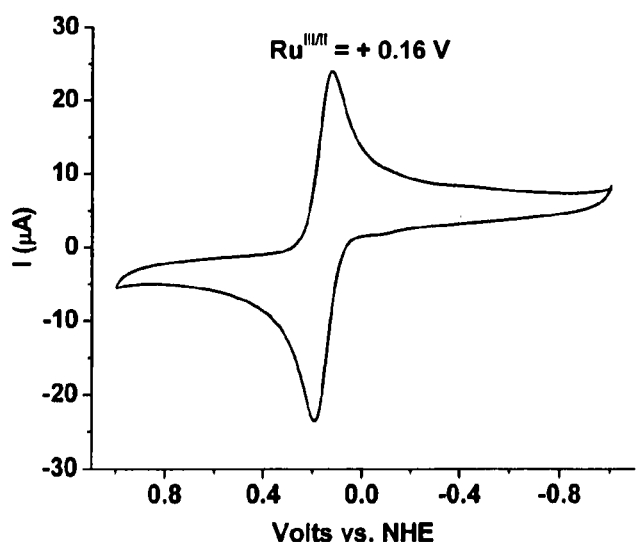
Figure 32:
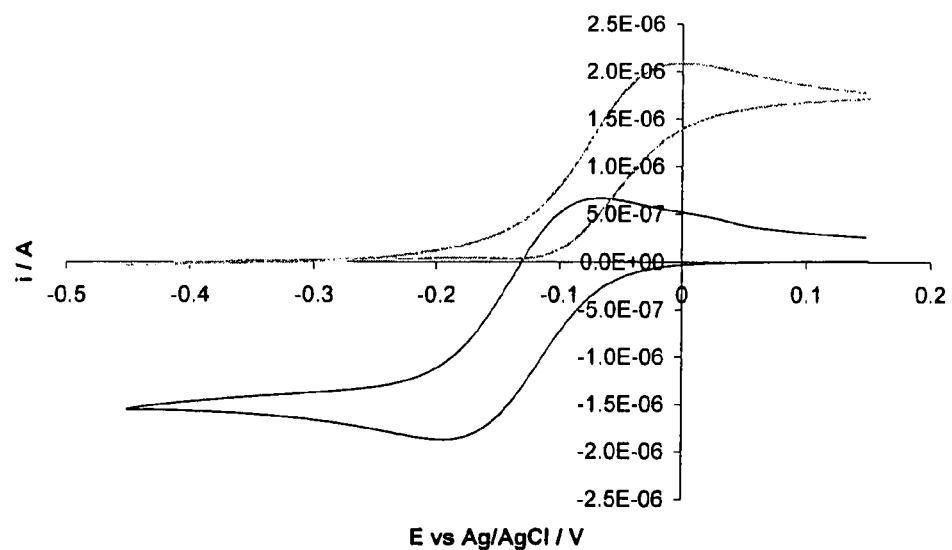
Figure 33:
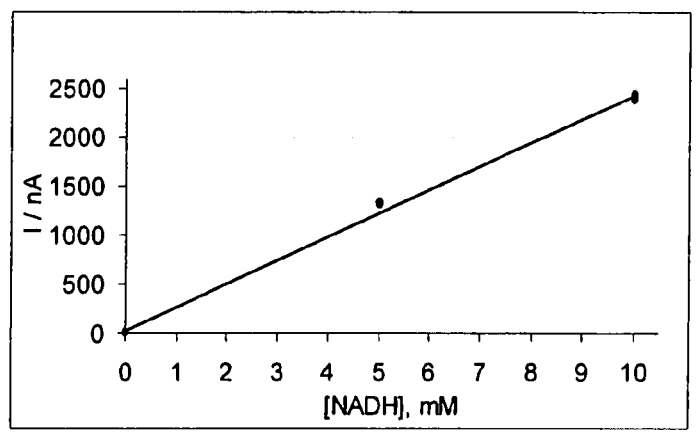
Figure 34:
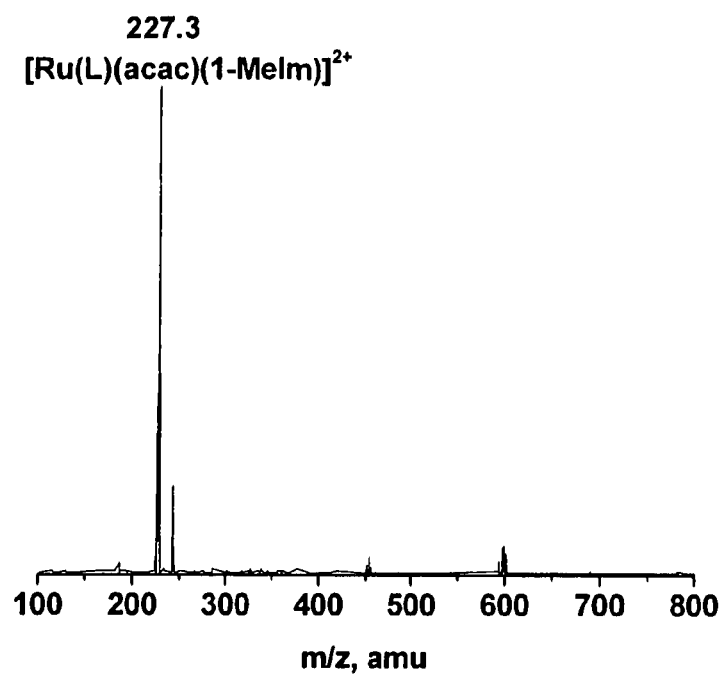
Figure 35:
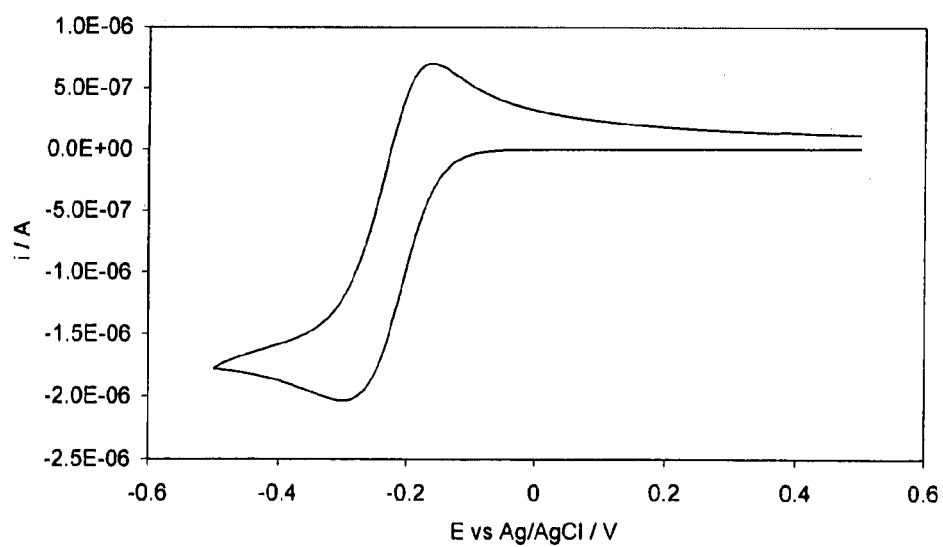
Figure 36:
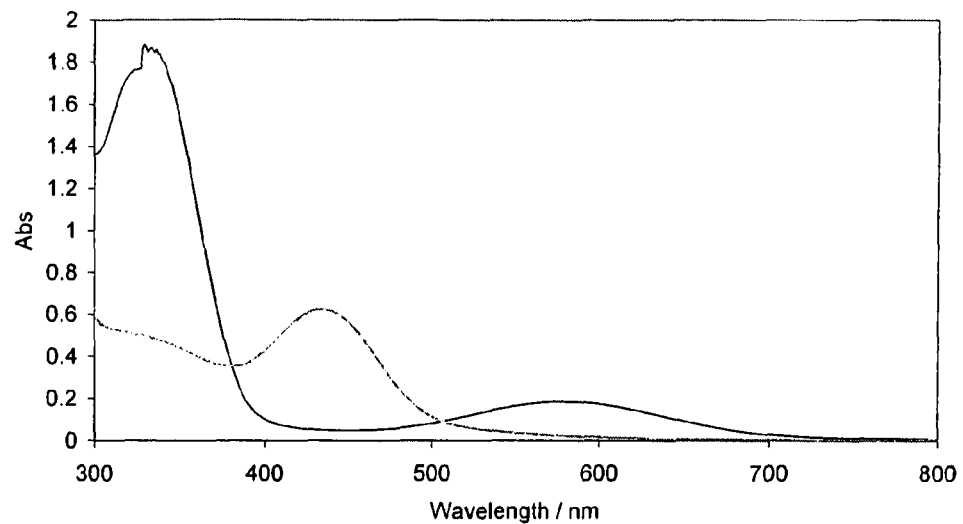
Figure 37:
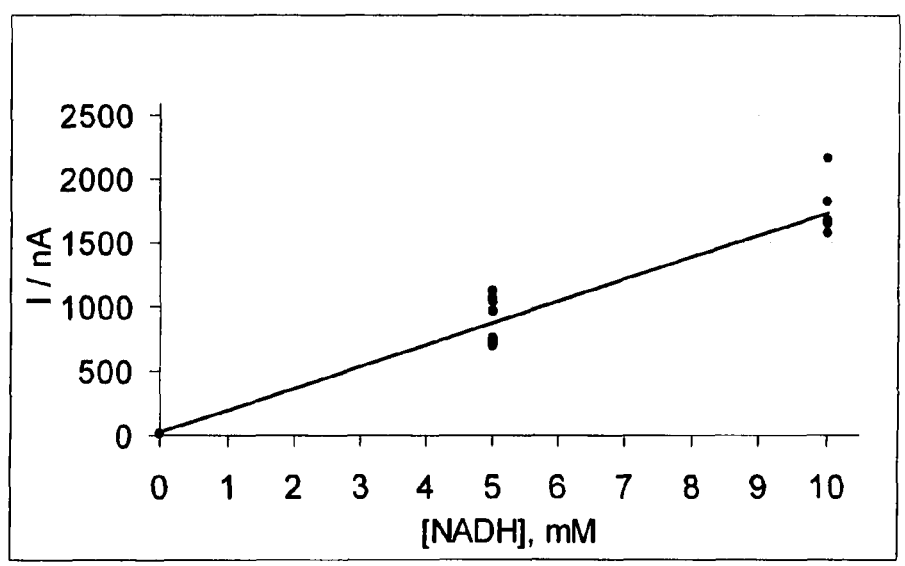
Figure 38:
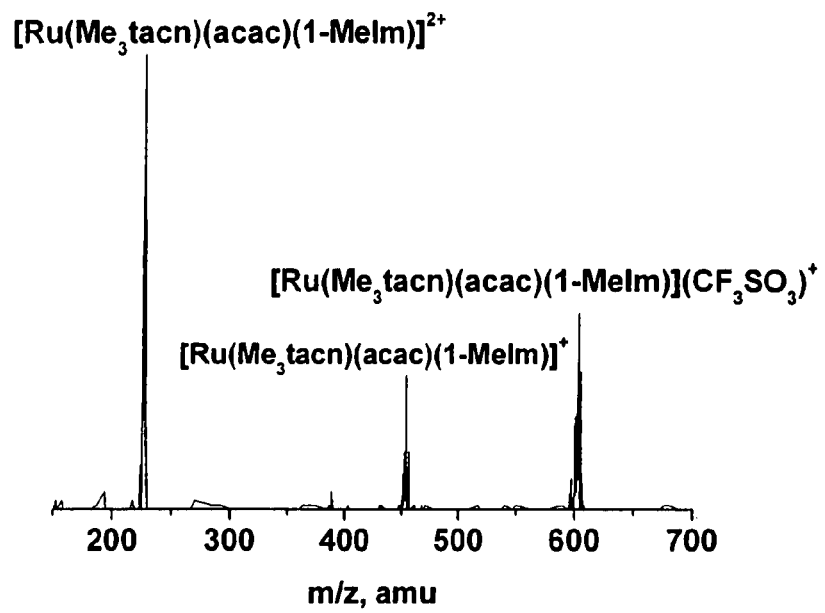
Figure 39:
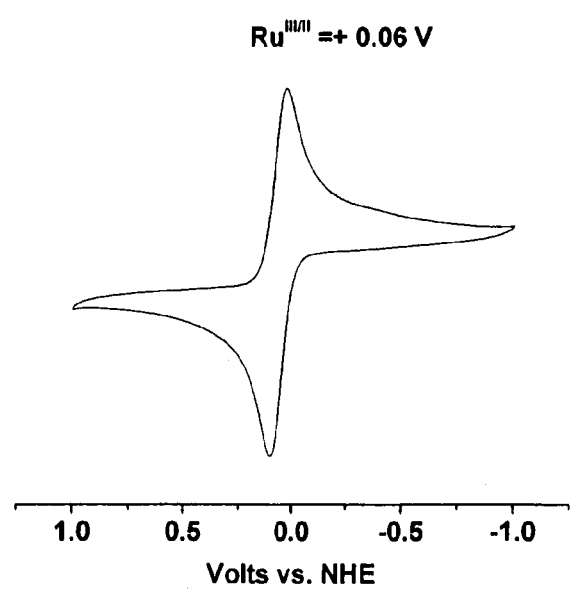
Figure 39A:
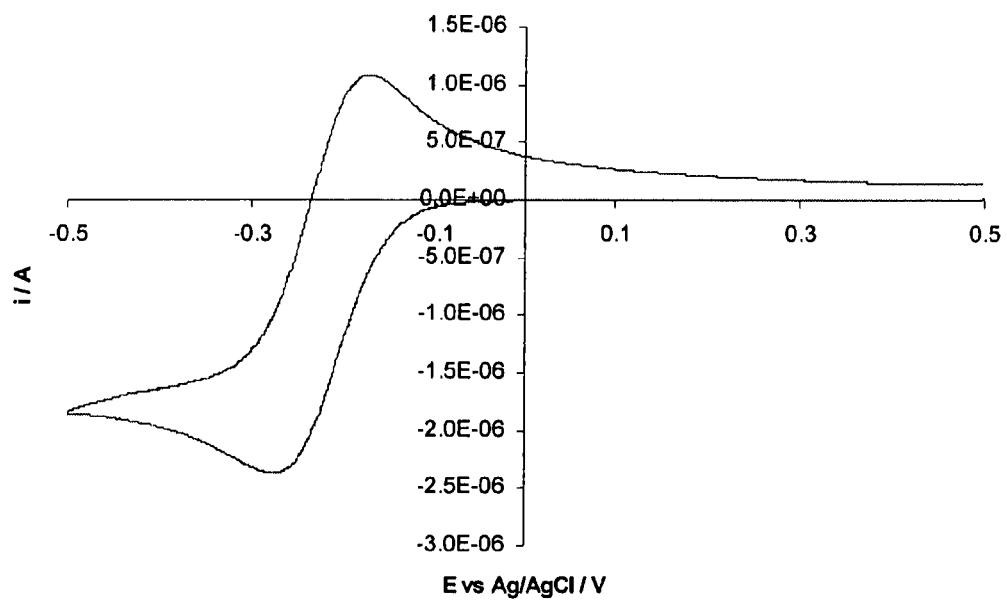
Figure 39B:
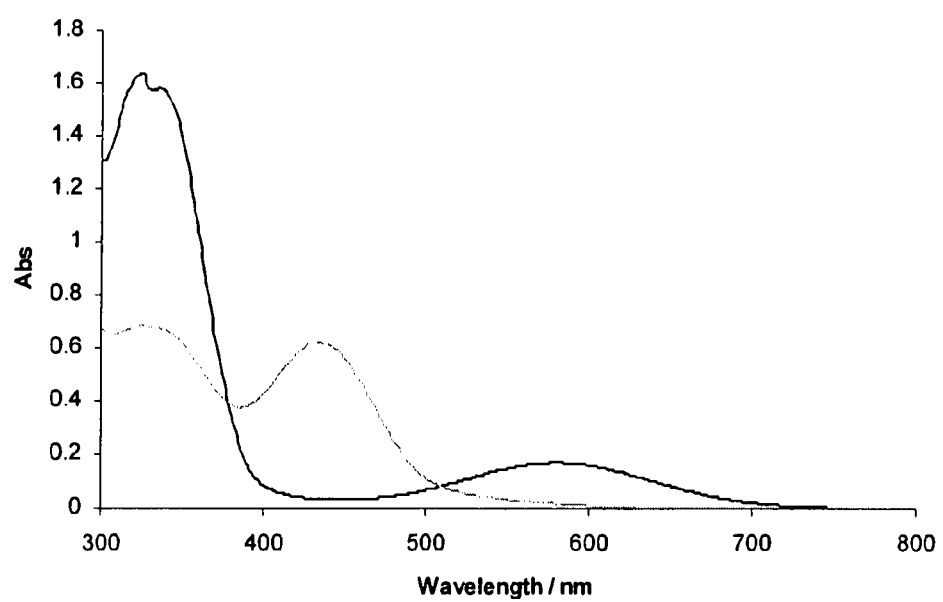
Figure 39C:
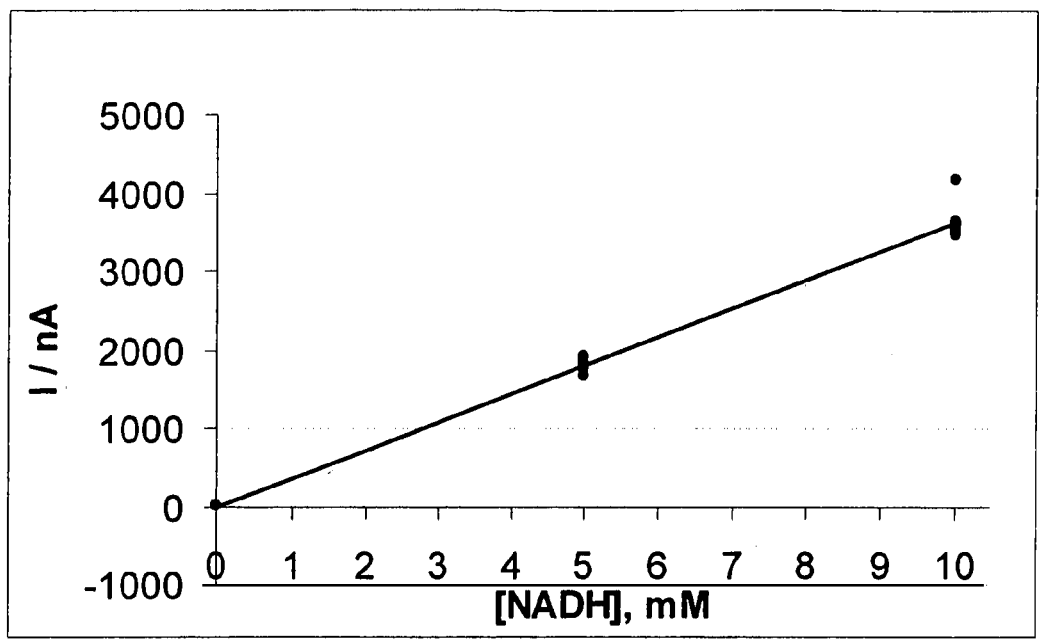
Figure 40:
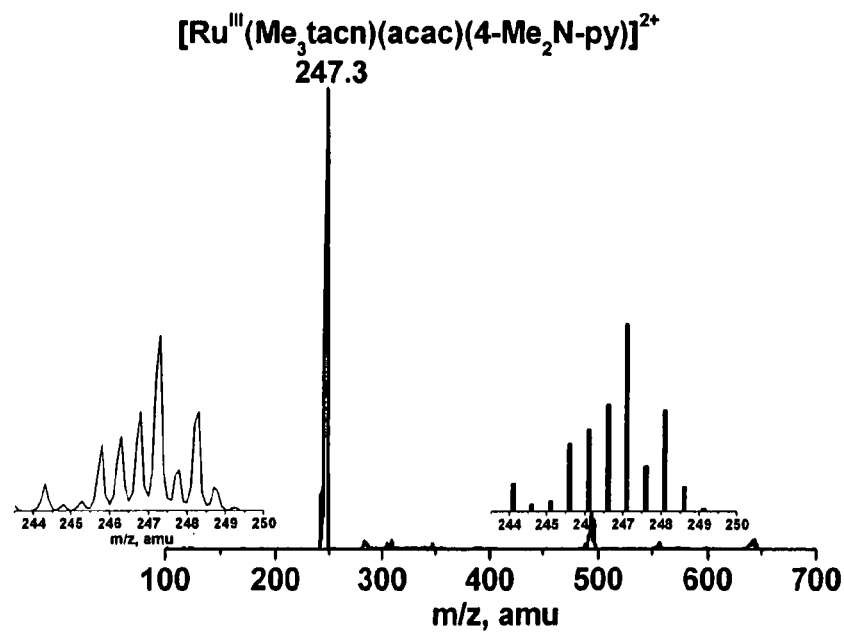
Figure 41:
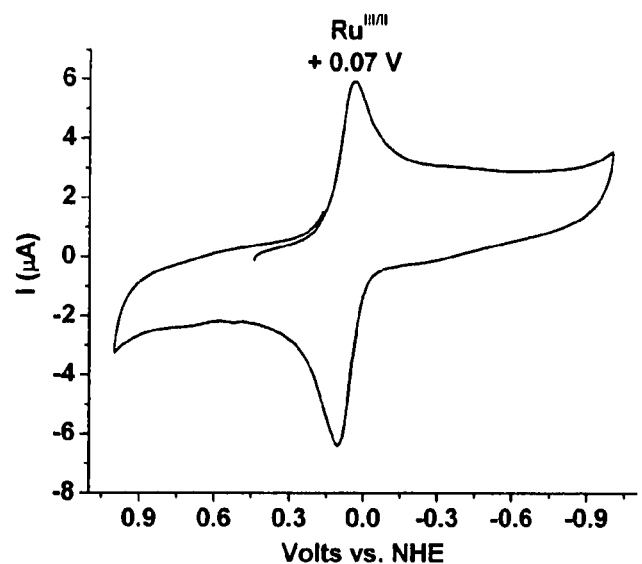
Figure 42:
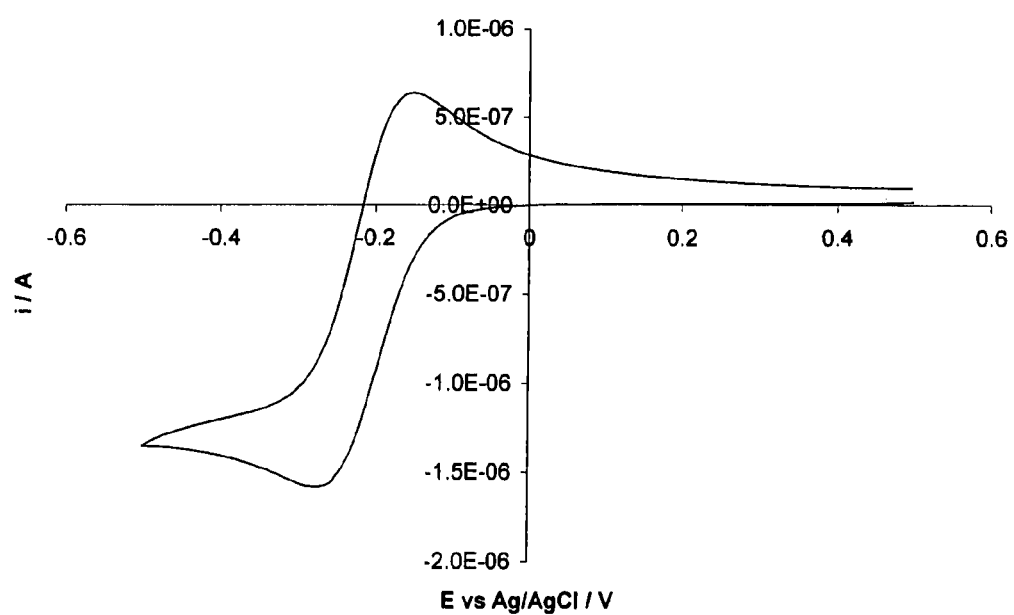
Figure 43:
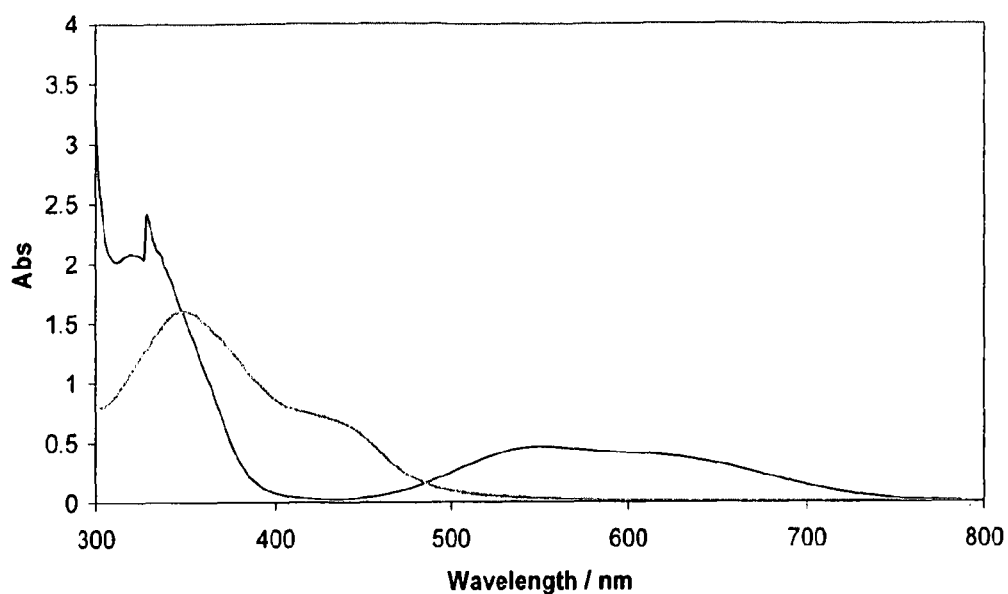
Figure 44:
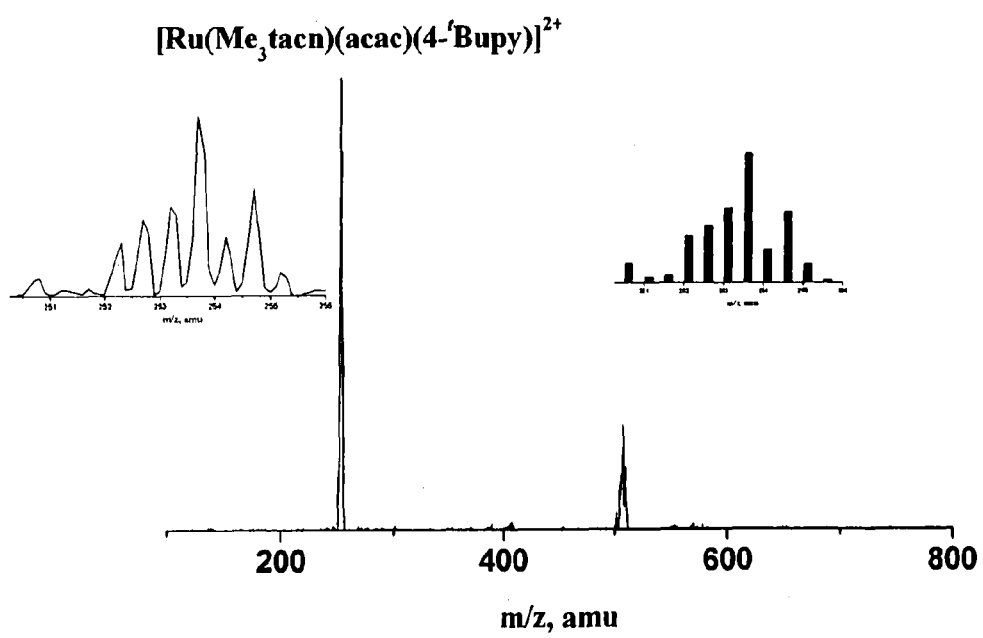
Figure 45:
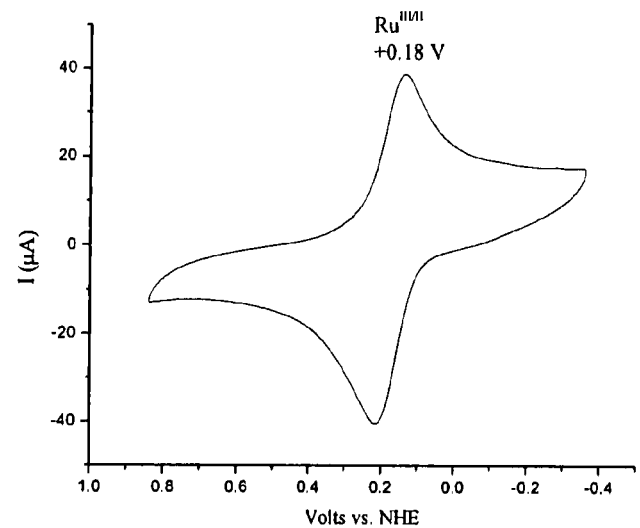
Figure 46:
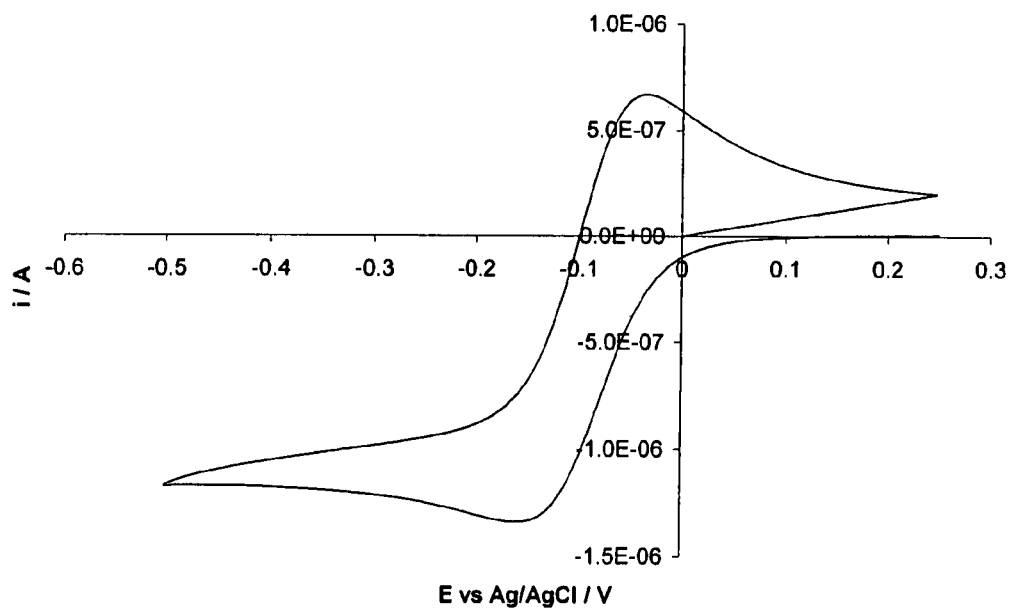
Figure 47:
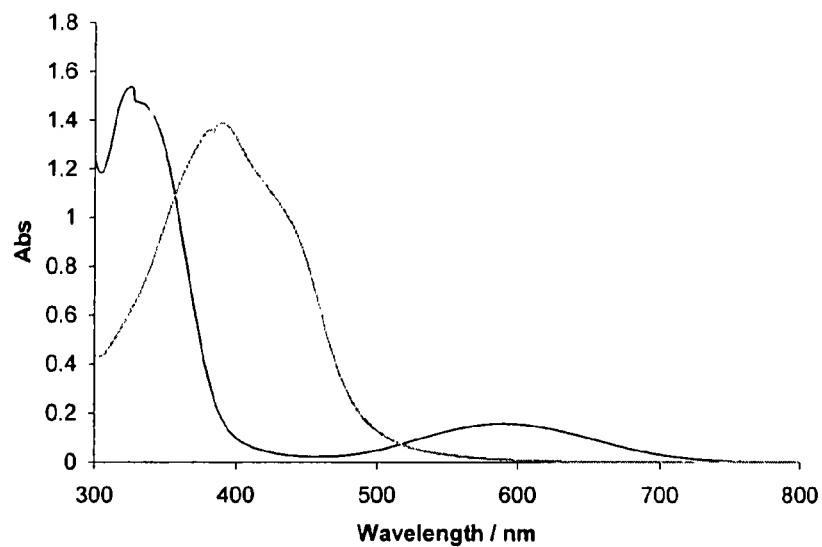
Figure 48:
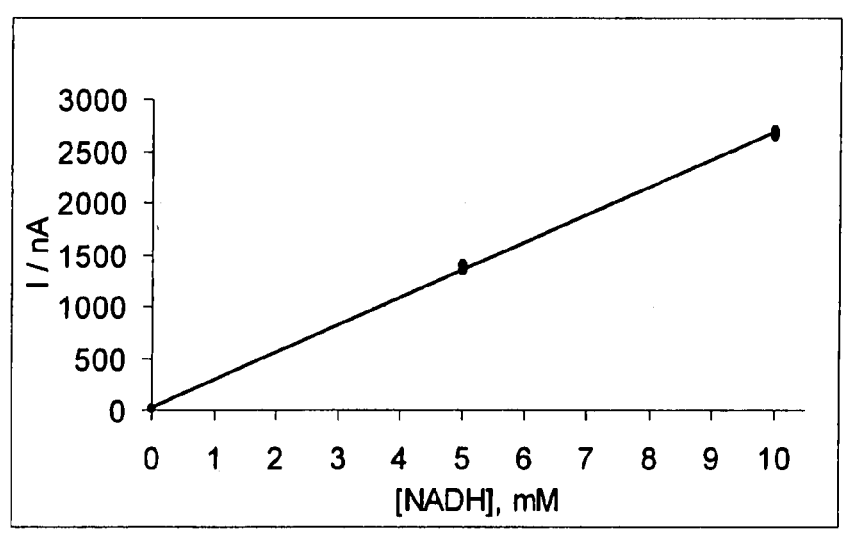
Figure 49:
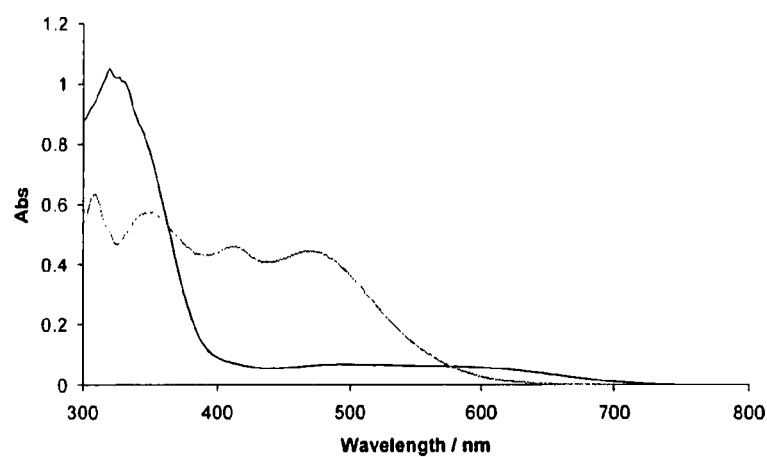
Figure 50:
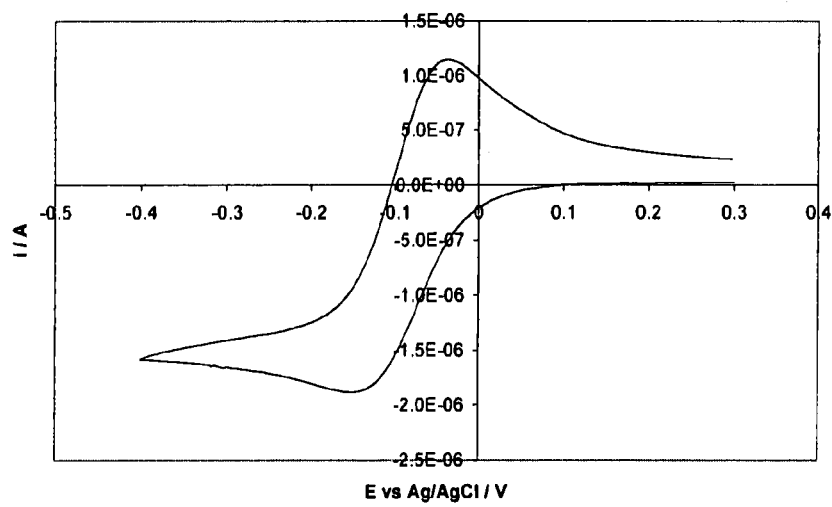
Figure 51:
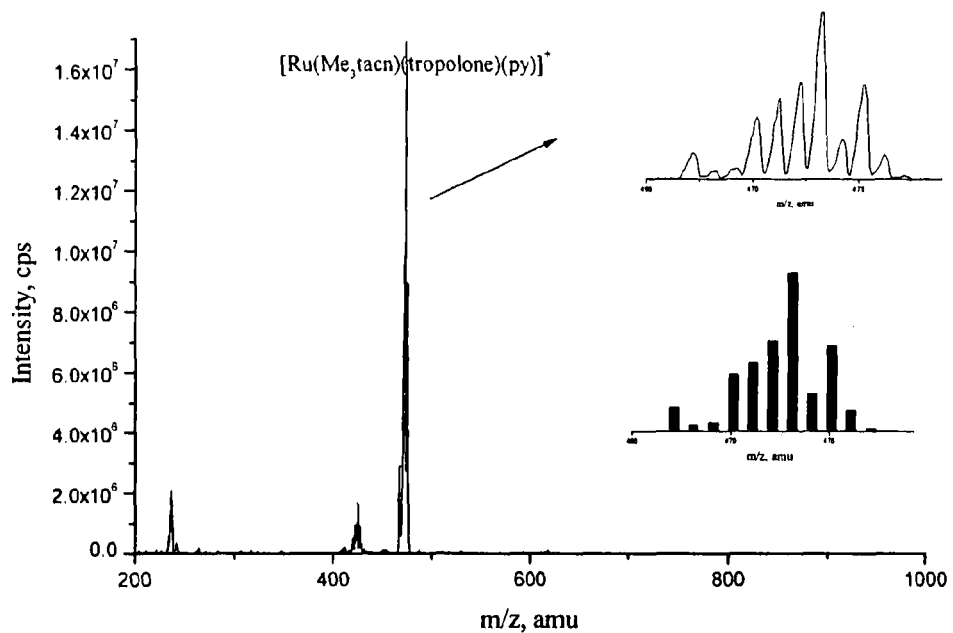
Figure 52:
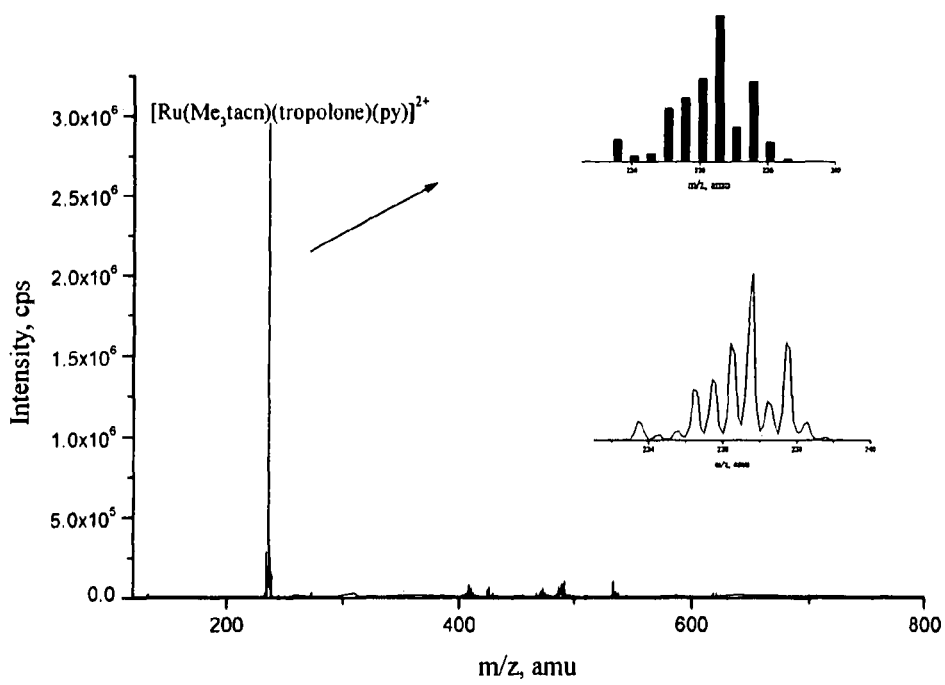
Figure 53:
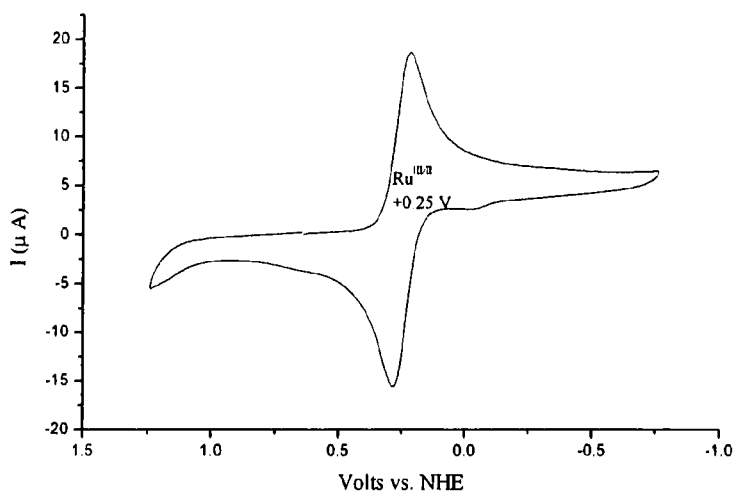
Figure 54:
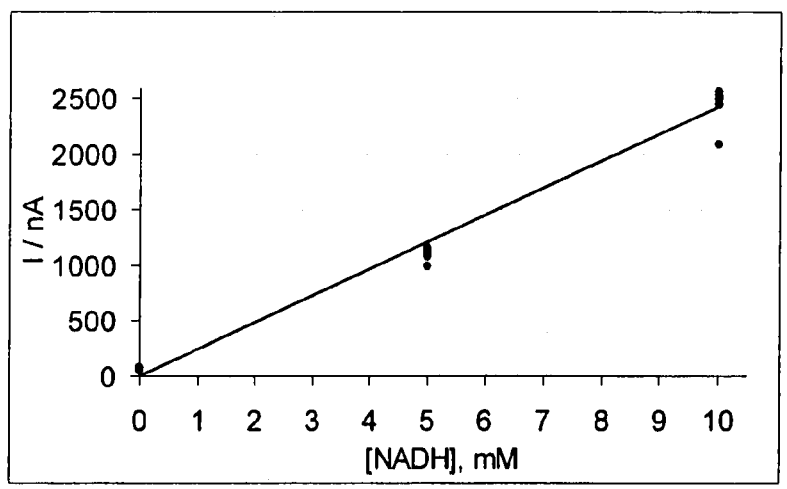
Figure 55:
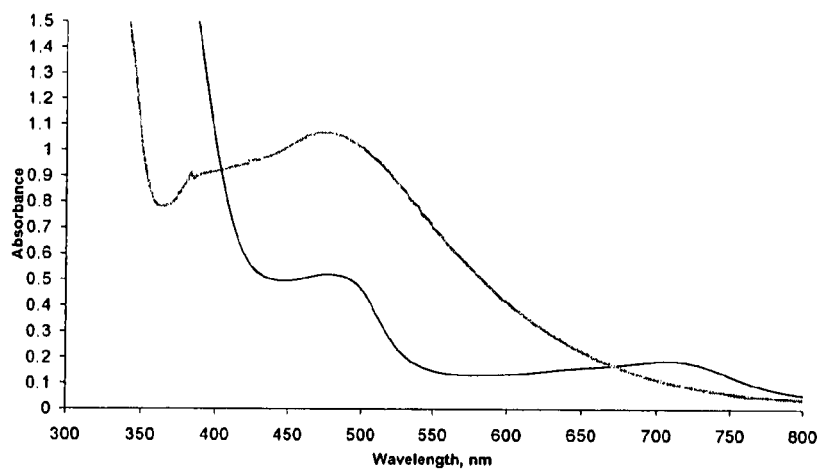
Figure 56:
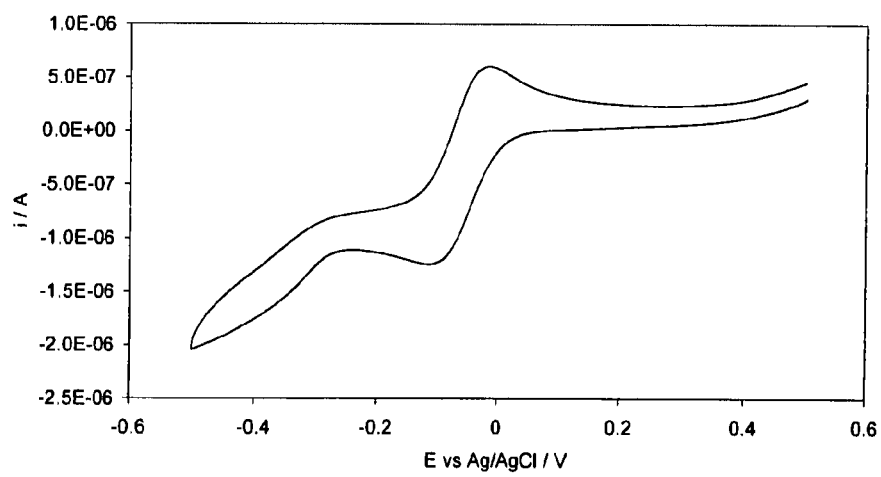
Figure 57:
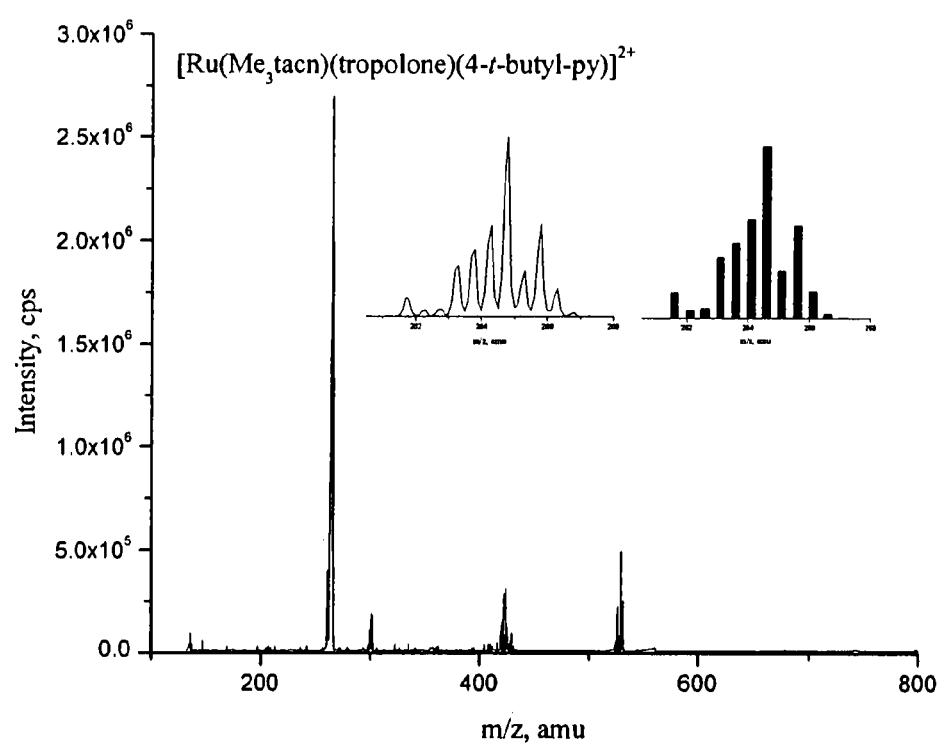
Figure 58:
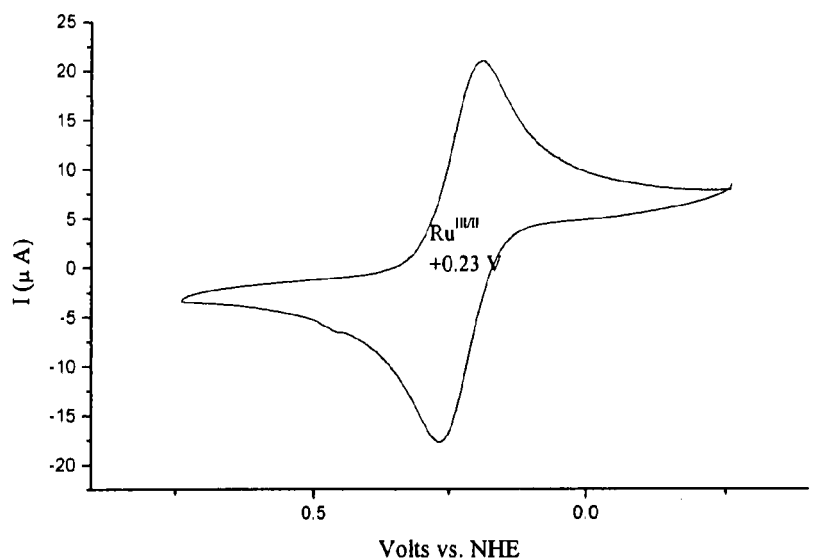
Figure 59:
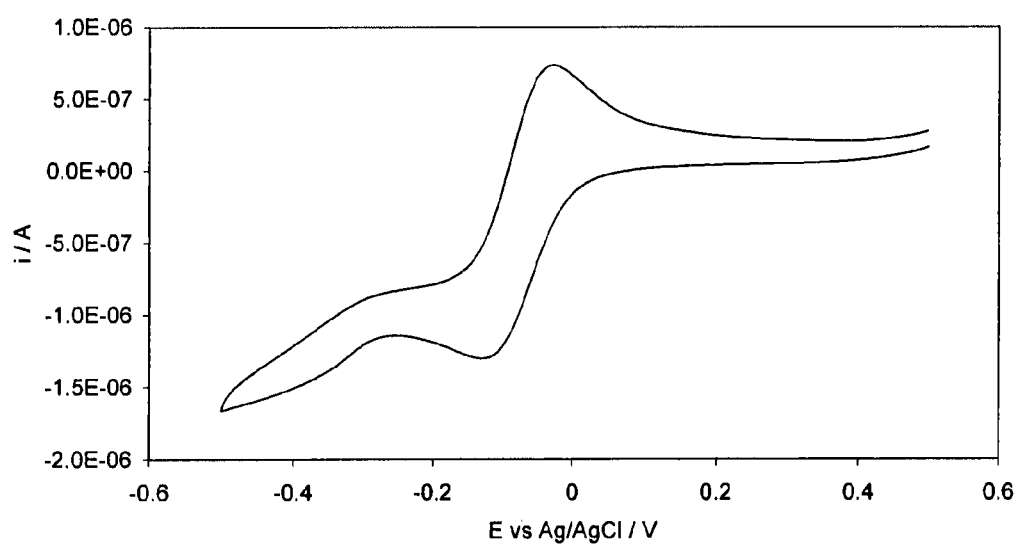
Figure 60:
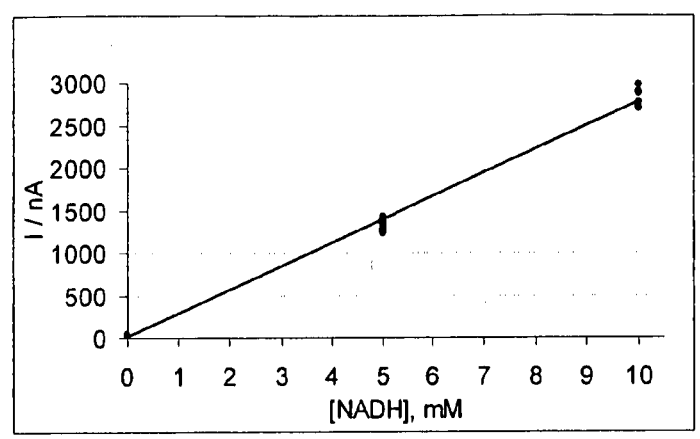
Figure 61:
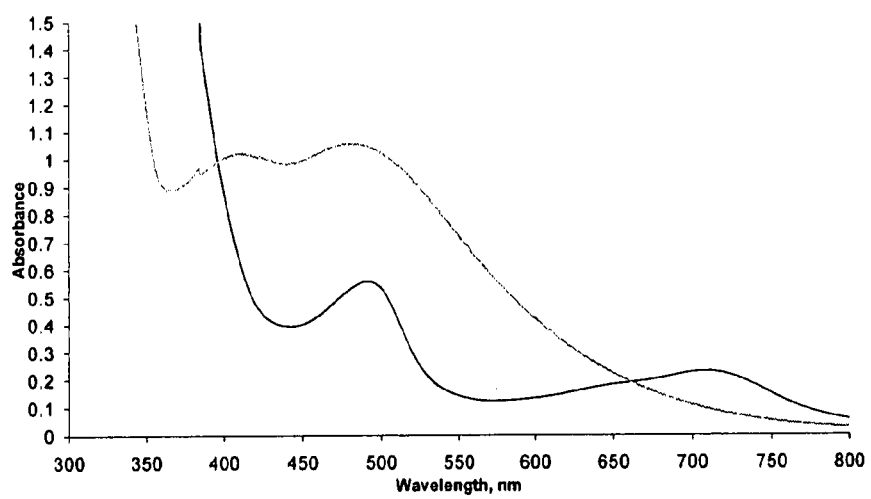
Figure 62:
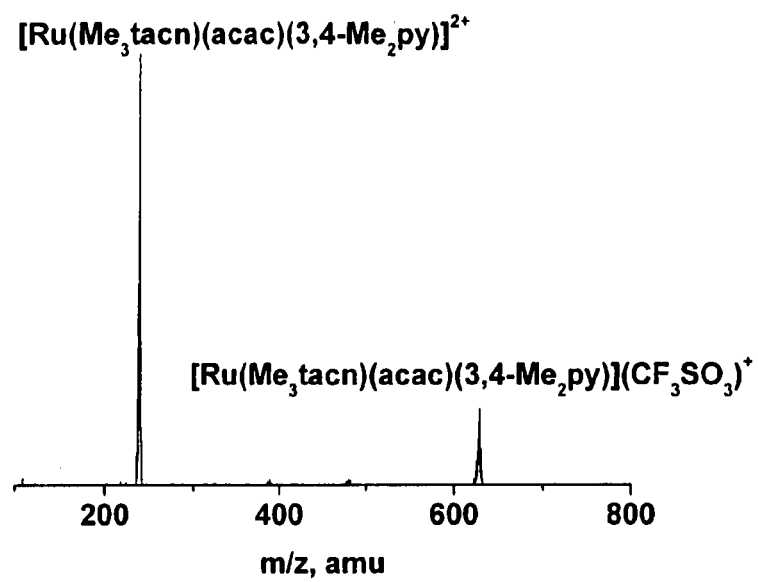
Figure 63:
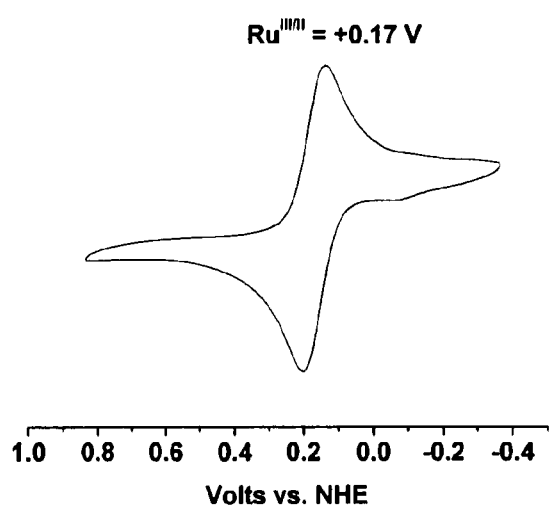
Figure 63A:
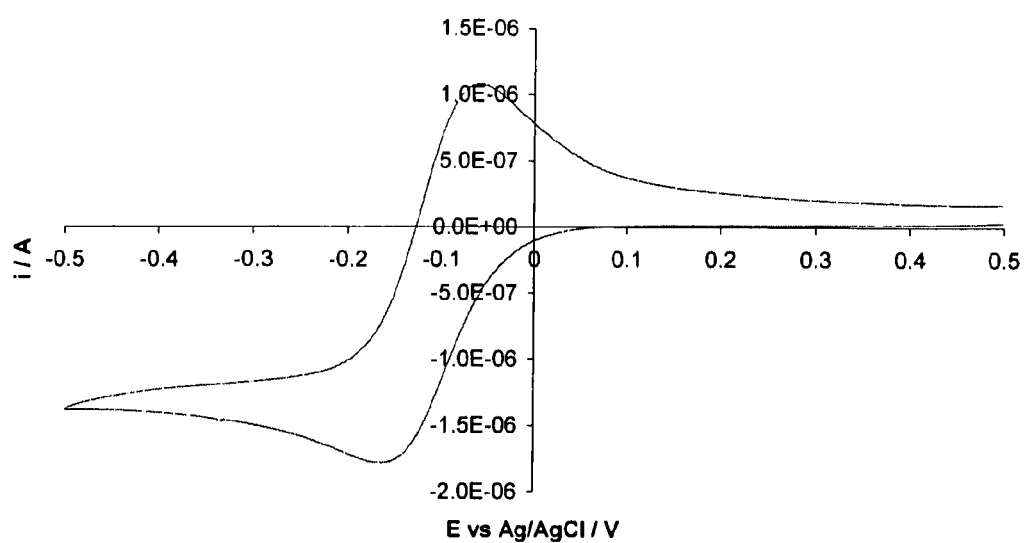
Figure 63B:
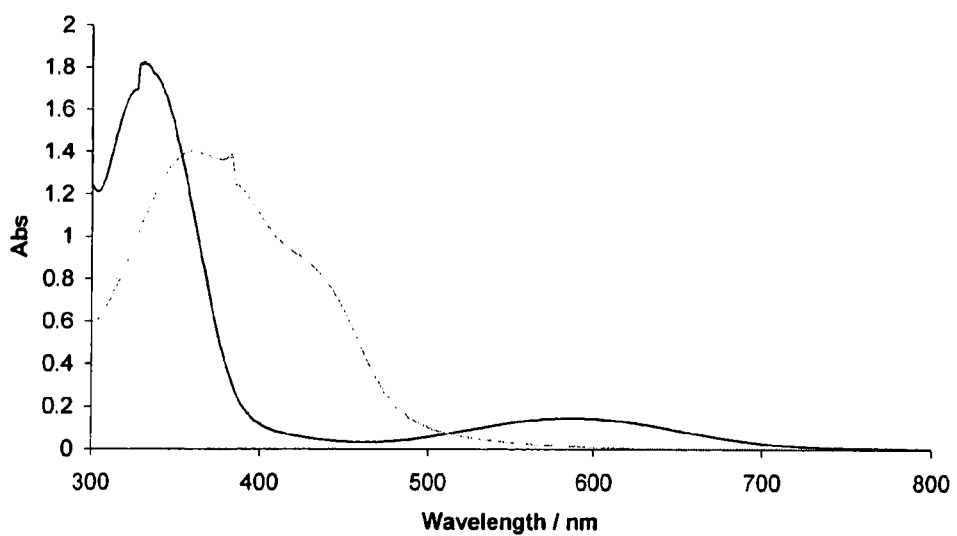
Figure 63C:
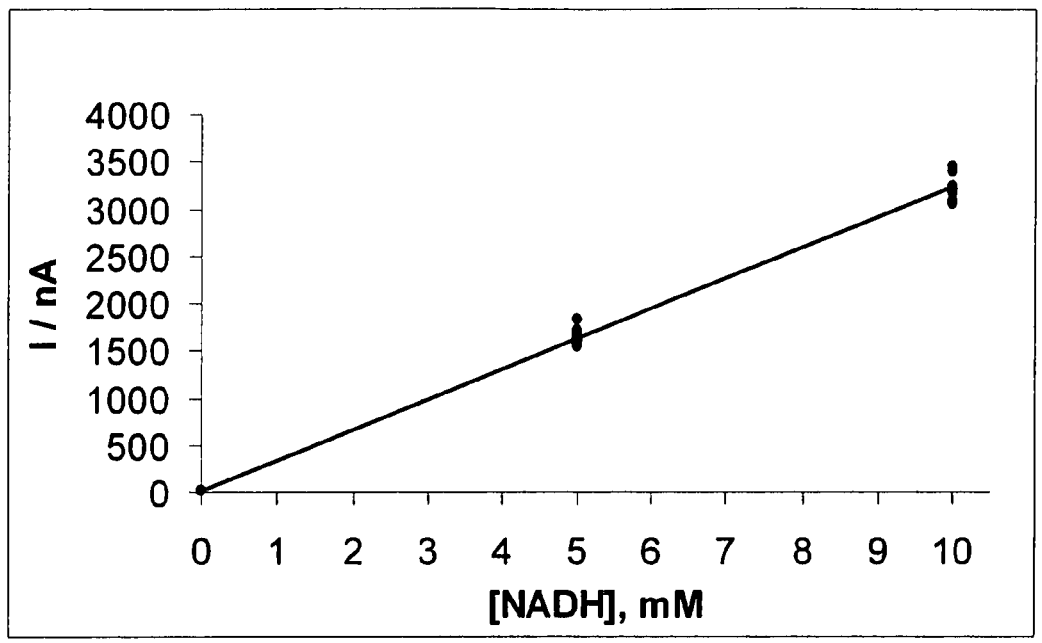
Figure 64:
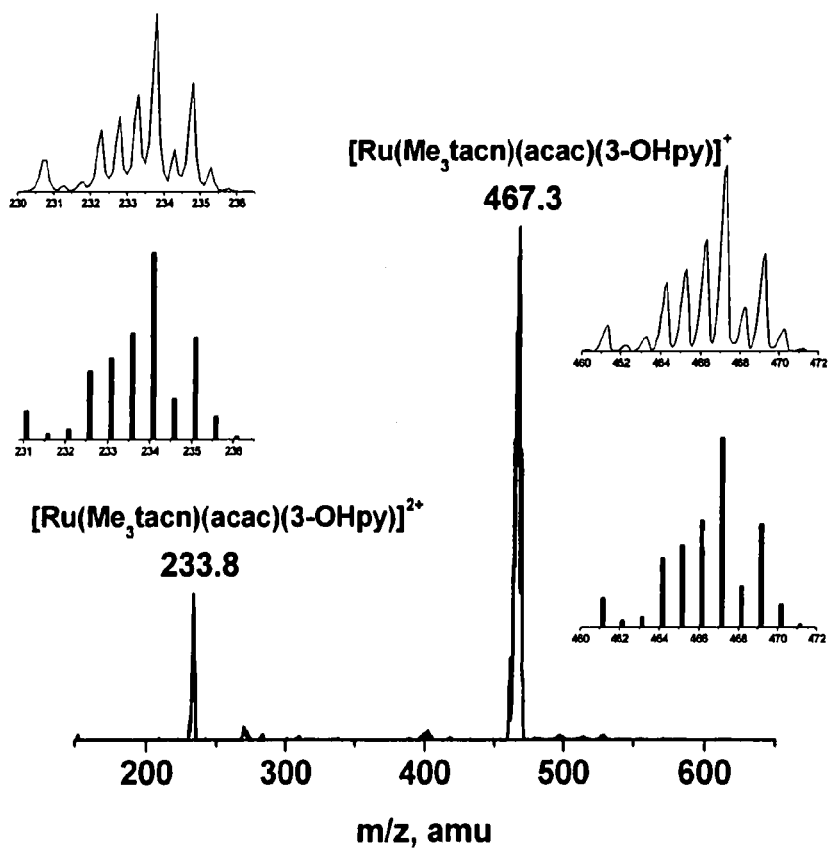
Figure 65:
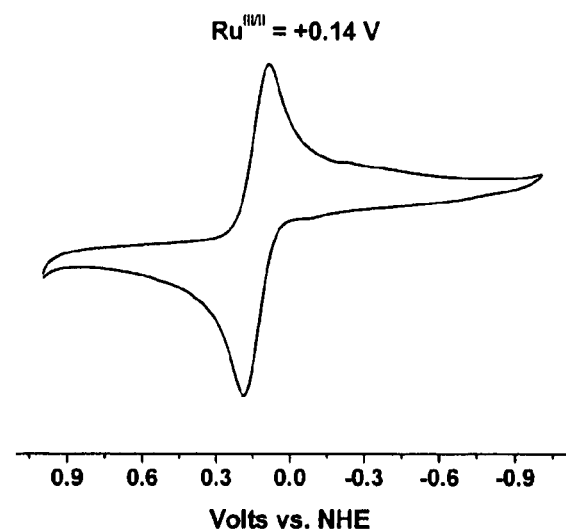
Figure 65A:
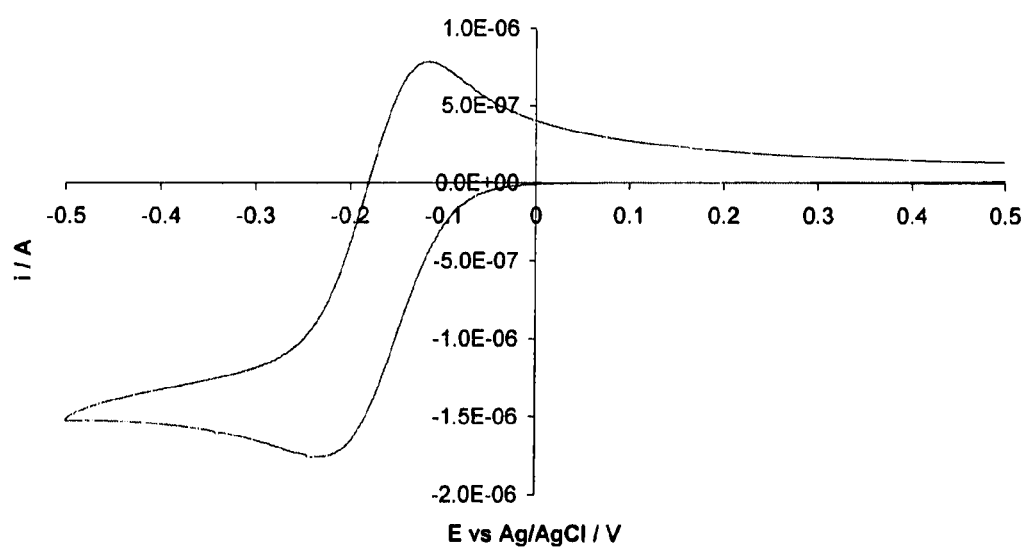
Figure 65B:
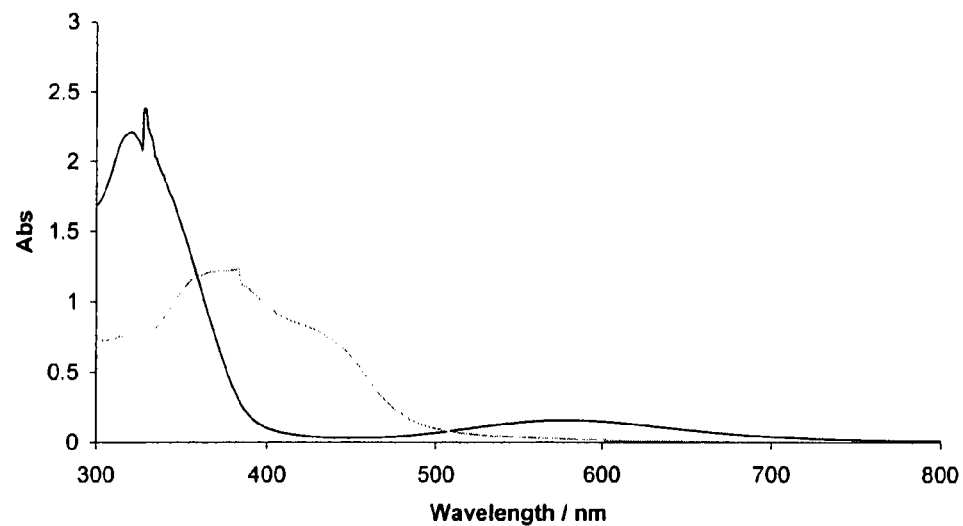
Figure 65C:
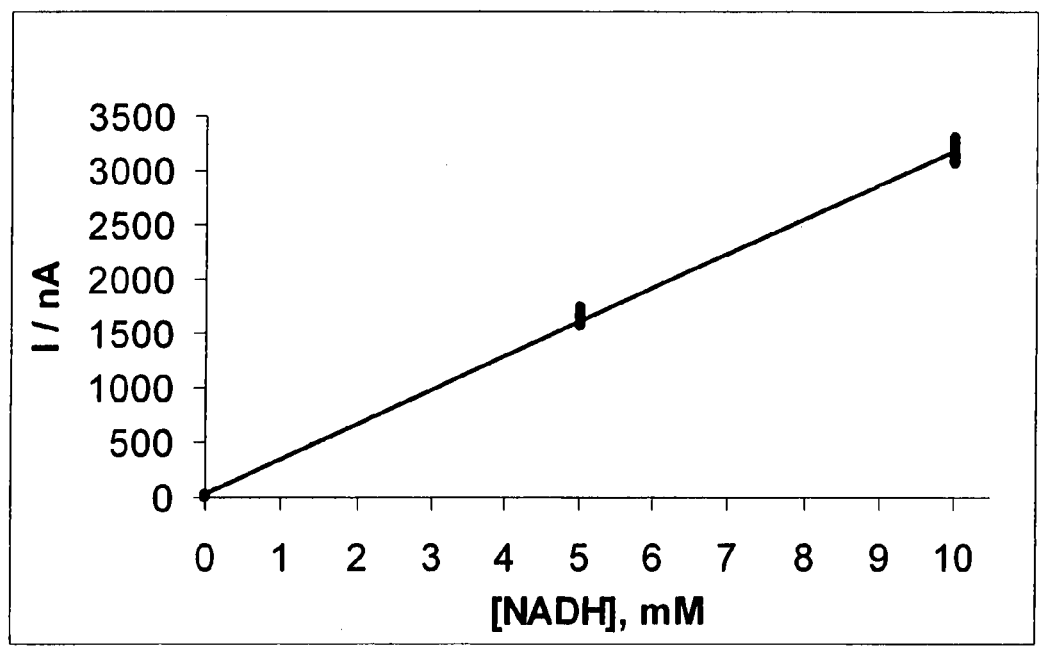
Figure 66:
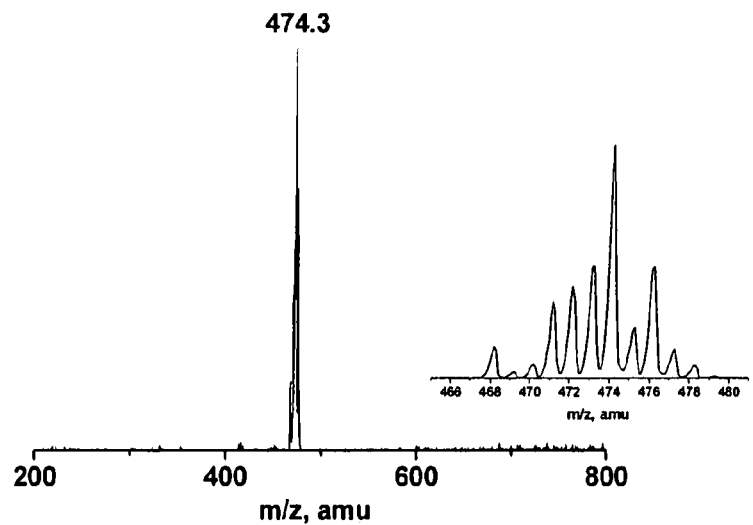
Figure 67:
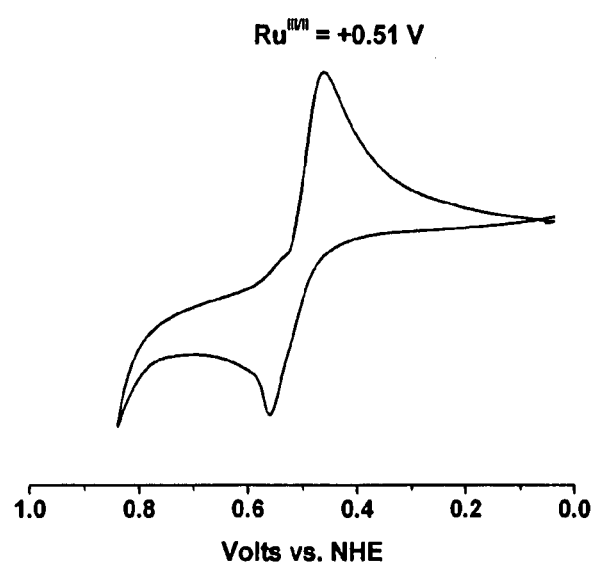
Figure 67A:
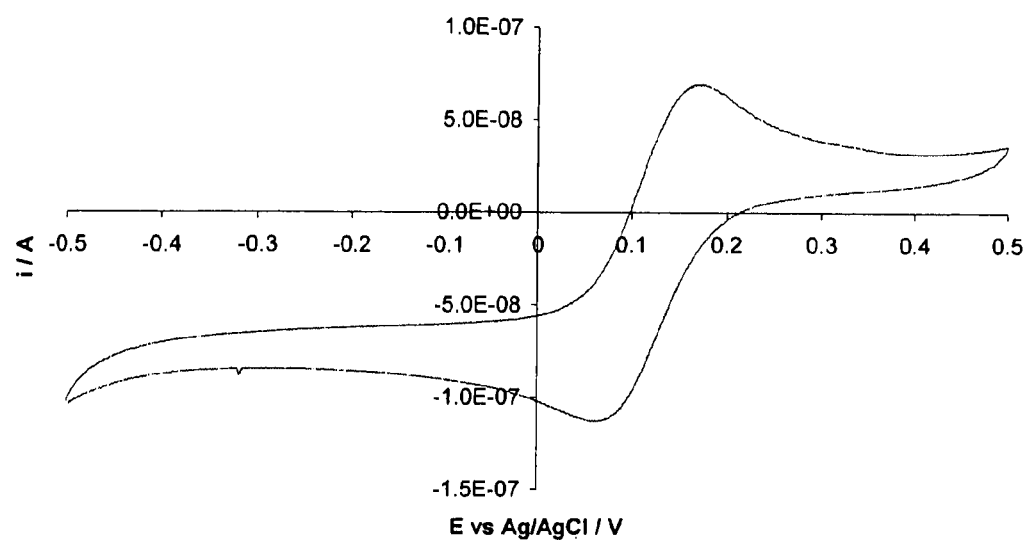
Figure 67B:
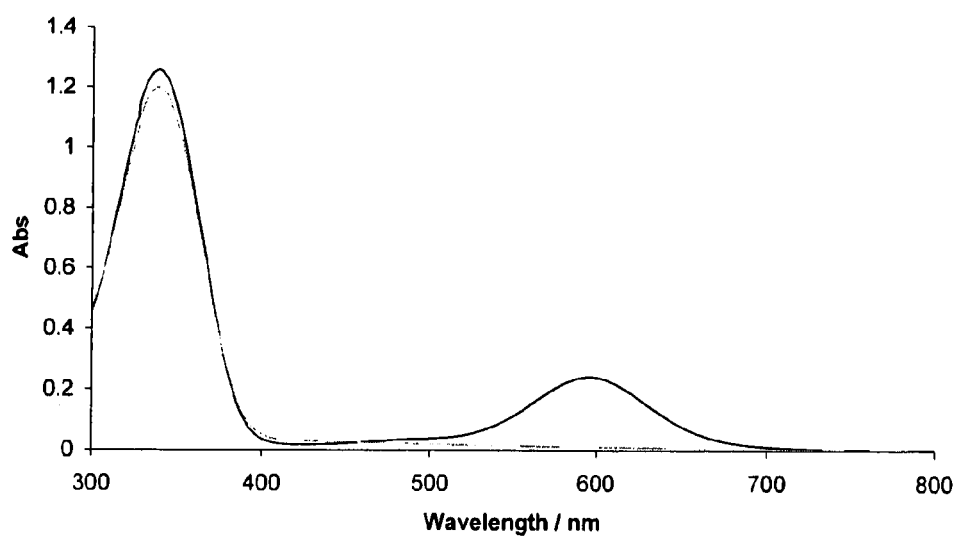
Figure 67C:
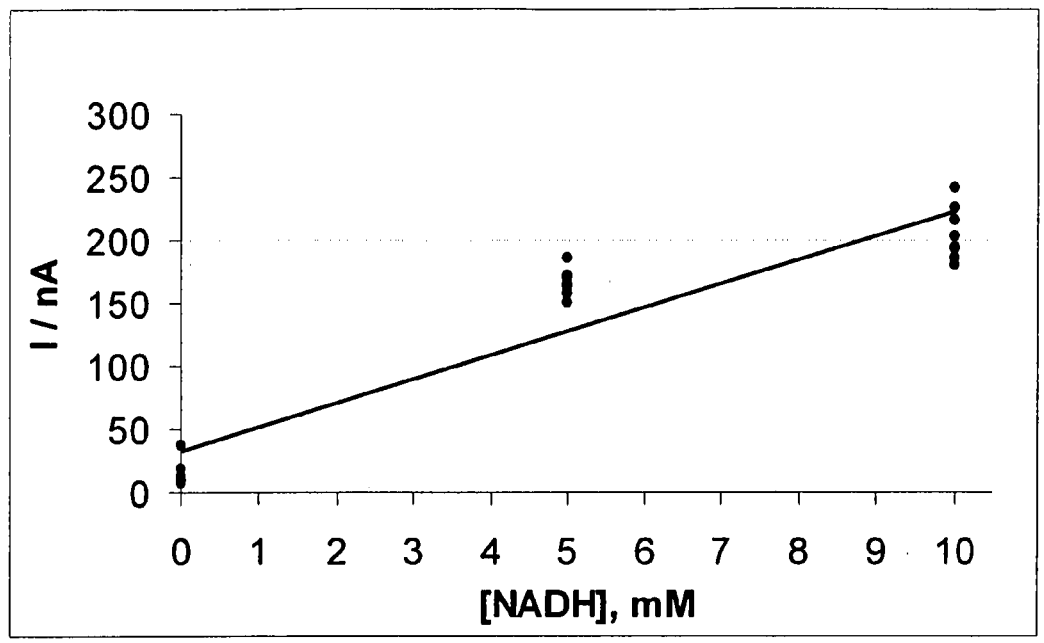
Figure 68:
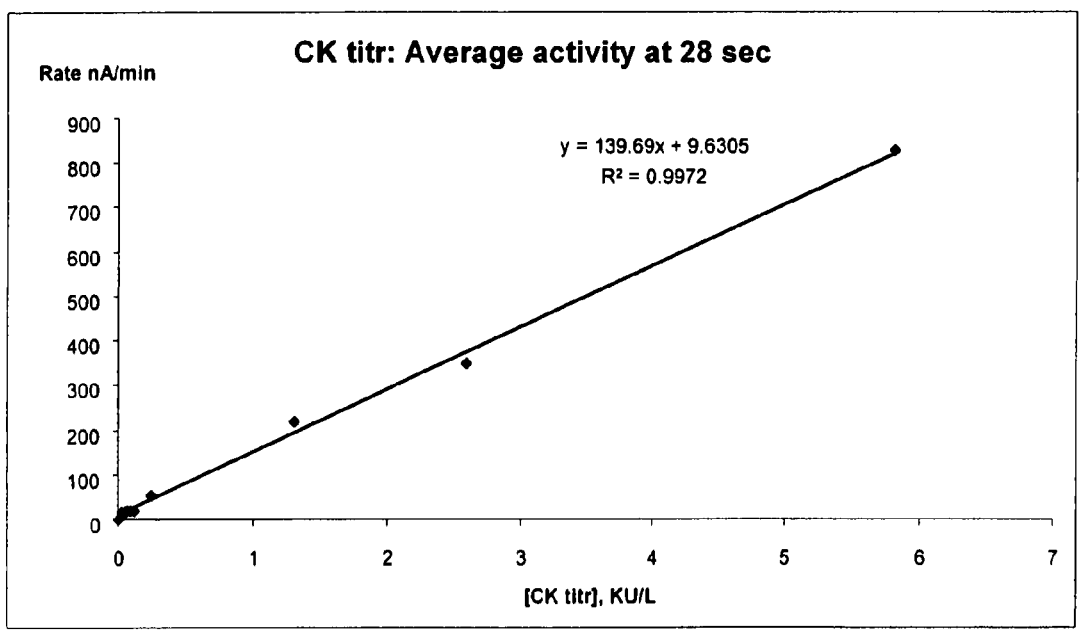
Figure 69:
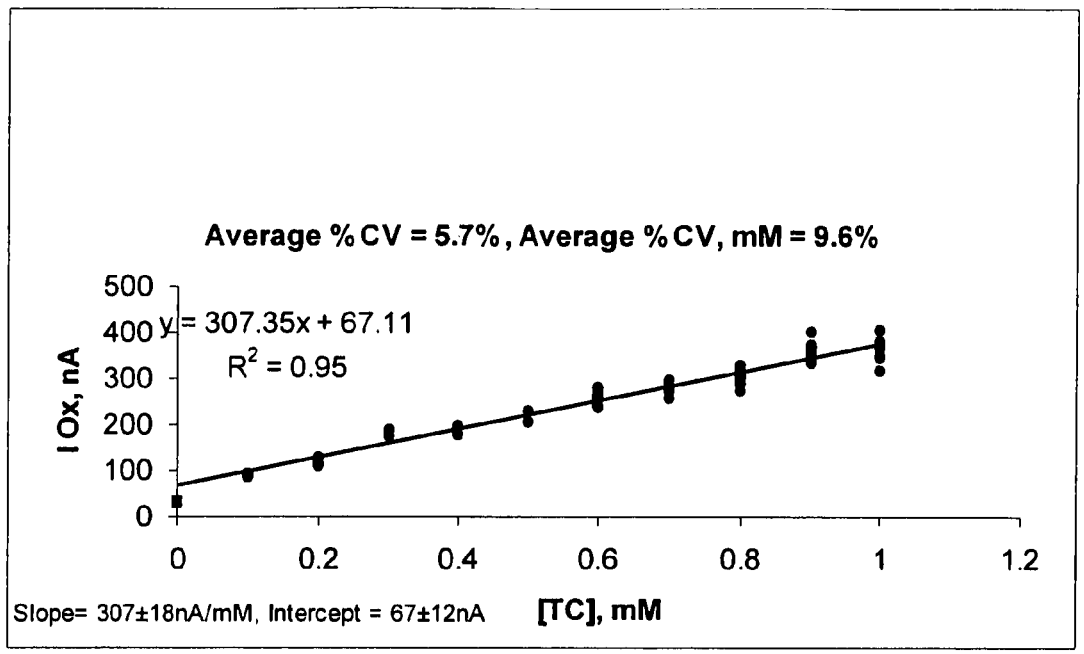
Figure 70:
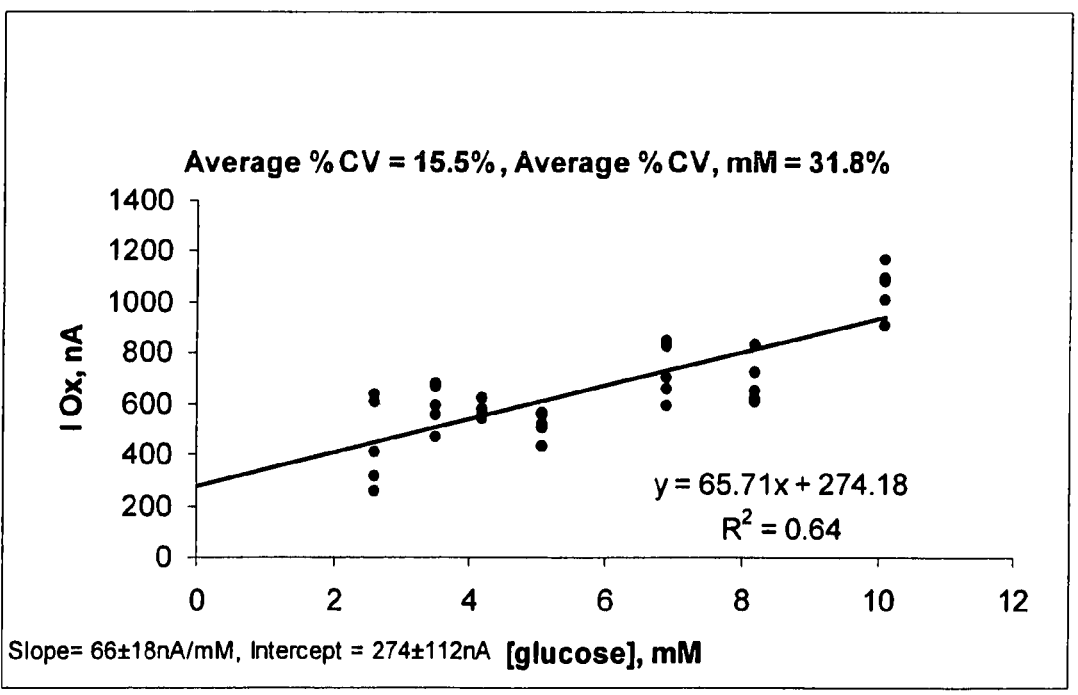

Embodiments of the present invention will now be described in a non-limitative sense only by way of the following examples and with reference to the accompanying Figures in which:

FIG. 1: ESI mass spectrum (+ve mode) of $[Ru^{II}(Me_3tacn)(acac)(1-MeIm)](PF_6)$ in acetone with the simulated isotopic patterns;

FIG. 2: Cyclic voltammogram for a standard Oxford Biosensors screen printed carbon micro-electrode strip in a solution consisting of 10 mM $[Ru^{III}(Me_3tacn)(acac)(1-MeIm)](NO_3)_2$, 0.1 M KCl and 0.1 M TRIS buffer (pH 9.0) recorded with a scan rate of 100 mVs$^{-1}$;

FIG. 3: UV absorbance spectroscopy of a solution consisting of 1 mM $[Ru^{III}(Me_3tacn)(acac)(1-MeIm)](NO_3)_2$ and 1 mM NADH in the absence (black) and presence (grey) of 0.033 mg ml$^{-1}$ PdR;

FIG. 4: Calibration plot of oxidation current versus NADH concentration for a 10 mM $[Ru^{III}(Me_3tacn)(acac)(1-MeIm)](NO_3)_2$ solution containing 2.5 mg ml$^{-1}$ PdR. Currents were recorded after an oxidation potential of +0.15 V (vs Ag/AgCl reference) was applied to the working electrode on a standard Oxford biosensors screen printed carbon micro-electrode strip using an Autolab PGSTAT12 potentiostat/galvanostat (Eco Chemie, Netherlands) connected to a multiplexer (MX452 Sternhagen design) controlled by the General Purpose Electrochemical System software (Eco Chemie, Netherlands);

FIG. 5: Plasma Total cholesterol (TC) concentration versus oxidation current recorded for a total cholesterol assay containing 80 mM $[Ru^{III}(Me_3tacn)(acac)(1-MeIm)](NO_3)_2$;

FIG. 6: Plasma triglycerides (TRG) concentration versus oxidation current recorded for a triglyceride assay containing 80 mM $[Ru^{III}(Me_3tacn)(acac)(1-MeIm)](NO_3)_2$;

FIG. 7: Plasma high density lipoprotein (HDL) concentration versus oxidation current recorded for a HDL assay containing 40 mM $[Ru^{III}(Me_3tacn)(acac)(1-MeIm)](NO_3)_2$, 6 mg ml-1 TNAD, 4 mg ml-1 PdR, 22 mg ml-1 cholesterol dehydrogenase, 23 mg ml-1 lipase, 2% wt/v BSA, 0.1M sucrose monocaprate and 0.1M neomycin;

FIG. 8: ESI mass spectra (+ve mode) of $[Ru^{II}(Me_3tacn)(acac)(py)]PF_6$ in $CH_3CN$;

FIG. 9: ESI mass spectra (+ve mode) of $[Ru^{III}(Me_3tacn)(acac)(py)](NO_3)_2$ in methanol;

FIG. 10: Cyclic voltammogram of $[Ru^{III}(Me_3tacn)(acac)(py)](NO_3)_2$ in a buffer solution containing $NaH_2PO_4$ (0.005 M)/$Na_2HPO_4$ (0.094 M) (pH=8.05) in milli Q water. Glassy carbon as working electrode, platinum wire as counter electrode, SCE as reference electrode. $K_3[Fe(CN)_6]$ was used as internal standard with +0.18 V vs SCE;

FIG. 11: Cyclic voltammogram for a standard Oxford Biosensors screen printed carbon micro-electrode strip in a solution consisting of 10 mM $[Ru^{III}(Me_3tacn)(acac)(py)](NO_3)_2$, 0.1 M KCl and 0.1 M TRIS buffer (pH 9.0) recorded with a scan rate of 100 mVs$^{-1}$;

FIG. 12: UV absorbance spectroscopy of a solution consisting of 2 mM $[Ru^{III}(Me_3tacn)(acac)(py)](NO_3)_2$ and 5 mM NADH in the absence (black) and presence (grey) of 0.033 mg ml$^{-1}$ PdR;

FIG. 13: Calibration plot of oxidation current versus NADH concentration for a 10 mM $[Ru^{III}(Me_3tacn)(acac)(py)](NO_3)_2$ solution containing 1 mg ml$^{-1}$ PdR. Currents were recorded after an oxidation potential of +0.15 V (vs Ag/AgCl reference) was applied to the working electrode on a standard Oxford Biosensors screen printed carbon micro-electrode strip using an Autolab PGSTAT12 potentiostat/galvanostat (Eco Chemie, Netherlands) connected to a multiplexer (MX452 Sternhagen design) controlled by the General Purpose Electrochemical System software (Eco Chemie, Netherlands);

FIG. 14: Plasma total cholesterol calibration plot of oxidation current for a total cholesterol sensor containing 50 mM $[Ru^{III}(Me_3tacn)(acac)(py)](NO_3)_2$ and 3% Anameg-7, NAD (9.6 mg/ml), PdR(4.3 mg/ml), ChE(3.3 mg/ml), ChDh(42 mg/ml), Anameg-7(3%), myo-inositol (15 mg/ml), ectoine (15 mg/ml) in TRIS pH 9. Currents were recorded after an oxidation potential of +0.15 V (vs Ag/AgCl reference) was applied to the working electrode on a standard Oxford Biosensors screen printed carbon micro-electrode strip using an Autolab PGSTAT12 potentiostat/galvanostat (Eco Chemie, Netherlands) connected to a multiplexer (MX452, Sternhagen Design), controlled by the General Purpose Electrochemical System software (Eco Chemie, Netherlands);

FIG. 15: Cyclic voltammogram for a standard Oxford Biosensors screen printed carbon micro-electrode strip in a solution consisting of 10 mM [Ru$^{III}$(Me$_3$TACN)(acac)(4-MePy)]Cl$_2$, 0.1 M KCl and 0.1 M TRIS buffer (pH 9.0) recorded with a scan rate of 100 mVs$^{-1}$;

FIG. 16: UV absorbance spectroscopy of a solution consisting of 1.25 mM [Ru$^{III}$(Me$_3$TACN)(acac)(4-MePy)]Cl$_2$ and 1.25 mM NADH in the absence (black) and presence (grey) of 0.033 mg ml$^{-1}$ PdR;

FIG. 17: Calibration plot of oxidation current versus the total cholesterol (TC) concentration for different lyophilized serum samples. Currents were recorded after an oxidation potential of +0.15 V (vs Ag/AgCl reference) was applied to the working electrode on a standard Oxford Biosensors screen printed carbon micro-electrode strip using an. Autolab PGSTAT12 potentiostat/galvanostat (Eco Chemie, Netherlands) connected to a multiplexer (MX452 Sternhagen design) controlled by the General Purpose Electrochemical System software (Eco Chemie, Netherlands);

FIG. 18: ESI mass spectrum (+ve mode) of [Ru$^{III}$(Me$_3$tacn)(acac)(3-Clpy)](NO$_3$)$_2$ in methanol (insets show the expanded isotopic patterns). a) calculated isotopic patterns of [Ru$^{III}$(Me$_3$tacn)(acac)(3-Clpy)]$^{2+}$ and b) calculated isotopic pattern of [Ru$^{II}$(Me$_3$tacn)(acac)(3-Clpy)]$^+$;

FIG. 19: Cyclic voltammogram of [Ru$^{III}$(Me$_3$tacn)(acac)(3-Clpy)](NO$_3$)$_2$ in a buffer solution containing NaH$_2$PO$_4$ (0.005 M)/Na$_2$HPO$_4$ (0.094 M) (pH=8.20) in milli Q water. Glassy carbon as working electrode, platinum wire as counter electrode, SCE as reference electrode. K$_3$[Fe(CN)$_6$] was used as internal standard with +0.18 V vs SCE;

FIG. 20: UV absorbance spectroscopy of a solution consisting of 1 mM [Ru$^{III}$(Me$_3$tacn)(acac)(3-Clpy)](NO$_3$)$_2$ and 1 mM NADH in the absence (black) and presence (grey) of 0.033 mg ml$^{-1}$ PdR;

FIG. 21: Cyclic voltammogram for a standard Oxford Biosensors screen printed carbon micro-electrode strip in a solution consisting of 10 mM [Ru$^{III}$(Me$_3$tacn)(acac)(3-Clpy)](NO$_3$)$_2$, 0.1 M KCl and 0.1 M TRIS buffer (pH 9.0) recorded with a scan rate of 100 mVs$^{-1}$;

FIG. 22: Cyclic voltammogram for a standard Oxford Biosensors screen printed carbon micro-electrode strip in a solution consisting of 10 mM [Ru(Me$_3$tacn)(acac)(isna)](NO$_3$)$_2$, 0.1 M KCl and 0.1 M TRIS buffer (pH 9.0) recorded with a scan rate of 100 mVs$^{-1}$;

FIG. 23: UV absorbance spectroscopy of a solution consisting of 1 mM [Ru(Me$_3$tacn)(acac)(isna)](NO$_3$)$_2$ and 1 mM NADH in the absence (black) and presence (grey) of 0.066 mg ml$^{-1}$ PdR;

FIG. 24: Cyclic voltammogram for a standard Oxford Biosensors screen printed carbon micro-electrode strip in a solution consisting of 10 mM [Ru$^{III}$(Me$_3$TACN)(acac)(pz)](NO$_3$)$_2$, 0.1 M KCl and 0.1 M TRIS buffer (pH 9.0) recorded with a scan rate of 100 mVs$^{-1}$;

FIG. 25: ESI mass spectrum (+ve mode) of [Ru$^{III}$(Me$_3$TACN)(acac)(pz)](NO$_3$)$_2$ in acetone (insets show the experimental and simulated isotopic patterns);

FIG. 26: Cyclic voltammogram of [Ru$^{III}$(Me$_3$tacn)(acac)(pz)](NO$_3$)$_2$ in buffer solution containing NaH$_2$PO$_4$ (0.005 M)/Na$_2$HPO$_4$ (0.094 M) (pH=8.20) in milli Q water. Glassy carbon as working electrode, platinum wire as counter electrode, SCE as reference electrod. K$_3$[Fe(CN)$_6$] was used as internal standard with +0.18 V vs SCE;

FIG. 27: UV absorbance spectroscopy of a solution consisting of 1 mM [Ru$^{III}$(Me$_3$tacn)(acac)(pz)](NO$_3$)$_2$ and 1 mM NADH in the absence (black) and presence (grey) of 0.033 mg ml$^{-1}$ PdR;

FIG. 28: Calibration plot of oxidation current versus the total cholesterol (TC) concentration for different lyophilized serum samples. Currents were recorded after an oxidation potential of +0.15 V (vs Ag/AgCl reference) was applied to the working electrode on a standard Oxford Biosensors screen printed carbon micro-electrode strip using an Autolab PGSTAT12 potentiostat/galvanostat (Eco Chemie, Netherlands) connected to a multiplexer (MX452 Sternhagen design) controlled by the General Purpose Electrochemical System software (Eco Chemie, Netherlands);

FIG. 29: Cyclic voltammetry of [Ru$^{III}$(Me$_3$tacn)(acac)(3-MeO-py)](NO$_3$)$_2$ recorded using a two electrode configuration with the standard OB well electrode as working electrode and an on-chip Ag/AgCl counter-reference electrode and with a scan rate of 100 mV s$^{-1}$. The black line is for 10 mM [Ru$^{III}$(Me$_3$tacn)(acac)(3-MeO-py)](NO$_3$)$_2$ in 0.1 M Tris pH9 buffer containing 0.1 M KCl and 10 mM NADH and the grey line is the same solution after addition of 2.5 mg ml$^{-1}$ PdR;

FIG. 30: ESI mass spectrum (+ve mode) of [Ru$^{III}$(Me$_3$tacn)(acac)(4-OMe-py)](NO$_3$)$_2$ in methanol (insets show the expanded isotopic patterns);

FIG. 31: Cyclic voltammogram of [Ru$^{III}$(Me$_3$tacn)(acac)(4-MeO-py)](NO$_3$)$_2$ in a buffer solution of NaH$_2$PO$_4$ (0.005 M)/Na$_2$HPO$_4$ (0.094 M) (pH=8.20). Glassy carbon as working electrode, platinum wire as counter electrode, SCE as reference electrode. K$_3$[Fe(CN)$_6$] was used as internal standard (+0.18 V vs SCE);

FIG. 32: Cyclic voltammetry of [Ru$^{III}$(Me$_3$tacn)(acac)(3-OMe-py)](NO$_3$)$_2$, recorded using a two electrode configuration with the standard OB well electrode as working electrode and an on-chip Ag/AgCl counter-reference electrode and with a scan rate of 100 mV s$^{-1}$. The black line is for 10 mM [Ru$^{III}$(Me$_3$tacn)(acac)(4-OMe-py)](NO$_3$)$_2$ in 0.1 M Tris pH9 buffer containing 0.1 M KCl and 10 mM NADH, and the grey line is the same solution after addition of 2.5 mg ml$^{-1}$ PdR;

FIG. 33: Calibration plot of oxidation current versus NADH concentration for a 10 mM [Ru$^{III}$(Me$_3$tacn)(acac)(4-OMe-py)](NO$_3$)$_2$ solution containing 2.5 mg ml$^{-1}$ PdR. Currents were recorded after an oxidation potential of +0.15 V (vs Ag/AgCl reference) was applied to the working electrode on a standard Oxford Biosensors screen printed carbon microelectrode strip using an Autolab PGSTAT12 potentiostat/galvanostat (Eco Chemie, Netherlands) connected to a multiplexer (MX452 Sternhagen design) controlled by the General Purpose Electrochemical System software (Eco Chemie, Netherlands);

FIG. 34: ESI mass spectrum (+ve mode) of [Ru$^{III}$(Me$_3$tacn)(acac)(1-MeIm)](NO$_3$)$_2$ in methanol;

FIG. 35: Cyclic voltammogram for a standard Oxford Biosensors screen printed carbon micro-electrode strip in a solution consisting of 10 mM [Ru$^{III}$(Me$_3$tacn)(acac)(1-MeIm)](NO$_3$)$_2$, 0.1 M KCl and 0.1 M TRIS buffer (pH 9.0) recorded with a scan rate of 100 mVs$^{-1}$;

FIG. 36: UV absorbance spectroscopy of a solution consisting of 1 mM [Ru$^{III}$(Me$_3$tacn)(acac)(1-MeIm)](NO$_3$)$_2$ and 1 mM NADH in the absence (black) and presence (grey) of 0.033 mg ml$^{-1}$ PdR;

FIG. 37: Calibration plot of oxidation current versus NADH concentration for a 10 mM [Ru$^{III}$(Me$_3$tacn)(acac)(1-MeIm)](NO$_3$)$_2$ solution containing 2.5 mg ml$^{-1}$ PdR. Currents were recorded after an oxidation potential of +0.15 V (vs Ag/AgCl reference) was applied to the working electrode on a standard Oxford Biosensors screen printed carbon microelectrode strip using an Autolab PGSTAT12 potentiostat/galvanostat (Eco Chemie, Netherlands) connected to a multiplexer (MX452 Sternhagen design) controlled by the General Purpose Electrochemical System software (Eco Chemie, Netherlands);

FIG. 38: ESI mass spectrum of $[Ru^{III}(Me_3tacn)(acac)(1-MeIm)](CF_3SO_3)_2$ in acetone (+ve mode);

FIG. 39: Cyclic voltammogram of $[Ru^{III}(Me_3tacn)(acac)(1-MeIm)](CF_3SO_3)_2$ in a buffer solution containing $NaH_2PO_4$ (0.005 M)/$Na_2HPO_4$ (0.094 M) (pH=8.05) in $H_2O$ Glassy carbon as working electrode, platinum wire as counter electrode, SCE as reference electrode. $K_3[Fe(CN)_6]$ was used as internal standard with +0.18 V vs SCE;

FIG. 39$a$: Cyclic voltammogram for a standard Oxford Biosensors screen printed carbon micro-electrode strip in a solution consisting of 10 mM $[Ru^{III}(Me_3TACN)(acac)(1-MeIm)](CF_3SO_3)_2$, 0.1 M KCl, 1% chaps and 0.1 M TRIS buffer (pH 9.0) recorded with a scan rate of 100 mVs$^{-1}$;

FIG. 39$b$: UV absorbance spectroscopy of a solution consisting of 1 mM $[Ru^{III}(Me_3TACN)(acac)(1-MeIm)](CF_3SO_3)_2$, 0.1 M KCl, 1% chaps, 0.1 M TRIS buffer (pH 9.0) and 1 mM NADH in the absence (black) and presence (grey) of 0.030 mg ml$^{-1}$ PdR;

FIG. 39$c$: Calibration plot of oxidation current versus NADH concentration for a 10 mM $[Ru^{III}(Me_3TACN)(acac)(1-MeIm)](CF_3SO_3)_2$ solution containing 2.5 mg ml$^{-1}$ PdR. Currents were recorded after an oxidation potential of +0.15 V (vs Ag/AgCl reference) was applied to the working electrode on a standard Oxford Biosensors screen printed carbon micro-electrode strip using an Autolab PGSTAT12 potentiostatlgalvanostat (Eco Chemie, Netherlands) connected to a to a multiplexer (MX452, Sternhagen Design) controlled by the General Purpose Electrochemical System software (Eco Chemie, Netherlands);

FIG. 40: ESI mass spectrum (+ve mode) of $[Ru^{III}(Me_3tacn)(acac)(4-Me_2N-py)](NO_3)_2 \cdot H_2O$ in methanol with the experimental and simulated isotopic patterns;

FIG. 41: Cyclic voltamrriogram of $[Ru^{III}(Me_3tacn)(acac)(4-Me_2N-py)](NO_3)_2 \cdot H2O$ in a buffer solution containing $NaH_2PO_4$ (0.005 M)/$Na_2HPO_4$ (0.094 M) (pH=8.20) in milli Q water. Glassy carbon as working electrode, platinum wire as counter electrode, SCE as reference electrode. $K_3[Fe(CN)_6]$ was used as internal standard with +0.18 V vs SCE;

FIG. 42: Cyclic voltammogram for a standard Oxford Biosensors screen printed carbon micro-electrode strip in a solution consisting of 10 mM $[Ru^{III}(Me_3tacn)(acac)(4-Me_2N-py)](NO_3)_2$, 0.1 M KCl and 0.1 M TRIS buffer (pH 9.0) recorded with a scan rate of 100 mVs$^{-1}$;

FIG. 43: UV absorbance spectroscopy of a solution consisting of 1 mM $[Ru^{III}(Me_3tacn)(acac)(4-Me_2N-py)](NO_3)_2$ and 1 mM NADH in the absence (black) and presence (grey) of 0.033 mg ml$^{-1}$ PdR;

FIG. 44: ESI mass spectrum (+ve mode) of $[Ru^{III}(Me_3tacn)(acac)(4-^tBupy)](NO_3)_2 \cdot 3H_2O$ in methanol with the experimental and simulated isotopic patterns;

FIG. 45: Cyclic voltammogram of $[Ru^{III}(Me_3tacn)(acac)(4-^tBupy)](NO_3)_2 \cdot 3H_2O$ in a buffer solution containing $NaH_2PO_4$ (0.005 M)/$Na_2HPO_4$ (0.094 M) (pH=8.20) in milli Q water. Glassy carbon as working electrode, platinum wire as counter electrode, SCE as reference electrode. $K_3[Fe(CN)_6]$ was used as internal standard with +0.18 V vs SCE;

FIG. 46: Cyclic voltammetry of 10 mM $[Ru^{III}(Me_3tacn)(acac)(4-^tBupy)](NO_3)_2$ in 0.1 M Tris pH9 buffer recorded using a two electrode configuration with the standard OB well electrode as working electrode and an on-chip Ag/AgCl counter-reference electrode and with a scan rate of 100 mV s$^{-1}$;

FIG. 47: UV absorbance spectroscopy of a solution consisting of 1 mM $[Ru^{III}(Me_3tacn)(acac)(4-^tBupy)](NO_3)_2$ and 1 mM NADH in the absence (black) and presence (grey) of 0.033 mg ml$^{-1}$ PdR;

FIG. 48: Calibration plot of oxidation current versus NADH concentration for a 10 mM $[Ru^{III}(Me_3tacn)(acac)(4-^tBupy)](NO_3)_2$ solution containing 2.5 mg ml$^{-1}$ PdR. Currents were recorded after an oxidation potential of +0.15 V (vs Ag/AgCl reference) was applied to the working electrode on a standard Oxford Biosensors screen printed carbon microelectrode strip using an Autolab PGSTAT12 potentiostatlgalvanostat (Eco Chemie, Netherlands) connected to a multiplexer (MX452 Sternhagen design) controlled by the General Purpose Electrochemical System software (Eco Chemie, Netherlands);

FIG. 49: UV absorbance spectroscopy of a solution consisting of 1 mM $[Ru^{III}(Me_3tacn)(acac)(isoquinoline)](NO_3)_2$ and 1 mM NADH in the absence (black) and presence (grey) of 0.033 mg ml$^{-1}$ PdR;

FIG. 50: Cyclic voltammetry of 10 mM $[Ru^{III}(Me_3tacn)(acac)(isoquinoline)](NO_3)_2$ in 0.1 M Tris pH9 buffer, recorded using a two electrode configuration with the standard OB well electrode as working electrode and an on-chip Ag/AgCl counter-reference electrode and with a scan rate of 100 mV s$^{-1}$;

FIG. 51: ESI mass spectrum (+ve mode) of $[Ru^{III}(Me_3tacn)(tropolone)(pyridine)]PF_6$ in acetone with experimental and simulated isotopic patterns;

FIG. 52: ESI mass spectrum (+ve mode) of $[Ru^{III}(Me_3tacn)(tropolone)(pyridine)](NO_3)_2$ in methanol with the experimental and simulated isotopic patterns;

FIG. 53: Cyclic voltammogram of $[Ru^{III}(Me_3tacn)(tropolone)(py)](NO_3)_2$ in a buffer solution containing $NaH_2PO_4$ (0.005 M)/$Na_2HPO_4$ (0.094 M) (pH=8.20) in milli Q water. Glassy carbon as working electrode, platinum wire as counter electrode, SCE as reference electrode. $K_3[Fe(CN)_6]$ was used as internal standard with +0.18 V vs. SCE;

FIG. 54: Calibration plot of oxidation current versus NADH concentration for a 10 mM $[Ru^{III}(Me_3tacn)(tropolone)(py)](NO_3)_2$ solution containing 2.5 mg ml$^{-1}$ PdR. Currents were recorded after an oxidation potential of +0.15 V (vs Ag/AgCl reference) was applied to the working electrode on a standard Oxford Biosensors screen printed carbon micro-electrode strip using an Autolab PGSTAT12 potentiostat/galvanostat (Eco Chemie, Netherlands) connected to a multiplexer (MX452 Sternhagen design) controlled by the General Purpose Electrochemical System software (Eco Chemie, Netherlands);

FIG. 55: UV absorbance spectroscopy of a solution consisting of 1 mM $[Ru^{III}(Me_3tacn)(tropolone)(py)](NO_3)_2$ and 1 mM NADH in the absence (black) and presence (grey) of 0.033 mg ml$^{-1}$ PdR;

FIG. 56: Cyclic voltammetry of 10 mM$[Ru^{III}(Me_3tacn)(tropolone)(py)](NO_3)_2$ in 0.1 M Tris pH9 buffer recorded using a two electrode configuration with the standard OB well electrode as working electrode and an on-chip Ag/AgCl counter-reference electrode and with a scan rate of 100 mV s$^{-1}$;

FIG. 57: ESI mass spectrum (+ve mode) of $[Ru^{III}(Me_3tacn)(tropolone)(4-tert-butyl-py)](NO_3)_2$ in methanol with the experimental and simulated isotopic patterns;

FIG. 58: Cyclic voltammogram of $[Ru^{III}(Me_3tacn)(tropolone)(4-tert-butyl-py)](NO_3)_2$ in a buffer solution containing $NaH_2PO_4$ (0.005 M)/$Na_2HPO_4$ (0.094 M) (pH=8.20) in milli Q water. Glassy carbon as working electrode, platinum wire as counter electrode, SCE as reference electrode. $K_3[Fe(CN)_6]$ was used as internal standard with +0.18 V vs. SCE;

FIG. 59: Cyclic voltammetry of 10 mM [Ru$^{III}$(Me$_3$tacn)(tropolone)(4-tert-butyl-py)](NO$_3$)$_2$ in 0.1 M Tris pH9 buffer, recorded using a two electrode configuration with the standard OB well electrode as working electrode and an on-chip Ag/AgCl counter-reference electrode and with a scan rate of 100 mVs$^{-1}$;

FIG. 60: Calibration plot of oxidation current versus NADH concentration for a 10 mM [Ru$^{III}$(Me$_3$tacn)(tropolone)(4-tert-butyl-py)](NO$_3$)$_2$ solution containing 1 mg ml$^{-1}$ PdR. Currents were recorded after an oxidation potential of +0.15 V (vs Ag/AgCl reference) was applied to the working electrode on a standard Oxford Biosensors screen printed carbon micro-electrode strip using an Autolab PGSTATI2 potentiostat/galvanostat (Eco Chemie, Netherlands) connected to a multiplexer (MX452 Sternhagen design) controlled by the General Purpose Electrochemical System software (Eco Chemie, Netherlands);

FIG. 61: UV absorbance spectroscopy of a solution consisting of 1 mM [Ru$^{III}$(Me$_3$tacn)(tropolone)(4-tert-butyl-py)](NO$_3$)$_2$ and 1 mM NADH in the absence (black) and presence (grey) of 0.033 mg ml$^{-1}$ PdR;

FIG. 62: ESI mass spectrum of [Ru$^{III}$(Me$_3$tacn)(acac)(3,4-Me$_2$-py)](CF$_3$SO$_3$) in acetone (+ve mode);

FIG. 63: Cyclic voltammogram of [Ru$^{III}$(Me$_3$tacn)(acac)(3,4-Me$_2$py)](CF$_3$SO$_3$)$_2$ in buffer solution containing NaH$_2$PO$_4$ (0.005 M)/Na$_2$HPO$_4$ (0.094 M) (pH=8.05) in H$_2$O Glassy carbon as working electrode, platinum wire as counter electrode, SCE as reference electrode. $K_3[Fe(CN)_6]$ was used as internal standard with +0.18 V vs. SCE;

FIG. 63a: Cyclic voltammogram for a standard Oxford Biosensors screen printed carbon micro-electrode strip in a solution consisting of 10 mM [Ru$^{III}$(Me$_3$TACN)(acac)(3,4-Me$_2$py)](CF$_3$SO$_3$)$_2$, 0.1 M KCl, 1% chaps and 0.1 M TRIS buffer (pH 9.0) recorded with a scan rate of 100 mVs$^{-1}$;

FIG. 63b: UV absorbance spectroscopy of a solution consisting of 1 mM [Ru$^{III}$(Me$_3$TACN)(acac)(3,4-Me$_2$py)](CF$_3$SO$_3$)$_2$, 0.1 M KCl, 1% chaps, 0.1 M TRIS buffer (pH 9.0) and 1 mM NADH in the absence (black) and presence (grey) of 0.030 mg ml$_{-1}$ PdR;

FIG. 63c: Calibration plot of oxidation current versus NADH concentration for a 10 mM [Ru$^{III}$(Me$_3$TACN)(acac)(3,4-Me$_2$py)](CF$_3$SO3)$_2$ solution containing 2.5 mg ml-1 PdR. Currents were recorded after an oxidation potential of +0.15 V (vs Ag/AgCl reference) was applied to the working electrode on a standard Oxford Biosensors screen printed carbon micro-electrode strip using an Autolab PGSTATI2 potentiostatlgalvanostat (Eco Chemie, Netherlands) connected to a to a multiplexer (MX452, Sternhagen Design) controlled by the General Purpose Electrochemical System software (Eco Chemie, Netherlands);

FIG. 64: ESI-MS of [Ru$^{III}$(Me$_3$tacn)(acac)(3-OHpy)](NO$_3$)$_2$ (+ve mode) in methanol. (Insets show the experimental (top) and simulated (bottom) isotopic patterns;

FIG. 65: Cyclic voltammogram of [Ru$^{III}$(Me$_3$tacn)(acac)(3-OHpy)](NO$_3$)$_2$ in buffer solution containing NaH$_2$PO$_4$ (0.005 M)/Na$_2$HPO$_4$ (0.094 M) (pH=8.05) in H$_2$O Glassy carbon as working electrode, platinum wire as counter electrode, SCE as reference electrode. $K_3[Fe(CN)_6]$ was used as internal standard with +0.18 V vs. SCE;

FIG. 65a: Cyclic voltammogram for a standard Oxford Biosensors screen printed carbon micro-electrode strip in a solution consisting of 10 mM [Ru$^{III}$(Me$_3$TACN)(acac)(3-OHpy)](NO$_3$)$_2$, 0.1 M KCl, 1% chaps and 0.1 M TRIS buffer (pH 9.0) recorded with a scan rate of 100 mVs$^{-1}$;

FIG. 65b: UV absorbance spectroscopy of a solution consisting of 1 mM [Ru$^{III}$(Me$_3$TACN)(acac)(3-OHpy)](NO$_3$)$_2$, 0.1 M KCl, 1% chaps, 0.1 M TRIS buffer (pH 9.0) and 1 mM NADH in the absence (black) and presence (grey) of 0.030 mg ml$^{-1}$ PdR;

FIG. 65c: Calibration plot of oxidation current versus NADH concentration for a 10 mM [Ru$^{III}$(Me$_3$TACN)(acac)(3-OHpy)](NO$_3$)$_2$ solution containing 2.5 mg ml-1 PdR. Currents were recorded after an oxidation potential of +0.15 V (vs Ag/AgCl reference) was applied to the working electrode on a standard Oxford Biosensors screen printed carbon micro-electrode strip using an Autolab PGSTAT12 potentiostat/galvanostat (Eco Chemie, Netherlands) connected to a multiplexer (MX452, Sternhagen Design) controlled by the General Purpose Electrochemical System software (Eco Chemie, Netherlands);

FIG. 66: ESI mass spectrum of [Ru$^{III}$(tmc)(NCS)$_2$](ClO$_4$) in methanol with the isotopic pattern;

FIG. 67: Cyclic voltammogram of [Ru$^{III}$(tmc)(NCS)$_2$](ClO$_4$) in 0.1 M TFA. Glassy carbon as working electrode, platinum wire as counter electrode, SCE as reference electrode. $K_3[Fe(CN)_6]$ was used as internal standard with +0.18 V vs. SCE;

FIG. 67a: Cyclic voltammogram for a standard Oxford Biosensors screen printed carbon micro-electrode strip in a solution consisting of 0.32 mM [Ru$^{III}$(TMC)(NCS)$_2$](ClO$_4$), 0.1 M KCl, 1% chaps and 0.1 M TRIS buffer (pH 9.0) recorded with a scan rate of 100 mVs$^{-1}$;

FIG. 67b: UV absorbance spectroscopy of a solution consisting of 0.01 mM [Ru$^{III}$(TMC)(NCS)$_2$](ClO$_4$), 0.1 M KCl, 1% chaps, 0.1 M TRIS buffer (pH 9.0) and 1 mM NADH in the absence (black) and presence (grey) of 0.030 mg ml$^{-1}$ PdR;

FIG. 67c: Calibration plot of oxidation current versus NADH concentration for a 0.32 mM [Ru$^{III}$(TMC)(NCS)$_2$](ClO$_4$) solution containing 2.5 mg ml$^{-1}$ PdR. Currents were recorded after an oxidation potential of +0.15 V (vs Ag/AgCl reference) was applied to the working electrode on a standard Oxford Biosensors screen printed carbon micro-electrode strip using an Autolab PGSTATI2 potentiostat/galvanostat (Eco Chemie, Netherlands) connected to a multiplexer (MX452, Sternhagen Design) controlled by the General Purpose Electrochemical System software (Eco Chemie, Netherlands);

FIG. 68: Sensor responses plotted vs. time for each CK (see Example 17);

FIG. 69: Sensor responses plotted vs creatinine concentration (see Example 18);

FIG. 70: Sensor responses plotted vs glucose concentration (see Example 19); and FIG. 71: [Ru$^{III}$(Me$_3$TACN)(acac)(1-MeIm)](NO$_3$)$_2$ glucose mix testing saliva with standard additions of glucose.

Throughout the Examples which follow L denotes the ligand 1,4,7-trimethyl-1,4,7-triazacyclononane. The material

[Ru$^{II}$(L)(acac)(OH)]PF$_6$ is prepared according to Schneider et al: Inorg. Chem., 1993, 32, 4925. All of the Examples use 0.1M KCl and 1% CHAPS.

EXAMPLE 1

See FIGS. 1 to 7

[Ru$^{III}$(Me$_3$TACN)(acac)(1-MeIm)](NO$_3$)$_2$

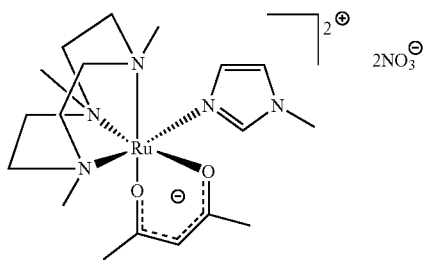

Method 1
Preparation of [Ru$^{II}$(Me$_3$TACN)(acac)(1-MeIm)]PF$_6$

N-methylimidazole (0.5 g, 6.0 mmol) was added to [Ru$^{II}$(L)(acac)(OH)]PF$_6$ (100 mg, 0.19 mmol) in absolute ethanol (5 mL). The solution was refluxed under argon in the presence of a few pieces of Zn amalgam for 24 h. After cooling to room temperature, acetone (15 mL) was added and the solution was then filtered. The filtrate was evaporated to dryness to give an orange solid which was filtered and washed with diethyl ether. Yield (100 mg). ESI/MS (positive mode) in acetone: m/z=454.4, [M]$^+$.

Preparation of [Ru$^{III}$(L)(acac)(1-MeIm)](NO$_3$)$_2$

A solution of AgCF$_3$SO$_3$ (45 mg, 0.17 mmol) in acetone (2 mL) was slowly added to [Ru$^{II}$(Me$_3$tacn)(acac)(1-MeIm)]PF$_6$ (100 mg, 0.17 mmol) in acetone (3 mL). After 3 minutes the purple solution was filtered to remove the silver. ["Bu$_4$N] NO$_3$ (1500 mg, 0.5 mmol) was then added to give a purple precipitate which was filtered and washed with acetone. Yield (50 mg). ESI/MS (positive mode) in methanol: m/z=277.5, [M]$^{2+}$. E$_{1/2}$ of Ru$^{III/II}$=+0.09 V vs. NHE in buffer solution (pH 8.20).

EXAMPLE 2

See FIG. 8-14

[Ru$^{III}$(Me$_3$tacn)(acac)(py)](NO$_3$)$_2$

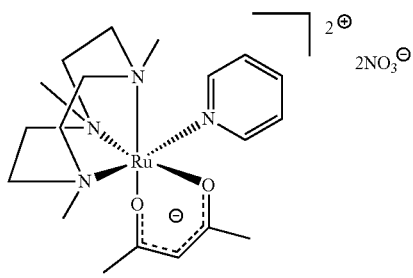

Preparation of [Ru$^{II}$(DMSO)$_4$Cl$_2$]

Ruthenium trichloride trihydrate (1.0 g) was refluxed in dimethyl sulphoxide (5 mL) for 5 minutes The volume was reduced to half in vacuo and addition of acetone (20 mL) gave a yellow precipitate. The yellow complex which separated was filtered off, washed with acetone and ether and vacuum dried.

Preparation of [Ru$^{III}$(L)Cl$_3$]

To a mixture of Ru$^{II}$(DMSO)$_4$Cl$_2$ (1.0 g, 2.1 mmol) in absolute ethanol (25 mL) was added L (0.80 g, 4.7 mmol) with stirring. The suspension was heated to 60° C. for 1 h until a clear deep red-brown solution was obtained which was then refluxed for 2 h. The solvent was removed under reduced pressure by rotary evaporation. The red-orange residue was treated with concentrated HCl and heated under reflux for 30 min in the presence of air. An orange microcrystalline solid was collected by filtration, washed with H$_2$O, ethanol and diethyl ether and air-dried.

Preparation of [Ru$^{III}$(L)(acac)(OH)]PF$_6$.H$_2$O

Solid Ru$^{III}$(L)Cl$_3$ (2.0 g; 5.0 mmol) was added in small amounts to a solution of sodium 2,4-pentanedionate (acac) (3.0 g; ~24 mmol) in water (60 mL) with stirring at ambient temperature. The mixture was stirred for 3.5 h until a clear red solution was obtained. Addition of a solution of NaPF$_6$ (2.0 g) in H$_2$O (5 mL) and cooling to 0° C. initiated the precipitation of orange microcrystals which were collected by filtration, washed with diethyl ether and air-dried Preparation of [Ru$^{II}$(L)(acac)(py)]PF$_6$ A solution containing [Ru$^{II}$(L)(acac)(OH)]PF$_6$ (105 mg, 0.20 mmol) in absolute ethanol/pyridine (5 mL) (4:1, v/v) was heated to reflux under argon atmosphere in the presence of 10 pieces of Zn amalgam for 4 h. After cooling to ambient temperature, the red microcrystalline precipitate was collected by filtration, washed with diethyl ether and air-dried. The product was recrystallized from acetone/diethyl ether. Yield: (94 mg, 79%) ESI/MS (positive mode): m/z=451, [M]$^+$. E$_{1/2}$ of Ru$^{III/II}$=-0.18 V vs. Fc$^{+/0}$ in 0.1 M TBAH in CH$_3$CN.

Preparation of [Ru$^{III}$(L)(acac)(py)](NO$_3$)$_2$

A solution of AgCF$_3$SO$_3$ (42 mg, 0.16 mmol) in acetone (1 mL) was slowly added to an orange acetone solution (3 mL) containing [Ru$^{II}$(Me$_3$tacn)(acac)(py)]PF$_6$ (90 mg, 0.15 mmol). After stirring for 5 minutes, solid ["Bu$_4$N]NO$_3$ (304 mg, 1 mmol) was added and the purple precipitate was filtered, washed with acetone and then diethyl ether. The product was recrystallized from methanol/diethyl ether. Yield: (64 mg, 87%) ESI/MS (positive mode): m/z=451.0, [M]⁺; 225.4, [M]²⁺. $E_{1/2}$ of $Ru^{III/II}$=0.2 V vs. NHE in buffer solution (pH 8.05).

EXAMPLE 3

See FIGS. 15-17

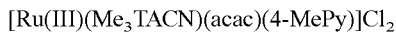
[Ru(III)(Me₃TACN)(acac)(4-MePy)]Cl₂

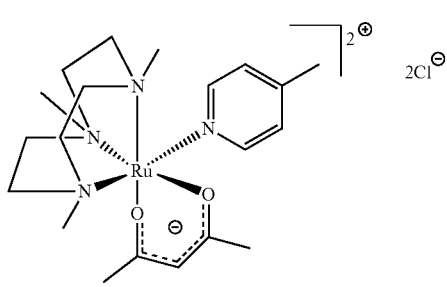

Preparation of [Ru$^{II}$(Me₃tacn)(acac)(4-Mepy)]PF₆

4-picoline (0.4 g, 4 mmol) was added to [Ru$^{III}$(Me₃tacn)(acac)(OH)]PF₆ (200 mg, 0.37 mmol) in absolute ethanol (15 mL). The solution was refluxed under argon in the presence of 20 pieces of Zn amalgam for 24 h. After cooling to room temperature, the solution was filtered and the filtrate was then evaporated to dryness to give a brown solid which was filtered and then washed with diethyl ether. Yield (290 mg). ESI/MS (positive mode) in acetone: m/z=465.2, [M]⁺. Anal. calcd. for C₂₀H₃₅N₄O₂PF₆Ru: C, 39.41; H, 5.79; N, 9.11. Found: C, 39.53; H, 5.82; N, 8.98.

Preparation of [Ru$^{III}$(Me₃tacn)(acac)(4-Mepy)](PF₆)₂

A solution of (NH₄)₂[Ce(NO₃)₆] (134 mg, 0.24 mmol) in acetone (10 mL) was slowly added to the orange solution in acetone (5 mL) containing [Ru$^{II}$(Me₃tacn)(acac)(4-Mepy)]PF₆ (120 mg, 0.20 mmol). After 3 minutes the purple solid was filtered and washed with acetone. The purple solid was then dissolved in deionized water (10 mL) and the solution was filtered, and NH₄PF₆ (133 mg, 0.82 mmol) was added to give a purple precipitate, which was filtered and washed with deionized water. Yield (105 mg). ESI/MS (positive mode) in acetone: m/z=232.8, [M]²⁺. Anal. calcd. for C₂₀H₃₅N₄O₂P₂F₁₂Ru: C, 31.84; H, 4.68; N, 7.43. Found: C, 31.90; H, 4.65; N, 7.32.

Preparation of [Ru$^{III}$(Me₃tacn)(acac)(4-Mepy)](NO₃)₂.H₂O

A solution of [$^n$Bu₄N]NO₃ (230 mg, 0.76 mmol) in acetone (5 mL) was slowly added to the purple solution of [Ru$^{III}$(Me₃tacn)(acac)(4-Mepy)](PF₆)₂ (140 mg, 0.19 mmol) in acetone (10 mL). The purple precipitate was filtered, washed with acetone and vacuum dried. Yield (40 mg). ESI/MS (positive mode) in methanol: m/z=232.8, [M]²⁺. $E_{1/2}$ of $Ru^{III/II}$=+0.18 V vs. NHE in buffer solution (pH 8.20). Anal. calcd. for C₂₀H₃₅N₆O₈Ru.H₂O: C, 39.60; H, 6.15; N, 13.85. Found: C, 39.72; H, 6.01; N, 13.90.

EXAMPLE 4

See FIGS. 18-21

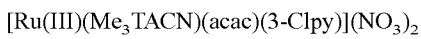
[Ru(III)(Me₃TACN)(acac)(3-Clpy)](NO₃)₂

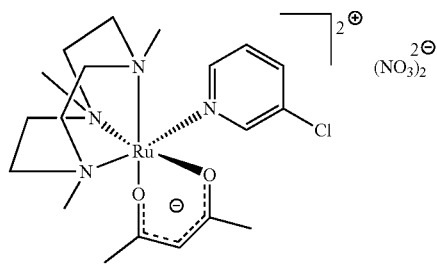

Preparation of [Ru$^{II}$(L)(acac)(3-Clpy)]PF₆

A solution containing [Ru$^{II}$(L)(acac)(OH)]PF₆ (150 mg, 0.28 mmol) in absolute ethanol/3-chloropyridine (5 mL) (4:1, v/v) was refluxed under argon in the presence of 10 pieces of Zn amalgam for 24 h. After cooling to room temperature, 15 mL acetone was added and the solution was then filtered. The filtrate was evaporated to dryness to give a brown solid which was filtered and then washed with diethyl ether. ESI/MS (positive mode): m/z=485.3, [M]⁺. Yield: (110 mg)

Preparation of [Ru$^{III}$(L)(acac)(3-Clpy)](NO₃)₂

A solution of AgCF₃SO₃ (45 mg, 0.17 mmol) in acetone (2 mL) was slowly added to the brown solution in acetone (3 mL) containing [Ru$^{II}$(Me₃tacn)(acac)(3-Clpy)]PF₆ (110 mg, 0.17 mmol). After 3 minutes the purple solution was filtered to remove the silver and then [$^n$Bu₄N]NO₃ (300 mg, 1 mmol) was added to give a purple precipitate which was filtered and washed with acetone. ESI/MS (positive mode) in methanol: m/z=485.3, [M]⁺; 242.9, [M]²⁺. $E_{1/2}$ of $Ru^{III/II}$=+0.27 V vs. NHE in buffer solution (pH 8.20).

EXAMPLE 5

See FIGS. 22-23

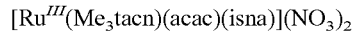
[Ru$^{III}$(Me₃tacn)(acac)(isna)](NO₃)₂

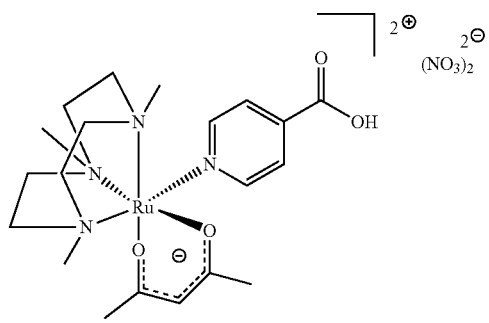

Preparation of [Ru$^{II}$(L)(acac)(ISNA)]PF$_6$ (ISNA=isonicotinamide)

Solid isonicotinamide (1 g, 8.20 mmol) was added to a suspension of [Ru$^{III}$(L)(acac)(OH)]PF$_6$ (100 mg, 0.19 mmol) in absolute ethanol (5 mL). The mixture was refluxed in the presence of a few pieces of Zn amalgam for 24 h under argon. After cooling to room temperature, 15 mL acetone was added and the solution was then filtered. The filtrate was evaporated to dryness to give a brown solid which was filtered and then washed with diethyl ether. Yield: 100 mg. The crude product was used for next step without further purification.

Preparation of [Ru$^{III}$(L)(acac)(ISNA)](NO$_3$)$_2$

A solution of AgCF$_3$SO$_3$ (45 mg, 0.17 mmol) in acetone (2 mL) was slowly added with stirring to a brown solution of [Ru$^{II}$(L)(acac)(ISNA)]PF$_6$ (100 mg) in acetone (3 mL). After 5 minutes the purple solution was filtered and then concentrated to ca. 0.5 mL followed by addition of diethyl ether (30 mL). The resulting purple solid was filtered and redissolved in acetonitrile (5 mL). Addition of [$^n$Bu$_4$N]NO$_3$ (300 mg, 1 mmol) in acetonitrile (2 mL) gave dark purple crystals after standing for 1 day. ESI/MS (positive mode) in methanol: m/z=494.4, [M]$^+$; 247.3, [M]$^{2+}$. E$_{1/2}$ of Ru$^{III/II}$=+0.28 V vs. NHE in buffer solution (pH 8.20).

EXAMPLE 6

See FIGS. 24-28

[Ru$^{III}$(Me$_3$TACN)(acac)Pz](NO$_3$)$_2$

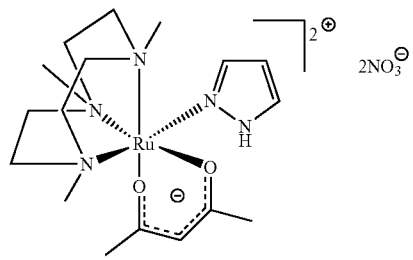

Preparation of [Ru$^{II}$(L)(acac)(pz)]PF$_6$

Pyrazole (0.5 g, 7.3 mmol) was added to [Ru$^{III}$(L)(acac)(OH)]PF$_6$ (150 mg, 0.28 mmol) in absolute ethanol (5 mL). The solution was refluxed under argon in the presence of 10 pieces of Zn amalgam for 24 h. After cooling to room temperature, acetone (15 mL) was added and the solution was then filtered. The filtrate was evaporated to dryness to give an orange solid which was filtered and then washed with diethyl ether. Yield (130 mg).

Preparation of [Ru$^{III}$(L)(acac)(pz)](NO$_3$)$_2$

A solution of AgCF$_3$SO$_3$ (60 mg, 0.23 mmol) in acetone (3 mL) was slowly added to the orange solution in acetone (7 mL) containing [Ru$^{II}$(Me$_3$tacn)(acac)(pz)]PF$_6$ (130 mg, 0.22 mmol). After 3 minutes the purple solution was filtered to remove silver. [$^n$Bu$_4$N]NO$_3$ (0.3 g, 0.98 mmol) was then added to give a purple precipitate which was filtered and washed with acetone. Yield (100 mg). ESI/MS (positive mode) in methanol: m/z=439.5, [M-H]$^+$. E$_{1/2}$ of Ru$^{III/II}$=+0.14 V vs. NHE in buffer solution (pH 8.20).

EXAMPLE 7

See FIG. 29-33

[Ru$^{III}$(Me$_3$TACN)(acac)(4-MeO-py)](NO$_3$)$_2$

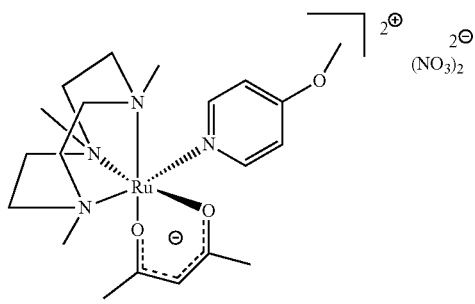

Preparation of [Ru$^{II}$(L)(acac)(4-MeO-py)]PF$_6$(1)

4-Methoxypyridine (0.4 g, 3.7 mmol) was added to [Ru$^{II}$(L)(acac)(OH)]PF$_6$ (120 mg, 0.22 mmol) in absolute ethanol (5 mL). The solution was refluxed under argon in the presence of 10 pieces of Zn amalgam for 24 h. After cooling to room temperature, acetone (15 mL) was added and the solution was then filtered. The filtrate was evaporated to dryness to give an orange solid which was filtered and washed with diethyl ether. Yield: (100 mg)

Preparation of [Ru$^{III}$(L)(acac)(4-MeO-py)](NO$_3$)$_2$

A solution of AgCF$_3$SO$_3$ (45 mg, 0.17 mmol) in acetone (5 mL) was slowly added to 1 (100 mg, 0.16 mmol) in acetone (5 mL). After 3 minutes the purple solution was filtered and then concentrated to ca. 1 mL. Addition of Et$_2$O (30 mL) gave a purple solid which was filtered and washed with Et$_2$O. The purple solid was redissolved in acetone (5 mL). [$^n$Bu$_4$N]NO$_3$ (300 mg, 1 mmol) was then slowly added. The resulting purple precipitate was filtered and washed with acetone. ESI/MS (positive mode) in methanol: m/z=240.8, [M]$^{2+}$. E$_{1/2}$ of Ru$^{III/II}$=+0.16 V vs. NHE in buffer solution (pH 8.20).

EXAMPLE 8

See FIGS. 34-37

[Ru$^{III}$(Me$_3$TACN)(acac)(1-MeIm)](NO$_3$)$_2$

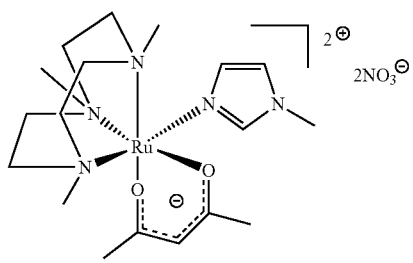

Method 2

Preparation of [Ru$^{III}$(L)(acac)(1-MeIm)](PF$_6$)$_2$

NH$_4$PF$_6$ (200 mg, 1.27 mmol) and 1-methylimidazole (200 mg, 2.44 mmol) were added to a solution containing [Ru$^{II}$(L)

(acac)(OH)]PF$_6$ (150 mg, 0.28 mmol) in absolute ethanol (5 mL). The mixture was refluxed for 1 h. After cooling to room temperature, the dark purple solid was filtered, washed with ethanol (3×5 mL) and then air-dried. Yield: (160 mg). ESI/MS (positive mode) in acetone: m/z=227.4 [M]$^{2+}$.

Preparation of [Ru$^{III}$(L)(acac)(1-MeIm)](NO$_3$)$_2$

A solution of [$^n$Bu$_4$N]NO$_3$ (200 mg, 0.67 mmol) in acetone (2 mL) was slowly added to [Ru$^{III}$(L)(acac)(1-MeIm)](PF$_6$)$_2$ (100 mg, 0.13 mmol) in acetone (8 mL) and the mixture was allowed to stand for 30 minutes The resulting purple precipitate was filtered, washed with acetone (3×5 mL) and then dried under vacuum. Yield: 70 mg. ESI/MS (positive mode) in methanol: m/z=227.3 [M]$^{2+}$. E$_{1/2}$ of Ru$^{III/II}$=+0.07 V vs. NHE. UV-Vis (H$_2$O): λ$_{max}$ [nm] (ε [mol$^{-1}$dm$^3$cm$^{-1}$]) 289 (5175), 314sh (3920), 583 (855).

EXAMPLE 8A

See FIGS. 38-39 and 39*a-c*

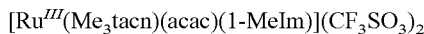
[Ru$^{III}$(Me$_3$tacn)(acac)(1-MeIm)](CF$_3$SO$_3$)$_2$

Preparation of [Ru$^{III}$(Me$_3$tacn)(acac)(1-MeIm)](CF$_3$SO$_3$)$_2$

To [Ru$^{III}$(Me$_3$tacn)(acac)(1-MeIm)](PF$_6$)$_2$ (200 mg, 0.27 mmol) dissolved in a minimum amount of acetone was added neat triflic acid (0.5 mL) with vigorous stirring. The purple solution was then added dropwise to diethyl ether (400 mL). The purple precipitate was filtered and dried under vacuum. Yield (100 mg). ESI/MS (positive mode) in methanol: m/z=277.5, [M]$^{2+}$. E$_{1/2}$ of Ru$^{III/II}$=+0.09 V vs. NHE in buffer solution (pH 8.20).

EXAMPLE 9

See FIGS. 40-43

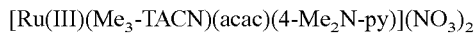
[Ru(III)(Me$_3$-TACN)(acac)(4-Me$_2$N-py)](NO$_3$)$_2$

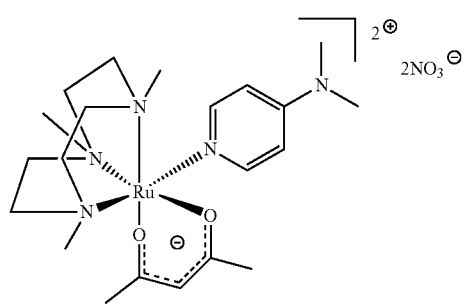

Preparation of [Ru$^{II}$(Me$_3$tacn)(acac)(4-Me$_2$N-py)]PF$_6$

4-Dimethylaminopyridine (0.3 g, 2.4 mmol) was added to [Ru$^{III}$(Me$_3$tacn)(acac)(OH)]PF$_6$ (150 mg, 0.28 mmol) in absolute ethanol (10 mL). The solution was refluxed under argon in the presence of 10 pieces of Zn amalgam for 24 h. After cooling to room temperature, the orange solid was filtered and recrystallized from acetone/diethyl ether. Yield (120 mg). ESI/MS (positive mode) in acetone: m/z=494.1, [M]$^+$. Anal. calcd. for C$_{21}$H$_{38}$N$_5$O$_2$PF$_6$Ru: C, 39.50; H, 6.00; N, 10.97. Found: C, 39.73; H, 6.05; N, 10.81.

Preparation of [Ru$^{III}$(Me$_3$tacn)(acac)(4-Me$_2$N-py)](NO$_3$)$_2$.H$_2$O

A solution of AgCF$_3$SO$_3$ (50 mg, 0.19 mmol) in acetone (2 mL) was slowly added to the orange solution of [Ru$^{II}$(Me$_3$tacn)(acac)(4-Me$_2$N-py)]PF$_6$ (120 mg, 0.19 mmol) in acetone (5 mL). After 5 minutes the purple solution was filtered to remove the silver. [$^n$Bu$_4$N]NO$_3$ (150 mg, 0.5 mmol) was then added to give a purple precipitate which was filtered, washed with acetone and vacuum dried. Yield (80 mg). ESI/MS (positive mode) in methanol: m/z=247.3, [M]$^{2+}$. E$_{1/2}$ of Ru$^{III/II}$=+0.07 V vs. NHE in buffer solution (pH 8.20). Anal. calcd. for C$_{21}$H$_{38}$N$_7$O$_8$Ru.1H$_2$O: C, 39.68; H, 6.34; N, 15.42. Found: C, 39.95; H, 6.40; N, 15.61.

EXAMPLE 10

See FIGS. 44-48

[Ru$^{III}$(Me$_3$tacn)(acac)(4-$^t$Bupy)](NO$_3$)$_2$

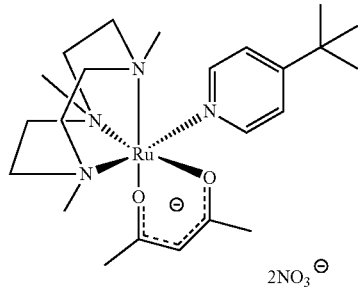

Preparation of [Ru$^{II}$(Me$_3$tacn)(acac)(4-$^t$Bupy)]PF$_6$ 4-tert-butylpyridine (0.6 g, 4.1 mmol) was added to [Ru$^{III}$(Me$_3$tacn)(acac)(OH)]PF$_6$ (300 mg, 0.56 mmol) in absolute ethanol (45 mL). The solution was refluxed under argon in the presence of 30 pieces of Zn amalgam for 24 h. After cooling to room temperature, the solution was filtered and then evaporated to dryness. The brown solid was filtered and washed with diethyl ether. Yield (290 mg). ESI/MS (positive mode) in acetone: m/z=507.3, [M]$^+$. Anal. calcd. for C$_{23}$H$_{41}$N$_4$O$_2$PF$_6$Ru: C, 42.39; H, 6.34; N, 8.60. Found: C, 42.57; H, 6.40; N, 8.68.

Preparation of [Ru$^{III}$(Me$_3$tacn)(acac)(4-$^t$Bupy)](PF$_6$)$_2$

A solution of (NH$_4$)$_2$[Ce(NO$_3$)$_6$] (202 mg, 0.37 mmol) in acetone (10 mL) was slowly added to the orange solution in acetone (5 mL) containing [Ru$^{II}$(Me$_3$tacn)(acac)(4-tert-butylpyridine)]PF$_6$ (200 mg, 0.31 mmol). After 3 minutes the purple solid was filtered and washed with acetone. The purple solid was then dissolved in deionized water (10 mL). To the filtered solution was added NH$_4$PF$_6$ (200 mg, 1.23 mmol) to give a purple precipitate which was filtered and washed with deionized water. Yield (150 mg). ESI/MS (positive mode) in acetone: m/z=253.7, [M]$^{2+}$. Anal. calcd. for C$_{23}$H$_{41}$N$_4$O$_2$P$_2$F$_{12}$Ru: C, 34.68; H, 5.19; N, 7.03. Found: C, 34.90; H, 5.14; N, 7.09.

Preparation of [Ru$^{III}$(Me$_3$tacn)(acac)(4-$^t$Bupy)](NO$_3$)$_2$.3H$_2$O

A solution of [$^n$Bu$_4$N]NO$_3$ (183 mg, 0.60 mmol) in acetone (2 mL) was slowly added to the purple solution of [Ru$^{III}$(Me$_3$tacn)(acac)(4-$^t$Bupy)]RPF$_6$)$_2$ (120 mg, 0.15 mmol) in acetone (5 mL). The purple precipitate was filtered, washed with acetone and then vacuum dried. Yield (65 mg). ESI/MS (positive mode) in methanol: m/z=253.7, [M]$^{2+}$. E$_{1/2}$ of Ru$^{III/II}$=+0.18 V vs. NHE in buffer solution (pH 8.20). Anal. calcd.

for $C_{23}H_{41}N_6O_8Ru \cdot 3H_2O$: C, 40.34; H, 6.92; N, 12.27. Found: C, 40.42; H, 6.72; N, 12.29

EXAMPLE 11

See FIGS. 49 and 50

$[Ru^{III}(Me_3tacn)(acac)(isoquinoline)](NO_3)_2$

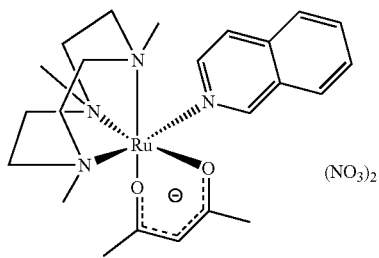

(NO$_3$)$_2$

Preparation of $[Ru^{II}(Me_3tacn)(acac)(isoquinoline)]PF_6$

Isoquinoline (0.4 g, 3.8 mmol) was added to $[Ru^{III}(Me_3tacn)(acac)(OH)]PF_6$ (200 mg, 0.38 mmol) in absolute ethanol (30 mL). The solution was refluxed under argon in the presence of 20 pieces of Zn amalgam for 24 h. The resulting brown solution was cooled and then filtered. The filtrate was concentrated to ca. 1 mL. Diethyl ether was added and the brown precipitate was filtered, washed with diethyl ether and then air dried. Yield (190 mg). ESI/MS (positive mode) in acetone: m/z=501.3, [M]$^+$.

Preparation of $[Ru^{III}(Me_3tacn)(acac)(isoquinoline)](PF_6)_2$

A solution of $(NH_4)_2[Ce(NO_3)_6]$ (194 mg, 0.35 mmol) in acetone (10 mL) was slowly added to the orange solution in acetone (5 mL) containing $[Ru^{II}(Me_3tacn)(acac)(isoquinoline)]PF_6$ (190 mg, 0.29 mmol). After 3 minutes the purple solid was filtered and washed with acetone. The purple solid was then dissolved in 10 ml deionized water and the solution was filtered. NH$_4$PF$_6$ (192 mg, 1.18 mmol) was added to give a purple precipitate which was filtered and washed with deionized water. Yield (120 mg). ESI/MS (positive mode) in acetone: m/z=250.7, [M]$^{2+}$.

Preparation of $[Ru^{III}(Me_3tacn)(acac)(isoquinoline)](NO_3)_2$

A solution of [$^nBu_4N$]NO$_3$ (274 mg, 0.90 mmol) in acetone (3 mL) was slowly added to the purple solution of $[Ru^{III}(Me_3tacn)(acac)(isoquinoline)](PF_6)_2$ (240 mg, 0.30 mmol) in acetone (8 mL). The purple precipitate was filtered, washed with acetone and vacuum dried. Yield (120 mg). ESI/MS (positive mode) in methanol: m/z=250.7, [M]$^{2+}$. $E_{1/2}$ of Ru$^{III/}$$^{II}$=+0.21 V vs. NHE in buffer solution (pH 8.20).

EXAMPLE 12

See FIGS. 51-56

$[Ru^{III}(Me_3tacn)(tropolone)(py)](NO_3)_2$

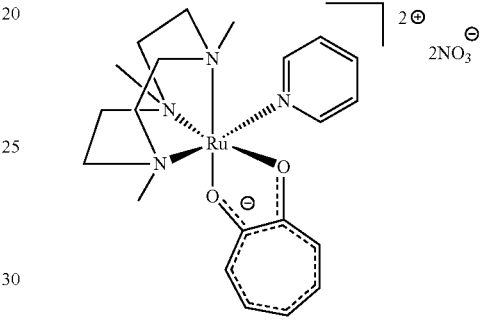

2⊕ 2NO$_3$⊖

Preparation of $[Ru^{II}(Me_3tacn)(tropolone)(py)](PF_6)$

A yellow mixture of $[Ru^{III}(Me_3tacn)Cl_3]$ (120 mg, 0.32 mmol) and tropolone (47 mg, 0.38 mmol) in 5 mL H$_2$O was refluxed in air for 2 h. The resulting deep green solution was filtered and NH$_4$PF$_6$ (323 mg, 1.98 mmol) was added to give a green precipitate which was filtered and washed with deionized H$_2$O. The green solid was suspended in 10 mL ethanol and pyridine (400 µL, 4.95 mmol) was added. The mixture was then refluxed under argon overnight in the presence of a few pieces of zinc amalgam. The resulting brown solution was cooled and the brown precipitate was filtered, washed with ethanol and then air dried. Yield: 26%, 52 mg. ESI-MS: m/z=473.3, [M$^+$].

Preparation of $[Ru^{III}(Me_3tacn)(tropolone)(py)](NO_3)_2$

A solution of AgCF$_3$SO$_3$ (32 mg, 0.12 mmol) in acetone (3 mL) was slowly added to the brown acetone solution (5 mL) of $[Ru^{II}(Me_3tacn)(tropolone)(py)]PF_6$ (52 mg, 0.08 mmol). The brown solution turned green immediately and the mixture was stirred in the dark for 30 minutes. The silver metal in the solution was removed by centrifuge and the green solution was then slowly added to ca. 80 mL diethyl ether. The green precipitate was collected by filtration and washed with diethyl ether. It was then dissolved in 5 mL acetone and a solution of [$^nBu_4N$]NO$_3$ (77 mg, 0.25 mmol) in acetone (2 mL) was slowly added. The green precipitate was filtered, washed with acetone and vacuum dried. Yield: 86%, 41 mg. ESI-MS: m/z=236.8, [M$^{2+}$]. E$_{1/2}$ of Ru$^{III/II}$=0.25V vs. NHE in buffer solution (pH 8.20).

EXAMPLE 13

See FIGS. 57-61

[Ru$^{III}$(Me$_3$tacn)(tropolone)(4-t-butyl-py)](NO$_3$)$_2$

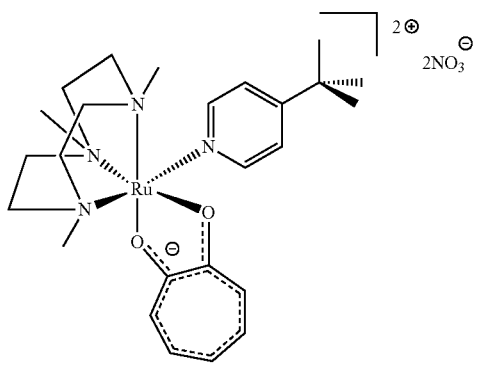

Preparation of [Ru$^{II}$(Me$_3$tacn)(tropolone)(4-t-butyl-py)](PF$_6$)

A yellow mixture of [Ru$^{III}$(Me$_3$tacn)Cl$_3$] (120 mg, 0.32 mmol) and tropolone (47 mg, 0.38 mmol) in 5 mL H$_2$O was refluxed in air for 2 h. The resulting deep green solution was filtered and NH$_4$PF$_6$ (323 mg, 1.98 mmol) was added to give a green precipitate which was filtered and washed with deionized H$_2$O. The green solid was suspended in 10 mL ethanol and 4-tert-butylpyridine (400 µL, 2.73 mmol) was added. The mixture was then refluxed under argon overnight in the presence of a few pieces of zinc amalgam. The resulting brown solution was cooled and the brown precipitate was filtered, washed with ethanol and then air dried. Yield: 93%, 200 mg. ESI-MS: m/z=529.3, [M$^+$].

Preparation of [Ru$^{III}$(Me$_3$tacn)(tropolone)(4-t-butyl-py)](NO$_3$)$_2$

A solution of AgCF$_3$SO$_3$ (92 mg, 0.36 mmol) in acetone (5 mL) was slowly added to the brown acetone solution (10 mL) of [Ru$^{II}$(Me$_3$tacn)(tropolone)(4-t-butyl-py)]PF$_6$ (200 mg, 0.30 mmol). The brown solution turned green immediately and the mixture was stirred in the dark for 30 minutes. The silver metal in the solution was removed by centrifuge and the green solution was then slowly added to ca. 80 mL diethyl ether. The green precipitate was collected by filtration and washed with diethyl ether. It was then dissolved in 5 mL acetone and a solution of [$^n$Bu$_4$N]NO$_3$ (271 mg, 0.89 mmol) in acetone (5 mL) was slowly added. The green precipitate was filtered, washed with acetone and vacuum dried. Yield: 33%, 65 mg. ESI-MS: m/z=264.8, [M$^{2+}$]. E$_{1/2}$ of Ru$^{III/II}$=0.23V vs. NHE in buffer solution (pH 8.20).

EXAMPLE 14

See FIGS. 62-63 and 63a-c

[Ru$^{III}$(Me$_3$tacn)(acac)(3,4-Me$_2$py)](CF$_3$SO$_3$)$_2$

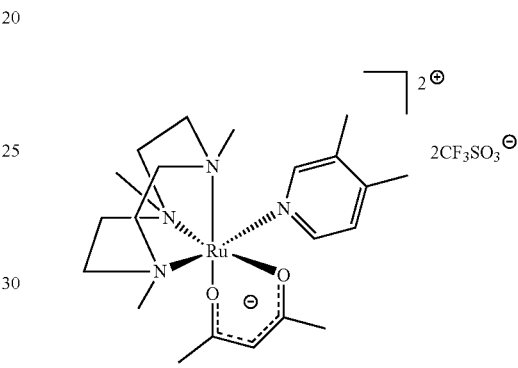

Preparation of [Ru$^{II}$(Me$_3$tacn)(acac)(3,4-Me$_2$py)](PF$_6$)

3,4-Lutidine (0.3 g, 2.8 mmol) was added to [Ru$^{III}$(Me$_3$tacn)(acac)(OH)]PF$_6$ (300 mg, 0.56 mmol) in absolute ethanol (10 mL). The solution was refluxed under argon in the presence Zn amalgam (10 pieces) for 24 h. After cooling to room temperature, the orange solid was filtered and recrystallized from acetone/diethyl ether. Yield (300 mg).

Preparation of [Ru$^{III}$(Me$_3$tacn)(acac)(3,4-Me$_2$py)](CF$_3$SO$_3$)$_2$

A solution of AgCF$_3$SO$_3$ (135 mg, 0.48 mmol) in acetone (2 mL) was slowly added to an orange solution of [Ru$^{II}$(Me$_3$tacn)(acac)(3,4-Me$_2$py)](PF$_6$) (300 mg, 0.48 mmol) in acetone (10 mL). After 5 minutes the purple solution was filtered and concentrated to ca 1 mL. Addition of diethyl ether (50 mL) gave a purple solid which was collected and recrystallized from acetone/diethyl ether. Yield (300 mg). The purple solid (300 mg) was then re-dissolved in a minimum amount of acetone and neat triflic acid (0.5 mL) was then added with vigorous stirring. The purple solution was then slowly added to diethyl ether (500 mL). The purple precipitate was filtered and dried under vacuum. Yield: (150 mg).

ESI/MS (positive mode) in acetone: m/z=239.7, [M]$^{2+}$. $E_{1/2}$ of Ru$^{III/II}$=+0.17 V vs. NHE in buffer solution (pH 8.20).

EXAMPLE 15

See FIGS. 64-65 and 65a-c

[Ru$^{III}$(Me$_3$tacn)(acac)(3-OHpy)](NO$_3$)$_2$

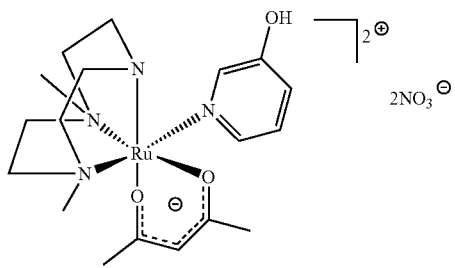

Preparation of [Ru$^{II}$(Me$_3$tacn)(acac)(3-OHpy)](PF$_6$)

3-Hydroxypyridine (0.1 g, 1.05 mmol) was added to [Ru$^{III}$(Me$_3$tacn)(acac)(OH)]PF$_6$ (200 mg, 0.37 mmol) in absolute ethanol (10 mL). The solution was refluxed under argon in the presence Zn amalgam (10 pieces) for 16 h. After cooling to room temperature, the orange solution was filtered and concentrated to ca. 1 mL. Addition of diethyl ether (50 mL) gave an orange solid which was filtered and recrystallized from acetone/diethyl ether. Yield (160 mg).

Preparation of [Ru$^{III}$(Me$_3$tacn)(acac)(3-OHpy)](NO$_3$)$_2$

A solution of AgCF$_3$SO$_3$ (70 mg, 0.27 mmol) in acetone (2 mL) was slowly added to the orange solution of [Ru$^{II}$(Me$_3$tacn)(acac)(3-OHpy)](PF$_6$) (160 mg, 0.26 mmol) in acetone (8 mL). After 5 minutes the purple solution was filtered and concentrated to ca 1 mL. Addition of diethyl ether (50 mL) gave a purple solid which was filtered and recrystallized from acetone/diethyl ether. Yield (150 mg). The purple solid (150 mg) was then re-dissolved in acetone (8 ml) and a solution of [N$^n$Bu$_4$](NO$_3$) (200 mg) in acetone (2 ml) was then slowly added. The purple precipitate was filtered and dried under vacuum. Yield: (100 mg). ESI/MS (positive mode) in methanol: m/z=233.8, [M]$^{2+}$. $E_{1/2}$ of Ru$^{III/II}$=+0.14 V vs. NHE in buffer solution (pH 8.20).

EXAMPLE 16

See FIGS. 66-67 and 67a-c

[Ru$^{III}$(tmc)(NCS)$_2$](ClO$_4$)

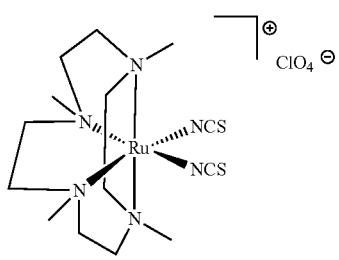

Preparation of [Ru$^{III}$(TMC)(NCS)$_2$](ClO$_4$)

The purple solid is prepared according a literature method. (Che, C. M.; Kwong, S. S.; Poon C. K. *Inorg. Chem.* 1985, 24, 1601-1602).

EXAMPLE 17

The aim of the experiment was to demonstrate measurement of creatine kinase activity by wet testing with [Ru$^{III}$(Me$_3$TACN)(acac)(1-MeIm)](NO$_3$)$_2$.

Enzyme Mixture

Enzyme mix was prepared with the following composition:

0.1M imidazole (balanced with acetic acid, pH 7.1 at 37° C.)
40 mM [Ru$^{III}$(Me$_3$TACN)(acac)(1-MeIm)](NO$_3$)$_2$
20 mM nicotinamide adenine dinucleotide
5 mg/ml diaphorase
5 mg/ml glucose 6-phosphate dehydrogenase
20 mg/ml hexokinase
20 mM D-glucose
6.25 mM adenosine diphosphate (di-sodium salt)
30 mM magnesium acetate
5 mM EDTA (tetra sodium salt).

CK Solution

Lyophilized human recombinant CK sample was obtained from Asahi Kasei. A stock CK solution in buffer was made at 63.9 kU/L and diluted with buffer to give samples with varying CK activity. The activities of the CK samples were determined using a Space clinical analyser (Schiappanelli Biosystems Inc).

Wet Testing Protocol 9.6 µL enzyme mix was placed in an eppendorf, to which was added 1.2 µL CK sample and 1.2 µL N-acetyl cysteine (200 mM). The eppendorf was placed on a heat block at 37° C. for 3 minutes to incubate the CK in the presence of N-acetyl cysteine and hence activate the CK. The mix was then added to 1.2 µL creatine phosphate (1000 mM) at 37° C.

12 µl of a enzyme/CK mix was then immediately placed on the electrode, and the chronoamperometry test was initiated using a multiplexer (MX452, Sternhagen design) attached to an Autolab (PGSTAT 12).

The oxidation current was measured at 0.15 V at 15 time points (0, 14, 28, 42, 56, 70, 84, 98, 112, 126, 140, 154, 168, 182 and 196 seconds) with a reduction current measured at −0.45 V at the final time point (210 seconds). The transient current was measured for 1 second. Each sample was tested in duplicate.

Analysis

The output from the GPES software was analysed using the DataAnal 2-17 programme for converting data into a spreadsheet. These data were then transferred to the data analysis template.

Results

The sensor responses were plotted vs. time for each CK sample (see FIG. 68). The initial rate of response (change in current for the time period 14-28 seconds) was determined for each sample and a plot made of rate (nA/min) vs. CK activity (kU/L). There was a linear dependence of the rate of response on CK activity determined by the reference method.

EXAMPLE 18

The aim of the experiment was to demonstrate measurement of creatinine by wet testing with [Ru$^{III}$(Me$_3$TACN)(acac)(1-MeIm)](NO$_3$)$_2$ Enzyme Mixture Enzyme mix was prepared with the following composition:
0.1M Tris (balanced with HCl, pH 7.5 at room temperature)
20 mM [Ru$^{III}$(Me$_3$TACN)(acac)(1-MeIm)](NO$_3$)$_2$
10 mM nicotinamide adenine dinucleotide
5 mg/ml diaphorase
80 mg/ml sarcosine dehydrognease
12 mg/ml creatinase
24 mg/mL creatininase.

Creatinine Solution

A stock solution of 10 mM creatinine in buffer was, made and diluted with buffer to give samples with varying concentration of creatinine. Samples were kept on ice until use.

Wet Testing Protocol

12 μl enzyme mix was placed in an eppendorf, which was then placed on a heat block at 37° C. for 3 minutes. The mix was then added to 1.2 μl creatinine sample which had also been incubated on the heat block at 37° C. 12 μl of the enzyme/creatinine mix was then immediately placed on the electrode, and the chronoamperometry test was initiated using a multiplexer (MX452, Sternhagen design) attached to an Autolab (PGSTAT 12).

The oxidation current was measured at 0.15 V at 15 time points (0, 14, 28, 42, 56, 70, 84, 98, 112, 126, 140, 154, 168, 182 and 196 seconds), with a reduction current measured at −0.45 V at the final time point (210 seconds). The transient current was measured for 1 second. Each sample was tested in duplicate.

Analysis

The output from the GPES software was analysed using the DataAnal 2_17 programme. These data were then transferred to the data analysis template.

Results

The sensor responses were plotted vs. creatinine concentration. The slope and intercept for the calibration plot to creatinine at the final time point of 196 seconds are given in FIG. 69.

EXAMPLE 19

The aim of the experiment was to demonstrate measurement of glucose in whole blood using freeze dried sensors prepared with [Ru$^{III}$(Me$_3$TACN)(acac)(1-MeIm)](NO$_3$)$_2$.

Enzyme Mixture

Enzyme mix was prepared with the following composition:
0.1M Tris (balanced with HCl, pH 9.0 at room temperature)
10% w/v KCl
40 mM [Ru$^{III}$(Me$_3$TACN)(acac)(1-MeIm)](NO$_3$)$_2$
10 mM nicotinamide adenine dinucleotide
4.2 mg/ml PdR
10 mg/ml glucose dehydrogenase.

Production Dispense and Freeze Drying 0.4 μL/well of the enzyme mixture was dispensed into well 2 of the sensors using the production dispenser. Three other solutions were dispensed into the other wells. These solutions used alternative mediators and the responses of these sensors are not reported here. The dispensed sensor sheets were then placed into a LS40 freeze drier (Severn Science) for freeze drying. The programme used was Night2. The sensors formed production batch DEV 345.

Whole Blood Samples

A fresh whole blood sample (Li heparin anticoagulant) was used as received. An aliquot of this sample was centrifuged for 5 minutes at 2900 RCF (Labnet 1618), and the plasma tested for glucose concentration using a Space clinical analyser (Schiappanelli Biosystems Inc). The glucose concentration was determined to be 5.1 mM.

In addition, aliquots of the initial whole blood sample were spiked with 1M glucose solution to obtain higher glucose concentrations. A portion of each spiked aliquot was centrifuged and the plasma tested for glucose concentration. Whole blood samples with lower glucose concentration were obtained by centrifugation of an aliquot, replacement of some plasma with delipidated serum (Scipac, S 139) and inversion to reconstitute the sample.

Testing Protocol

20 μl of a whole blood sample was used per electrode. On the addition of sample the chronoamperometry test was initiated using a Uniscan multi-potentiostat. The oxidation current was measured at 0.15 V at 15 time points (0, 14, 28, 42, 56, 70, 84, 98, 112, 126, 140, 154, 168, 182 and 196 seconds), with a reduction current measured at −0.45 V at the final time point (210). The transient current was measured for 1 second. Each sample was tested in duplicate.

Analysis

The output from the GPES software was analysed using the DataAnal 2_17 programme. These data were then transferred to the data analysis template.

Results

The sensor responses were plotted vs. glucose concentration (see FIG. 70). A good correlation between current and whole blood glucose concentration was obtained at 98 seconds (gradient=65.71 nA/sec, intercept=274.18 nA).

EXAMPLE 20

Glucose

Figure 71:
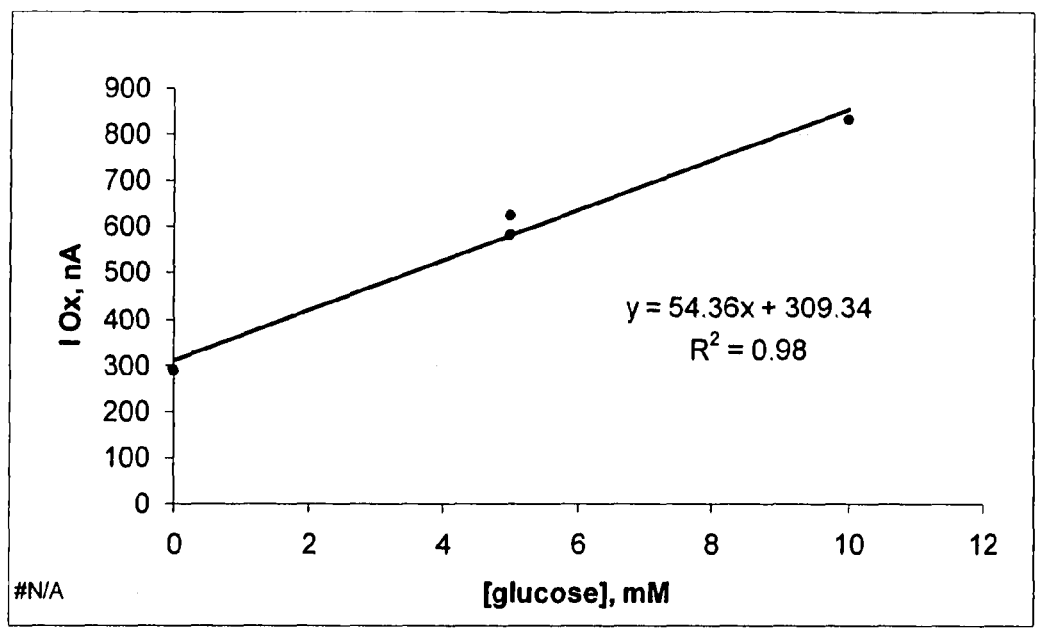

In this Example, the whole blood of Example 19 was replaced by saliva. The results are shown in FIG. 71.

The invention claimed is:

1. A method for measuring an amount or concentration of an analyte, comprising:
   (a) contacting a sample which contains the analyte with a solution containing an enzyme that acts on the analyte and a redox mediator of Formula I

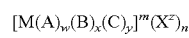   Formula I wherein
   M is ruthenium or osmium and has an oxidation state of 0, 1, 2, 3 or 4;
   each of w, x, and y is an integer independently selected from the integers 1 to 4;
   m is an integer selected from the integers −5 to +4;
   n is an integer selected from selected from the integers 1 to 5;
   z is an integer selected from the integers −2 to +1;
   A is a monodentate 5- or 6-membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino and alkylthio or A is NCS;
   B is a bi-, tri-, tetra-, penta- or hexadentate ligand which is linear having the formula R$^1$RN(C$_2$H$_4$NR)$_w$R$^1$ or cyclic having the formula (RNC$_2$H$_4$)$_v$, (RNC$_2$H$_4$)$_p$(RNC$_3$H$_6$)$_q$ or [(RNC$_2$H$_4$)(RNC$_3$H$_6$)]$_s$, wherein
   w is an integer selected from the integers 1-5, v is an integer selected from the integers 3-6,
each of p and q is an integer independently selected from the integers 1-3 whereby the sum of p and q is 4, 5 or 6,
s is either 2 or 3;
and each of R and $R^1$ is independently hydrogen or alkyl;
C is a ligand other than B; and
X is a counter ion, wherein the number of coordinating atoms is 6, with the exception of $[Ru^{III}(Me_3tacn)(acac)(py)](NO_3)_2)$;
(b) incubating the contacted sample under conditions that cause the enzyme to act on the analyte;
(c) subjecting the incubated sample of step (b) to conditions which result in a change in a measurable signal; and
(d) measuring the measurable signal to determine the amount or concentration of the analyte in the sample.

2. The method of claim 1, wherein ligand A is selected from the group consisting of NCS, imidazole, pyrazole, thiazole, oxazole, isoquinoline, substituted pyridyl, and isomers thereof.

3. The method of claim 1, wherein ligand A is selected from the group consisting of guanine, adenine, a 5-membered heteroaromatic comprising three nitrogen atoms in the ring, a 6-membered heteroaromatic comprising three nitrogen atoms in the ring, imidazole, pyrazole, thiazole, oxazole, and isomers thereof.

4. The method of claim 1, wherein ligand A is substituted by one or more substituents selected from the group consisting of $C_1$-$C_6$ alkyl, $C_1$-$C_6$ alkoxy, $C_2$-$C_6$ alkenyl, $C_2$-$C_6$ alkynyl and halogen.

5. The method of claim 4, wherein ligand A is substituted by one or more substituents selected from the group consisting of methyl, ethyl, propyl, iso-propyl, butyl, t-butyl, methoxy, ethoxy, ethenyl, propenyl, butenyl, ethynyl and propynyl.

6. The method of claim 1, wherein ligand B is selected from the group consisting of a linear ligand of formula $R^1RN(C_2H_4NR)_wR^1$, a cyclic ligand of formula $(RNC_2H_4)_v$, a cyclic ligand of formula $(RNC_2H_4)_p(RNC_3H_6)_q$, and a cyclic ligand of formula $[(RNC_2H_4)(RNC_3H_6)]_s$, wherein w is an integer selected from 1-3, v is 3 or 4, p and q are integers independently selected from 1-3, wherein the sum of p and q is 4, and s is 2 or 3.

7. The method of claim 1, wherein B is selected from the group consisting of 1,4,7-trimethyl-1,4,7-triazacyclononane, 1,1,4,7,10,10-hexamethyltriethylenetetramine, 1,2-dimethylethylenediamine and 1,1,2,2-tetramethylethylenediamine.

8. The method of claim 1, wherein ligand C is selected from the group consisting of $NH_2$, CO, CN, a halogen, acetylacetonate (acac), 3-bromo-acetylacetonate (Bracac), oxalate, pyridine and 5-chloro-8-hydroxyquinoline.

9. The method of claim 1, wherein the complex of Formula I is selected from the group consisting of
$[Ru^{III}(1,4,7\text{-trimethyl-1,4,7-triazacyclononane)(acac)(N-methylimidazole)}](NO_3)_2$,
$[Ru^{III}(1,4,7\text{-trimethyl-1,4,7-triazacyclononane)(acac)(4-methylpyridine)}]Cl_2$,
$[Ru^{III}(1,4,7\text{-trimethyl-1,4,7-triazacyclononane)(acac)(3-chloropyridine)}](NO_3)_2$,
$[Ru^{III}(1,4,7\text{-trimethyl-1,4,7-triazacyclononane)(acac)(isonicotinamide)}](NO_3)_2$,
$[Ru^{III}(1,4,7\text{-trimethyl-1,4,7-triazacyclononane)(acac)pyrazine}](NO_3)_2$,
$[Ru^{III}(1,4,7\text{-trimethyl-1,4,7-triazacyclononane)(acac)(4-methoxypyridine)}](NO_3)_2$,
$[Ru^{III}(1,4,7\text{-trimethyl-1,4,7-triazacyclononane)(acac)(4-dimethylaminopyridine)}](NO_3)_2$,
$[Ru^{III}(1,4,7\text{-trimethyl-1,4,7-triazacyclononane)(acac)(4-t-butyl-pyridine)}](NO_3)_2$,
$[Ru^{III}(1,4,7\text{-trimethyl-1,4,7-triazacyclononane)(acac)(isoquinoline)}](NO_3)_2$,
$[Ru^{III}(1,4,7\text{-trimethyl-1,4,7-triazacyclononane)(tropolone)(pyridine)}](NO_3)_2$,
$[Ru^{III}(1,4,7\text{-trimethyl-1,4,7-triazacyclononane)(tropolone)(4-t-butyl-pyridine)}](NO_3)_2$,
$[Ru^{III}(1,4,7\text{-trimethyl-1,4,7-triazacyclononane)(acac)(3,4-dimethylpyridine)}](CF_3SO_3)_2$,
$[Ru^{III}(1,4,7\text{-trimethyl-1,4,7-triazacyclononane)(acac)(3-hydroxypyridine)}](NO_3)_2$, and
$[Ru^{III}(1,4,8,11\text{-tetramethyl-1,4,8,11-tetra-azacyclotetradecane)(NCS)_2}](ClO_4)$.

10. The method of claim 1, wherein the complex of Formula I is selected from the group consisting of $[Ru^{III}(1,4,7\text{-trimethyl-1,4,7-triazacyclononane)(acac)(N-methylimidazole)}](PF_6)_2$ and $[Ru^{III}(1,4,7\text{-trimethyl-1,4,7-triazacyclononane)(acac)(N-methylimidazole)}](NO_3)_2$.

11. A complex according to Formula I $$[M(A)_w(B)_x(C)_y]^m(X^Z)_n \qquad \text{Formula 1}$$

wherein
M is ruthenium or osmium and has an oxidation state of 0, 1, 2, 3 or 4;
each of w, x, and y is an integer independently selected from the integers 1 to 4;
m is an integer selected from the integers −5 to +4;
n is an integer selected from selected from the integers 1 to 5;
z is an integer selected from the integers −2 to +1;
A is a monodentate 5- or 6-membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —$NO_2$, —CN, —$CO_2H$, —$SO_3H$, —$NHNH_2$, —SH, aryl, alkoxycarbonyl, alkylaminocarbonyl, dialkylaminocarbonyl, —OH, alkoxy, —NH2, alkylamino, dialkylamino, alkanoylamino, arylcarboxamido, hydrazino, alkylhydrazino, hydroxylamino, alkoxyamino and alkylthio;
B is a bi-, tri-, tetra-, penta- or hexadentate ligand which is linear having the formula $R^1RN(C_2H_4NR)_wR^1$ or cyclic having the formula $(RNC_2H_4)_v$, $(RNC_2H_4)_p(RNC_3H_6)_q$ or $[(RNC_2H_4)(RNC_3H_6)]_s$, wherein
w is an integer selected from the integers 1-5,
v is an integer selected from the integers 3-6,
each of p and q is an integer independently selected from the integers 1-3 whereby the sum of p and q is 4, 5 or 6,
s is either 2 or 3 and
each of R and $R^1$ is independently hydrogen or alkyl;
C is a ligand other than A or B; and
X is a counter ion,
wherein the number of coordinating atoms is 6, with the exception of $[Ru^{III}(Me_3tacn)(acac)(Py)](NO_3)_2$; and
wherein the complex is selected from the group consisting of $[Ru^{III}(1,4,7\text{-trimethyl-1,4,7-triazacyclononane)(acac)(N-methylimidazole)}](NO_3)_2$, $[Ru^{III}(1,4,7\text{-trimethyl-1,4,7-triazacyclononane)(acac)(4-methylpyridine)}]Cl_2$, $[Ru^{III}(1,4,7\text{-trimethyl-1,4,7-triazacyclononane)(acac)(3-chloropyridine)}](NO_3)_2$, $[Ru^{III}(1,4,7\text{-triazacyclononane)(acac)(isonicotinamide)}](NO_3)_2$, $[Ru^{III}(1,4,7\text{-trimethyl-1,4,7-triazacyclononane)(acac)pyrazine}]$ (NO$_3$)$_2$, [Ru$^{III}$(1,4,7-trimethyl-1,4,7-triazacyclononane)(acac)(4-methoxypyridine)](NO$_3$)$_2$, [Ru$^{III}$(1,4,7-trimethyl-1,4,7-triazacyclononane)(acac)(4-dimethylaminopyridine)](NO$_3$)$_2$, [Ru$^{III}$(1,4,7-trimethyl-1,4,7-triazacyclononane)(acac)(4-t-butyl-pyridine)](NO$_3$)$_2$, [Ru$^{III}$(1,4,7-trimethyl-1,4,7-triazacyclononane)(acac)(isoquinoline)](NO$_3$)$_2$, [Ru$^{III}$(1,4,7-trimethyl-1,4,7-triazacyclononane)(tropolone)(pyridine)](NO$_3$)$_2$, [Ru$^{III}$(1,4,7-trimethyl-1,4,7-triazacyclononane)(tropolone)(4-t-butyl-pyridine)](NO$_3$)$_2$, [Ru$^{III}$(1,4,7-trimethyl-1,4,7-triazacyclononane)(acac)(3,4-dimethylpyridine)](CF$_3$SO$_3$)$_2$, and [Ru$^{III}$(1,4,7-trimethyl-1,4,7-triazacyclononane)(acac)(3-hydroxypyridine)](NO$_3$)$_2$.

12. A complex according to Formula I $$[M(A)_w(B)_x(C)_y]^m(X^Z)_n \qquad \text{Formula 1}$$

wherein

M is ruthenium or osmium and has an oxidation state of 0, 1, 2, 3 or 4;

each of w, x, and y is an integer independently selected from the integers 1 to 4;

m is an integer selected from the integers −5 to +4;

n is an integer selected from selected from the integers 1 to 5;

z is an integer selected from the integers −2 to +1;

A is a monodentate 5- or 6- membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —NO$_2$, —CN, —CO$_2$H, —SO$_3$H, -NHNH$_2$, —SH, aryl, alkoxycarbonyl, alkylaminocarbonyl, dialkylaminocarbonyl, —OH, alkoxy, —NH2, alkylamino, dialkylamino, alkanoylamino, arylcarboxamido, hydrazino, alkylhydrazino, hydroxylamino, alkoxyamino and alkylthio;

B is a bi-, tri-, tetra-, penta- or hexadentate ligand which is linear having the formula R$^1$RN(C$_2$H$_4$NR)$_w$R$^1$ or cyclic having the formula (RNC$_2$H$_4$)$_v$, (RNC$_2$H$_4$)$_p$(RNC$_3$H$_6$)$_q$ or [(RNC$_2$H$_4$)(RNC$_3$H$_6$)]$_s$, wherein w is an integer selected from the integers 1-5, v is an integer selected from the integers 3-6, each of p and q is an integer independently selected from the integers 1-3 whereby the sum of p and q is 4, 5 or 6, s is either 2 or 3 and each of R and R$^1$ is independently hydrogen or alkyl;

C is a ligand other than A or B; and

X is a counter ion, wherein the number of coordinating atoms is 6, with the exception of [Ru$^{III}$(Me$_3$tacn)(acac)(Py)](NO$_3$)$_2$; and wherein the complex is selected selected from the group consisting of [Ru$^{III}$(1,4,7-trimethyl-1,4,7-triazacyclononane)(acac)(N-methylimidazole)](PF$_6$)$_2$ and Ru$^{III}$(1,4,7-trimethyl-1,4,7-triazacyclononane)(acac)(N-methylimidazole)](NO$_3$)$_2$.

13. A complex according to Formula 1

$$[M(A)_w(B)_x(C)_y]^m(X^Z)_n \qquad \text{Formula 1}$$

wherein

M is ruthenium or osmium and has an oxidation state of 0, 1, 2, 3 or 4;

each of w, x, and y is an integer independently selected from the integers 1 to 4;

m is an integer selected from the integers −5 to +4;

n is an integer selected from selected from the integers 1 to 5;

z is an integer selected from the integers −2 to +1;

A is a monodentate 5- or 6-membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH2, alkylamino, dialkylamino, alkanoylamino, arylcarboxamido, hydrazino, alkylhydrazino, hydroxylamino, alkoxyamino and alkylthio;

B is a bi-, tri-, tetra-, penta- or hexadentate ligand which is linear having the formula R$^1$RN(C$_2$H$_4$NR)$_w$R$^1$ or cyclic having the formula (RNC$_2$H$_4$)$_v$, (RNC$_2$H$_4$)$_p$(RNC$_3$H$_6$)$_q$ or [(RNC$_2$H$_4$)(RNC$_3$H$_6$)]$_s$, wherein w is an integer selected from the integers 1-5, v is an integer selected from the integers 3-6, each of p and q is an integer independently selected from the integers 1-3 whereby the sum of p and q is 4, 5 or 6, s is either 2 or 3 and each of R and R$^1$ is independently hydrogen or alkyl;

C is a ligand other than A or B; and

X is a counter ion, wherein the number of coordinating atoms is 6, with the exception of [Ru$^{III}$(Me$_3$tacn)(acac)(Py)](NO$_3$)$_2$; and wherein ligand A is selected from the group consisting of guanine, adenine, a 5-membered heteroaromatic comprising three nitrogen atoms in the ring, a 6-membered heteroaromatic comprising three nitrogen atoms in the ring, imidazole, pyrazole, thiazole, oxazole, and isomers thereof.

14. A complex according to Formula I $$[M(A)_w(B)_x(C)_y]^m(X^Z)_n \qquad \text{Formula 1}$$

wherein

M is ruthenium or osmium and has an oxidation state of 0, 1, 2, 3 or 4;

each of w, x, and y is an integer independently selected from the integers 1 to 4;

m is an integer selected from the integers −5 to +4;

n is an integer selected from selected from the integers 1 to 5;

z is an integer selected from the integers −2 to +1;

A is a monodentate 5- or 6-membered aromatic ligand containing 1, 2 or 3 nitrogen atoms which is optionally substituted by 1 to 8 substituents each selected from the group consisting of substituted or unsubstituted alkyl, alkenyl, or aryl groups, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH2, alkylamino, dialkylamino, alkanoylamino, arylcarboxamido, hydrazino, alkylhydrazino, hydroxylamino, alkoxyamino and alkylthio;

B is a bi-, tri-, tetra-, penta- or hexadentate ligand which is linear having the formula R$^1$RN(C$_2$H$_4$NR)$_w$R$^1$ or cyclic having the formula (RNC$_2$H$_4$)$_v$, (RNC$_2$H$_4$)$_p$(RNC$_3$H$_6$)$_q$ or [(RNC$_2$H$_4$)(RNC$_3$H$_6$)]$_s$, wherein w is an integer selected from the integers 1-5, v is an integer selected from the integers 3-6, each of p and q is an integer independently selected from the integers 1-3 whereby the sum of p and q is 4, 5 or 6, s is either 2 or 3 and each of R and $R^1$ is independently hydrogen or alkyl;

C is a ligand other than A or B; and

X is a counter ion, wherein the number of coordinating atoms is 6, with the exception of $[Ru^{III}(Me_3tacn)(acac)(Py)](NO_3)_2$; and wherein B is selected from the group consisting of 1,4,7-trimethyl-1,4,7-triazacyclononane, 1,1,4,7,10,10-hexamethyltriethylenetetramine, 1,2-dimethylethylenediamine and 1,1,2,2-tetramethylethylenediamine.

* * * * *